US008741567B2

(12) United States Patent (10) Patent No.: US 8,741,567 B2
He et al. (45) Date of Patent: Jun. 3, 2014

(54) COMPOSITION AND METHODS RELATED TO MODIFICATION OF 5-HYDROXYMETHYLCYTOSINE (5-HMC)

(75) Inventors: Chuan He, Chicago, IL (US); Chunxiao Song, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 13/095,505

(22) Filed: Apr. 27, 2011

(65) Prior Publication Data

US 2011/0301045 A1 Dec. 8, 2011

Related U.S. Application Data

(63) Continuation of application No. PCT/US2011/031370, filed on Apr. 6, 2011.

(60) Provisional application No. 61/321,198, filed on Apr. 6, 2010.

(51) Int. Cl.
*C12Q 1/68* (2006.01)
*C07H 21/00* (2006.01)

(52) U.S. Cl.
USPC ........................ 435/6.11; 435/6.12; 536/25.32

(58) Field of Classification Search
None
See application file for complete search history.

(56) References Cited

U.S. PATENT DOCUMENTS

| 6,312,906 B1 | 11/2001 | Cass et al. ..................... 435/6.11 |
| 7,122,359 B2* | 10/2006 | Thorson et al. ............... 435/193 |
| 2009/0181373 A1 | 7/2009 | Li et al. ......................... 435/6.12 |

OTHER PUBLICATIONS

Song et al., "Selective chemical labeling reveals the genome-wide distribution of 5-hydroxymethylcytosine," Nature Biotechnology, vol. 29, No. 1, Dec. 2010 (online) and Jan. 2011 (in print).*
Amit et aL, "Feeder Layer- and Serum-Free Culture of Human Embryonic Stem Cells," *Biol Reprod* 70(3): 837-845. Mar. 2004.
Drake et al., "Synthesis and properties of 5-azido-UDP-glucose,"*J Biological Chemistry* 264(20): 11928-11933. Jul. 15, 1989.
Evans, "The Rise of Azide-Alkyne 1,3-Dipolar 'Click' Cycloaddition and its Application to Polymer Science and Surface Modification," *Australian Journal of Chemistry* 60(6): 384-395. Jun. 18, 2007.
Flusberg, "Direct detection of DNA methylation during single-molecule, real-time sequencing," *Nat Methods* 7(6):461-465. Jun. 2010.
Gefter et al., "The enzymatic methylation of ribonucleic acid and deoxyribonucleic acid.," *J Biol Chem* 241(9): 1995-2006. May 10, 1966.
Gold and Schweiger, "Synthesis of Phage-Specific α- and β-Glycosyl Transferases Directed by T-Even DNA in Vitro," *Biochemistry* 62:892-808. 1969.
Hein et aL, "Click Chemistry, a Powerful Tool for Pharmaceutical Sciences," *Pharmaceutical Research* 25(10): 2216-2230. Oct. 2008.

Huang, "Digestion of highly modified bacteriophage DNA by restriction endonucleases," *Nucleic Acids Research* 10(5): 1579-1591. Mar. 11, 1982.
Huang, "The behaviour of 5-hydroxymethylcytosine in bisulfate sequencing," *PLoS One* 5(1):e8888. Jan. 26, 2010.
Ito et al., "Role of Tet proteins in 5mC to 5hmC conversion, ES-cell self-renewal and inner cell mass specification," *Nature* 466(7310): 1129-1133. Aug. 26, 2010.
Jin et al., "Examination of the specificity of DNA methylation profiling techniques towards 5-methylcytosine and 5-hydroxymethylcytosine," *Nucleic Acids Research* 38(11):e125. Jun. 1, 2010.
Josse and Kornberg, "Glucosylation of deoxyribonucleic acid. III. alpha- and beta-Glucosyl transferases from T4-infected *Escherichia coli*," *J Biol Chem* 237:1968-1976. Jul. 1962.
Kolb et al, "Click Chemistry: Diverse Chemical Function from a Few Good Reactions," *Angew Chem Int Ed* 40(11): 2004-2021. Jun. 1, 2001.
Kriaucionis and Heintz, "The Nuclear DNA Base 5-Hydroxymethylcytosine is Present in Purkinje Neurons and the Brain," *Science* 324:929-930. May 15, 2009.
Larivière and Moréra, "Structural evidence of a passive base-flipping mechanism for beta-glucosyltransferase," *J Biol Chem* 279(33):34715-34720. Aug. 13, 2004.
Meyer et al., "Chemical restriction: strand cleavage by ammonia treatment at 8-oxoguanine yields biologically active DNA," *ChemBioChem* 4(7):610-614. Jul. 7, 2003.
Moses and Moorhouse, "The Growing Applications of Click Chemistry," *Chem Soc Rev* 36:1249-1262. 2007.
New England Biolabs, "Dam($G^m$ATC), Dcm($C^m$CWGG) and CpG($^m$CG) Methylation." Downloaded Apr. 2, 2010.
New England Biolabs, "Effects of CpG Methylation on Restriction Enzyme Cleavage." Downloaded Apr. 2, 2010.
Padwa, *Synthetic applications of 1,3-Dipolar Cycloaddition Chemistry toward heterocycles and natural products*. William H. Pearson. Chichester: Wiley, 2002.
PCT International Search Report and Written Opinion issued in International application No. PCT/US11/31370 dated Jun. 1, 2011.
Robertson et al., "A novel method for the efficient and selective identification of 5-hydroxymethylcytosine in genomic DNA," *Nucleic Acids Research* 1-10. Advanced access Feb. 7, 2011.
Sletten and Bertozzi, "Bioorthogonal chemistry: fishing for selectivity in a sea of functionality," *Angew Chem Int Ed* 48(38): 6974-6998. 2009.
Song et al., "Selective chemical labeling reveals the genome-wide distribution of 5-hydroxymethylcytosine," *Nature Biotechnology* 29(1):68-72. 2011.
Speers and Cravatt, "Profiling enzyme activities in vivo using click chemistry methods," *Chem Biol* 11(4):535-546. Apr. 2004.

(Continued)

*Primary Examiner* — Bradley L Sisson
(74) *Attorney, Agent, or Firm* — Fulbright & Jaworski LLP

(57) ABSTRACT

The present invention relates generally to the field of molecular biology. More particularly, it concerns methods and compositions for detecting, evaluating, and/or mapping 5-hydroxymethyl-modified cytosine bases within a nucleic acid molecule.

25 Claims, 29 Drawing Sheets

(56) References Cited

OTHER PUBLICATIONS

Szwagierczak et al., "Sensitive enzymatic quantification of 5-hydroxymethylcytosine in genomic DNA," *Nucleic Acids Research* 38(19):e181. Oct. 1, 2010.

Tahiliani et al., "Conversion of 5-methylcytosine to 5-hydroxymethylcytosine in mammalian DNA by MLL partner TET1," *Science* 324(5929): 930-935. May 15, 2009.

Tanabe et al., "One-electron photooxidation and site-selective strand cleavage at 5-methylcytosine in DNA by sensitization with 2-methyl-1,4-naphthoquinone-tethered oligonucleotides," *J Am Chem Soc* 129(25): 8034-8040. Jun. 27, 2007.

Vrielink et al., "Crystal structure of the DNA modifying enzyme β-glucosyltransferase in the presence and absence of the substrate uridine diphosphoglucose," *EMBO J* 13(15): 3413-3422. Aug. 1, 1994.

Wu and Zhang, "Active DNA demethylation: many roads lead to Rome," *Nature Reviews Molecular Cell Biology* 11:607-620. Oct. 2010.

* cited by examiner

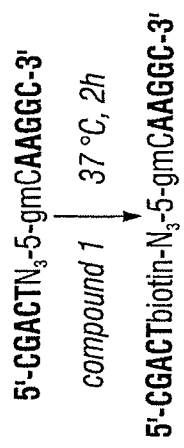
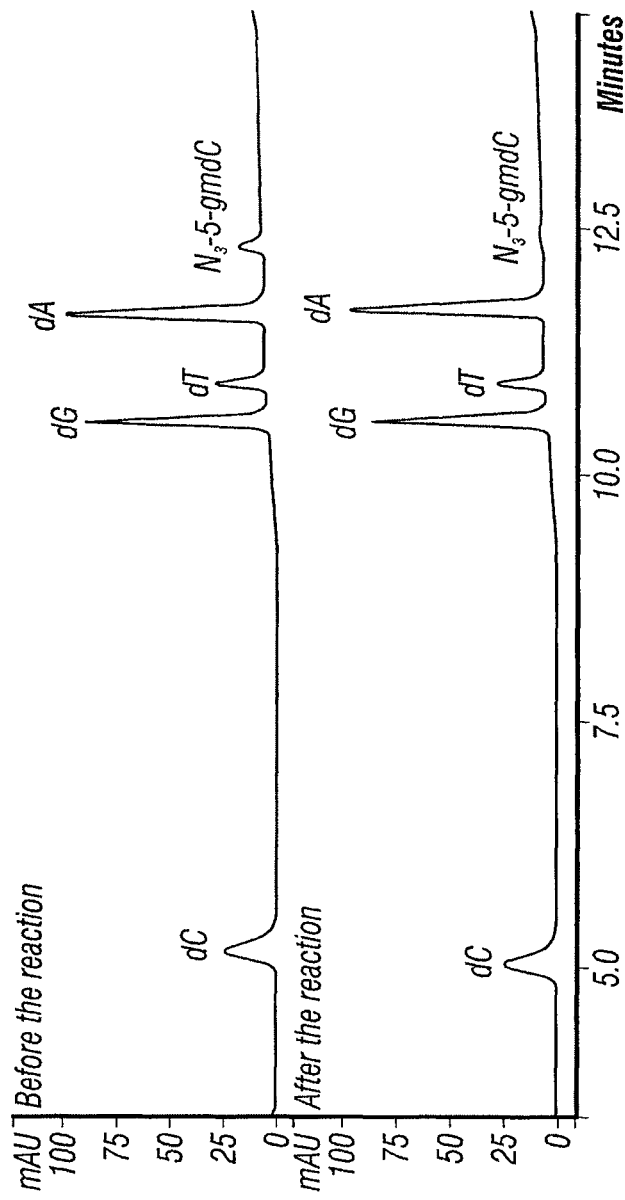
FIG. 7A
FIG. 7B

*5-hmC spike:*
5'-CGCTTAGGTACCAGTTGCTGGCTTGGTGGCCTTAGAGGTACTGAGAAGCTTTCGTGCCCA-3'
3'-GCGAATCCATGGTCAACGACCGAACCACCGGAATCTCCATGACTCTTCGAAAGCACGGGT-5'

*control spike:*
5'-CGCTTAGGGACCAGTCGCTGGCTTGGTGGCCTTAGAGGTACTGAGGAGCTCTCGTGCCCA-3'
3'-GCGAATCCGTGGTCAGCGACCGAACCACCGGAATCTCCATGACTCCTCGAGAGCACGGGT-5'

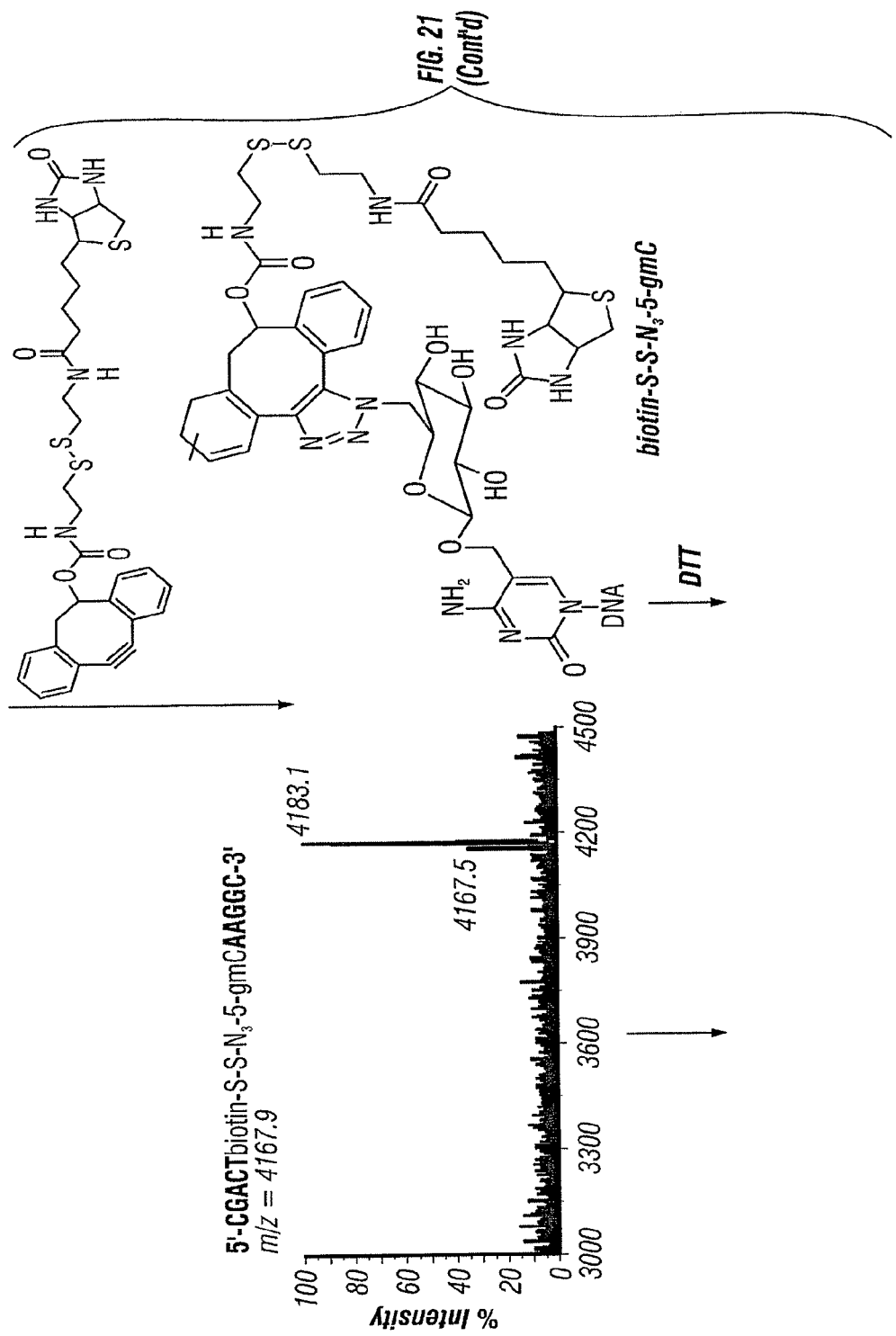

ated nucleic acid molecule. Subsequent manipulation of the glycosylated nucleic acid using any number of different nucleic acid modifications is contemplated.
COMPOSITION AND METHODS RELATED TO MODIFICATION OF 5-HYDROXYMETHYLCYTOSINE (5-HMC)

This invention was made with government support under GM071440 awarded by the National Institutes of Health. The government has certain rights in the invention.

This application claims priority to U.S. Provisional Patent Application Ser. No. 61/321,198 filed Apr. 6, 2010, which is incorporated herein by reference in its entirety.

BACKGROUND OF THE INVENTION

I. Field of the Invention

The present invention relates generally to the field of molecular biology. More particularly, it concerns methods and compositions for detecting, evaluating, and/or mapping 5-hydroxymethyl-modified cytosine bases within a nucleic acid molecule.

II. Background

5-Methylcytosine (5-mC) constitutes approximately 2-8% of the total cytosines in human genomic DNA, and impacts a broad range of biological functions, including gene expression, maintenance of genome integrity, parental imprinting, X-chromosome inactivation, regulation of development, aging, and cancer. Recently, the presence of an oxidized 5-mC, 5-hydroxymethylcytosine (5-hmC), has been discovered in embryonic and neuronal stem cells, certain adult brain cells, and some cancer cells.

There is a need for methods and compositions for detecting and evaluating 5-hmC in the genome of eukaryotic organisms.

SUMMARY OF THE INVENTION

The inability to distinguish between 5-hydroxymethylcytosine (5-hmC) and 5-methylcytosine (5-mC) presents challenges to studying and understanding better the significance of endogenous hydroxylation of 5-methylcytosine in genomic DNA. Solutions that enable detection or mapping of the hydroxymethylation state open the door to diagnostic and therapeutic applications. Accordingly, methods and compositions are provided and described.

In a number of embodiments, 5-hydroxymethylcytosines (5-hmC)—and specifically not 5-methylcytosines (5-mC)—are modified in a nucleic acid molecule. Methods and compositions involve β-glucosyltransferase (βGT), which is in the glycosyltransferase family of enzymes and which selectively glycosylates 5-hmC.

Generally, embodiments involve selectively glycosylating 5-hmC in a nucleic acid sample and directly or indirectly detecting, qualitatively and/or quantitatively, the glycosylated nucleotides based on a molecule or compound that is attached to glycosylated nucleotide. The attachment to the glycosylated nucleotide may occur at the time the nucleotide is glycosylated through the use of a modified UDP-Glu molecule with the attachment, or the attachment may be attached subsequent to the glycosylation with the modified Glu molecule. Other embodiments involve a modified and glycosylated nucleic acid molecule. Subsequent manipulation of the glycosylated nucleic acid using any number of different nucleic acid modifications is contemplated.

In some embodiments, there are methods for at least the following: distinguishing 5-hydroxymethylcytosine from 5-methylcytosine in a nucleic acid molecule; modifying a nucleic acid molecule containing at least one 5-hydroxymethylcytosine; identifying 5-hydroxymethylcytosine in genomic DNA; preparing a nucleic acid that has been modified at nucleotides that containing a 5-hmC prior to modification (and specifically not modifying nucleotides that have a 5-mC; and, comparing a first nucleic acid sample with at least a second nucleic acid sample based on the presence and/or absence of 5-hydroxymethylcytosine in nucleic acids in the first sample.

Methods may involve any of the following steps described herein. In some embodiments, methods involve incubating the nucleic acid molecule with β-glucosyltransferase and a modified uridine diphosphoglucose (UDP-Glu) molecule to glycosylate 5-hydroxymethylcytosine in the nucleic acid molecule with a modified glucose (Glu) molecule. In other embodiments, methods may involve mixing the nucleic acids with β-glucosyltransferase and a modified uridine diphosphoglucose (UDP-Glu) molecule under conditions to promote glycosylation of the 5-hydroxymethylcytosines in the nucleic acids with a modified glucose (Glu) molecule. Other embodiments may involve contacting the nucleic acids with β-glucosyltransferase and a modified uridine diphosphoglucose (UDP-Glu) molecule under conditions to promote glycosylation of the 5-hydroxymethylcytosines in the nucleic acids with a modified glucose (Glu) molecule. In still further embodiments, a composition comprising nucleic acids, an effective amount of β-glucosyltransferase and a modified uridine diphosphoglucose (UDP-Glu) molecule is generated and then placed under conditions to promote glycosylation of the 5-hydroxymethylcytosines in the nucleic acids with a modified glucose (Glu) molecule. It is specifically contemplated that reactions involving any enzymes may be restricted or limited by time, enzyme concentration, substrate concentration, and/or template concentration. For example, there may be a partial restriction enzyme digest or partial glycosylation of nucleic acid molecules. Reaction conditions may be adjusted so that the reaction is carried out under conditions that result in about, at least about, or at most about 20, 30, 40, 50, 60, 70, 80, 90, 95, 96, 97, 98, 99, 100% completion, or any range derivable therein.

In some embodiments, methods may also involve one or more of the following regarding nucleic acids prior to and/or concurrent with glycosylation of nucleic acids (generating a nucleic acid that is glycosylated on nucleotides that were 5-hmC nucleotides): obtaining nucleic acid molecules; obtaining nucleic acid molecules from a biological sample; obtaining a biological sample containing nucleic acids from a subject; isolating nucleic acid molecules; purifying nucleic acid molecules; obtaining an array or microarray containing nucleic acids to be glycosylated; denaturing nucleic acid molecules; shearing or cutting nucleic acid; denaturing nucleic acid molecules; hybridizing nucleic acid molecules; incubating the nucleic acid molecule with an enzyme that is not β-glucosyltransferase; incubating the nucleic acid molecule with a restriction enzyme; attaching one or more chemical groups or compounds to the nucleic acid; conjugating one or more chemical groups or compounds to the nucleic acid; incubating nucleic acid molecules with an enzyme that modifies the nucleic acid molecules by adding or removing one or more elements, chemical groups, or compounds.

Methods may further involve one or more of the following steps that is concurrent with and/or subsequent to glycosylation of nucleic acids: isolating nucleic acids glycosylated with the modified glucose; isolating glycosylated (and modified) nucleic acids based on the modification to the glucose; purifying glycosylated (and modified) nucleic acids based on the modification to the glucose; reacting the modified glucose in the glycosylated nucleic acid molecule with a detectable or functional moiety, such as a linker; conjugating or attaching a detectable or functional moiety to the glycosylated nucleotide; exposing to, incubating with, or mixing with the glycosylated nucleic acid an enzyme that will use the glycosylated nucleic acid as a substrate independent of the modification to the glucose; exposing to, incubating with, or mixing with the glycosylated nucleic acid an enzyme that will use the glycosylated nucleic acid as a substrate unless the modification to the glucose modifies, alters, prevents, or hinders it; exposing to, incubating with, or mixing with the glycosylated nucleic acid an enzyme that will use the glycosylated nucleic acid as a substrate unless the modification sterically prevents or inhibits the enzyme; enriching for nucleic acids containing modified and glycosylated nucleic acids; identifying 5-hydroxymethylcytosines in the nucleic acids using the modified glucose molecule, identifying 5-hydroxymethylcytosines in the nucleic acid by comparing glycosylated nucleic acids with unglycosylated nucleic acids; mapping the 5-hydroxymethylcytosines in the nucleic acid molecule; subjecting the glycosylated nucleic acid to chromatography; subjecting the glycosylated nucleic acid to a primer extension assay and comparing the results to a control nucleic acid; subjecting the glycosylated nucleic acid to a hybridization assay and comparing the results to a control nucleic acid; and/or sequencing the glycosylated nucleic acid and comparing the results to a control nucleic acid.

Methods may also involve the following steps: cloning β-glucosyltransferase (βGT); synthesizing β-glucosyltransferase or a functional fragment thereof; isolating β-glucosyltransferase; purifying β-glucosyltransferase; synthesizing β-glucosyltransferase; placing β-glucosyltransferase in a sterile container; shipping purified or isolated β-glucosyltransferase in a container; and/or providing instructions regarding use of β-glucosyltransferase; incubating β-glucosyltransferase with UDP-glucose molecules and a nucleic acid substrate under conditions to promote glycosylation of the nucleic acid with the glucose molecule (which may or may not be modified) and result in a nucleic acid that is glycosylated at one or more 5-hydroxymethylcytosines.

Methods and compositions may involve a purified nucleic acid, modified UDP-Glu, and/or enzyme, such as β-glucosyltransferase. Such protocols are known to those of skill in the art. In certain embodiments, purification may result in a molecule that is about or at least about 70, 75, 80, 85, 90, 95, 96, 97, 98, 99, 99.1, 99.2, 99.3, 99.4, 99.5, 99.6, 99.7 99.8, 99.9% or more pure, or any range derivable therein, relative to any contaminating components (w/w or w/v).

In other methods, there may be steps including, but not limited to, obtaining information (qualitative and/or quantitative) about one or more 5-hydroxymethylcytosines in a nucleic acid sample; ordering an assay to determine, identify, and/or map 5-hydroxymethylcytosines in a nucleic acid sample; reporting information (qualitative and/or quantitative) about one or more 5-hydroxymethylcytosines in a nucleic acid sample; comparing that information to information about 5-hydroxymethylcytosines in a control or comparative sample. Unless otherwise stated, the terms "determine," "analyze," "assay," and "evaluate" in the context of a sample refer to transformation of that sample to gather qualitative and/or quantitative data about the sample.

In some embodiments, nucleic acid molecules may be DNA, RNA, or a combination of both. Nucleic acids may be recombinant, genomic, or synthesized. In additional embodiments, methods involve nucleic acid molecules that are isolated and/or purified. The nucleic acid may be isolated from a cell or biological sample in some embodiments. Certain embodiments involve isolating nucleic acids from a eukaryotic, mammalian, or human cell. In some cases, they are isolated from non-nucleic acids. In some embodiments, the nucleic acid molecule is eukaryotic; in some cases, the nucleic acid is mammalian, which may be human. This means the nucleic acid molecule is isolated from a human cell and/or has a sequence that identifies it as human. In particular embodiments, it is contemplated that the nucleic acid molecule is not a prokaryotic nucleic acid, such as a bacterial nucleic acid molecule. In additional embodiments, isolated nucleic acid molecule are on an array. In particular cases, the array is a microarray. In some cases, a nucleic acid is isolated by any technique known to those of skill in the art, including, but not limited to, using a gel, column, matrix or filter to isolate the nucleic acids. In some embodiments, the gel is a polyacrylamide or agarose gel.

Methods and compositions may also include a modified UDP-Glu. In some embodiments, the modified UDP-Glu comprises a modification moiety. In some embodiments, more than one modification moiety is included. The term "modification moiety" refers to a chemical compound or element that is added to a UDP-Glu molecule. A modified UDP-Glu refers to a UDP-Glu molecule having i) a modification moiety or ii) a chemical compound or element that is substituted for a molecule in UDP-Glu, such that the resulting modified compound has a different chemical formula than unmodified UDP-Glu. It is specifically contemplated that a modified UDP-Glu does not include a UDP-Glu that is radioactive by substitution of a molecule or compound in a UDP-Glu with the same molecule or compound, for example, a molecule or compound that is merely radioactive. In certain embodiments it is contemplated that a modified UDP-Glu is not employed, but that a UDP-Glu molecule that is unmodified, but that one or more chemicals compounds are a radioactive version of the same molecule.

In certain embodiments, modified UDP-Glu or a modification moiety may comprise one or more detectable moieties. A detectable moiety refers to a chemical compound or element that is capable of being detected. In particular embodiments, a modified UDP-Glu is not a version of UDP-Glu that is radioactive, and in specific embodiments, a modified UDP-Glu does not have a radioactive carbon molecule. In certain embodiments, a detectable moiety is fluorescent, radioactive, enzymatic, electrochemical, or colorimetric. In some embodiments, the detectable moiety is a fluorophore or quantum dot. In particular embodiments, FRET may be employed to detect glycosylated nucleotides.

In some embodiments, a modification moiety may be a linker that allows one or more functional or detectable moieties or isolation tags to be attached to the glycosylated 5-hmC molecules. In some embodiments the linker is an azide linker or a thiol linker. In further embodiments, the modification moiety may be an isolation tag, which means the tag can be used to isolate a molecule that is attached to the tag. In certain embodiments, the isolation tag is biotin or a histidine tag. In some cases, the tag is modified, such as with a detectable moiety. It is contemplated that the linker allows for other chemical compounds or substances to be attached to the glycosylated nucleic acid at 5-hmC. In some embodiments, a functional moieties is attached to the modified UDP-Glu molecule, which is then used to glycosylate 5-hmC nucleotides. In other embodiments, a function moiety is attached to the modified glucose after 5-hmC nucleotides have been glycosylation. In certain embodiments one or more functional and/or detectable moieties and/or isolation tags are attached to each 5-hmC nucleotides.

In further embodiments, a functional moiety comprises a molecule or compound that inhibits or blocks an enzyme from using the glycosylated 5-hydroxymethylcytosine in the nucleic acid molecule as a substrate. In some embodiments, the inhibition is sufficiently complete to prevent detection of an enzymatic reaction involving the glycosylated 5-hydroxymethylcytosine. It is contemplated that the molecule or compound that blocks an enzyme may be doing this by sterically blocking access of the enzyme. Such sterical blocking moieties are specifically contemplated as modification moieties. In specific embodiments, the sterical blocking moieties contain 1, 2, or 3 ringed structures, including but not limited to aromatic ring structures. In certain embodiments the blocking moiety is polyethylene glycol. In other embodiments, it is a nucleic acid, amino acid, carbohydrate, or fatty acid (including mono-, di-, or tri-versions).

Methods and compositions may also involve one or more enzymes in addition to β-glucosyltransferase. In some embodiments, the enzyme is a restriction enzyme or a polymerase. In certain cases, embodiments involve a restriction enzyme. The restriction enzyme may be methylation-insensitive. In other embodiments, the enzyme is polymerase. In certain embodiments, nucleic acids are contacted with a restriction enzyme prior to, concurrent with, or subsequent to glycosylation of nucleic acids with a modified UDP-Glu. The glycosylated nucleic acid may be contacted with a polymerase before or after the nucleic acid has been exposed to a restriction enzyme.

Methods and compositions involve distinguishing between 5-hydroxymethylcytosine and methylcytosine after modifying the 5-hydroxymethylcytosines and not the methylcytosines. Methods may involve identifying 5-hydroxymethylcytosines in the nucleic acids by comparing glycosylated nucleic acids with unglycosylated nucleic acids or to nucleic acids whose glycosylation state is already known. Detection of the modification can involve a wide variety of recombinant nucleic acid techniques. In some embodiments, a glycosylated nucleic acid molecule is incubated with polymerase, at least one primer, and one or more nucleotides under conditions to allow polymerization of the glycosylated nucleic acid. In additional embodiments, methods may involve sequencing a glycosylated nucleic acid molecule. In other embodiments, a glycosylated nucleic acid is used in a primer extension assay.

Methods and compositions may involve a control nucleic acid. The control may be used to evaluate whether glycosylation or other enzymatic reactions are occurring. Alternatively, the control may be used to compare glycosylation states. The control may be a negative control or it may be a positive control. It may be a control that was not incubated with one or more reagents in the glycosylation reaction. Alternatively, a control nucleic acid may be a reference nucleic acid, which means its glycosylation state (based on qualitative and/or quantitative information related to glycosylation at 5-hydroxymethylcytosines, or the absence thereof) is used for comparing to a nucleic acid being evaluated. In some embodiments, multiple nucleic acids from different sources provides the basis for a control nucleic acid. Moreover, in some cases, the control nucleic acid is from a normal sample with respect to a particular attribute, such as a disease or condition, or other phenotype. In some embodiments, the control sample is from a different patient population, a different cell type or organ type, a different disease state, a different phase or severity of a disease state, a different prognosis, a different developmental stage, etc.

In particular embodiments, there are methods for distinguishing 5-hydroxymethylcytosine from 5-methylcytosine in a nucleic acid molecule comprising incubating the nucleic acid molecule with β-glucosyltransferase and a modified uridine diphosphoglucose (UDP-Glu) molecule to glycosylate 5-hydroxymethylcytosines in the nucleic acid molecule with a modified glucose molecule.

Other methods concern modifying a nucleic acid molecule containing at least one 5-hydroxymethylcytosine comprising incubating the nucleic acid molecule with β-glucosyltransferase and a modified uridine diphosphoglucose (UDP-Glu) molecule to glycosylate 5-hydroxymethylcytosines in the nucleic acid molecule with the modified Glu molecule.

Particular embodiments involve identifying 5-hydroxymethylcytosines in genomic DNA comprising: a) isolating the genomic DNA; b) shearing or cutting the genomic DNA into pieces; c) mixing the genomic DNA pieces with β-glucosyltransferase and a modified uridine diphosphoglucose (UDP-Glu) molecule under conditions to promote glycosylation of the 5-hydroxymethylcytosines in the genomic DNA with the modified UDP-Glu molecule; and, d) identifying 5-hydroxymethylcytosines in the genomic DNA using the modified UDP-Glu molecule.

In further embodiments, there are methods for identifying 5-hydroxymethylcytosines in a nucleic acid molecule comprising: a) mixing the nucleic acid molecule with β-glucosyltransferase and a modified uridine diphosphoglucose (UDP-Glu) molecule under conditions to promote glycosylation of the 5-hydroxymethylcytosines in the nucleic acid with the modified UDP-Glu molecule; b) mixing the glycosylated nucleic acid with a methylation-insensitive restriction enzyme, wherein the modified UDP-Glu molecule comprises a molecule or compounds that prevents cleavage of the nucleic acid molecule at a site that would have been cleaved if nucleic acid molecule had not been glycosylated with the modified UDP-Glu; and, c) identifying 5-hydroxymethylcytosines in the genomic DNA using the modified UDP-Glu molecule.

Embodiments may involve methods for mapping 5-hydroxymethylcytosine in a nucleic acid molecule comprising incubating the nucleic acid molecule with β-glucosyltransferase and a modified uridine diphosphoglucose (UDP-Glu) molecule to glycosylate 5-hydroxymethylcytosines in the nucleic acid molecule with the modified UDP-Glu molecule; and mapping the 5-hydroxymethylcytosines in the nucleic acid molecule. As discussed above, the 5-hydroxymethylcytosines in the nucleic acid may be mapped by a number of ways, including being mapped by sequencing the glycosylated nucleic acid and comparing the results to a control nucleic acid or by subjecting the glycosylated nucleic acid to a primer extension assay and comparing the results to a control nucleic acid. In some embodiments, 5-hydroxymethylcytosines in the nucleic acid are mapped by subjecting the glycosylated nucleic acid to a hybridization assay and comparing the results to a control nucleic acid.

Additional embodiments include methods for obtaining information about the presence and/or absence of 5-hydroxymethylcytosine in nucleic acids in a first sample from a subject comprising: a) retrieving a first sample comprising nucleic acids from a biological sample; b) obtaining information about the presence and/or absence of 5-hydroxymethylcytosine in nucleic acids in the first sample, wherein the information is obtained by i) incubating the first nucleic acid sample with β-glucosyltransferase and a modified uridine diphosphoglucose (UDP-Glu) molecule, wherein a modified Glu is enzymatically attached to 5-hydroxymethylcytosines in nucleic acid molecules in the first nucleic acid sample; ii) detecting or measuring the 5-hydroxymethylcytosines based on the presence of the modified Glu to determine the 5-hydroxymethylcytosine status of the first nucleic acid sample; and, iii) comparing the 5-hydroxymethylcytosine status of the first nucleic acid sample with the 5-hydroxymethylcytosine status of nucleic acids in the at least second nucleic acid sample. In additional embodiments, instead of a retrieving a first sample, methods concern obtaining a biological sample directly from a patient or extracting nucleic acids from a biological sample. In certain embodiments, the biological sample is from a patient. In further embodiments, the patient is a human patient.

In some embodiments, methods comprise reporting information about the presence or absence of 5-hMC. In certain embodiments, the reporting is done on a document or an electronic version of a document. It is contemplated that in some embodiments, a clinician reports this information.

Embodiments also concern kits, which may be in a suitable container, that can be used to achieve the described methods. In some embodiments, there are kits comprising purified β-glucosyltransferase and one or more modified uridine diphosphoglucose (UDP-Glu) molecule. The molecules may have or involve different types of modifications. In further embodiments, a kit may include one or more buffers, such as buffers for nucleic acids or for reactions involving nucleic acids. Other enzymes may be included in kits in addition to or instead of β-glucosyltransferase. In some embodiments, an enzyme is a polymerase. Kits may also include nucleotides for use with the polymerase. In some cases, a restriction enzyme is included in addition to or instead of a polymerase.

Other embodiments also concern an array or microarray containing nucleic acid molecules that have been modified at the nucleotides that were 5'-hMC.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) The 5-hmC in duplex DNA is modified using a β-glucosyltransferase enzyme (βGT) which covalently links a glucose molecule from UDP-Glucose (UDP-Glu) to the hydroxymethyl-modified base to produce 5-gmC. Functional tagging groups (X) can be installed onto 5-hmC using synthetically modified UDP-Glu. (FIG. 1B) Functional tagging of 5-hmC within nucleic acid molecules, such as with thiol or azide reactive groups, allows for the further covalent attachment of functional groups, such as biotin, that have been developed for use in a myriad of molecular biology techniques.

FIG. 4. High-throughput methods to detect the 5-hmC modification in genomic DNA.

FIGS. 7A-7B. HPLC analysis of the click reaction. (A), Reaction scheme of the click chemistry between compound 1 and the 11-mer synthetic DNA containing N3-5-gmC. (B), HPLC chromatograms (at 260 nm) of the nucleosides derived from the 11-mer N3-5-gmC-containing synthetic DNA before and after the click chemistry. The peak corresponding to N3-5-gmC decreased dramatically after the click chemistry, indicating the reaction yield is over 90%. DNA was digested by Nuclease P1 (Sigma) and Alkaline Phosphatase (Sigma). Samples were analyzed by HPLC with a C18 reverse-phase column equilibrated with buffer A (5 mM ammonium acetate, pH 7.5) and buffer B (5 mM ammonium, 0.01% TFA, 60% $CH_3CN$).

Control regions are two regions that were not identified as 5-hmC peaks in Adult Female relative to P7.

Figure 15:
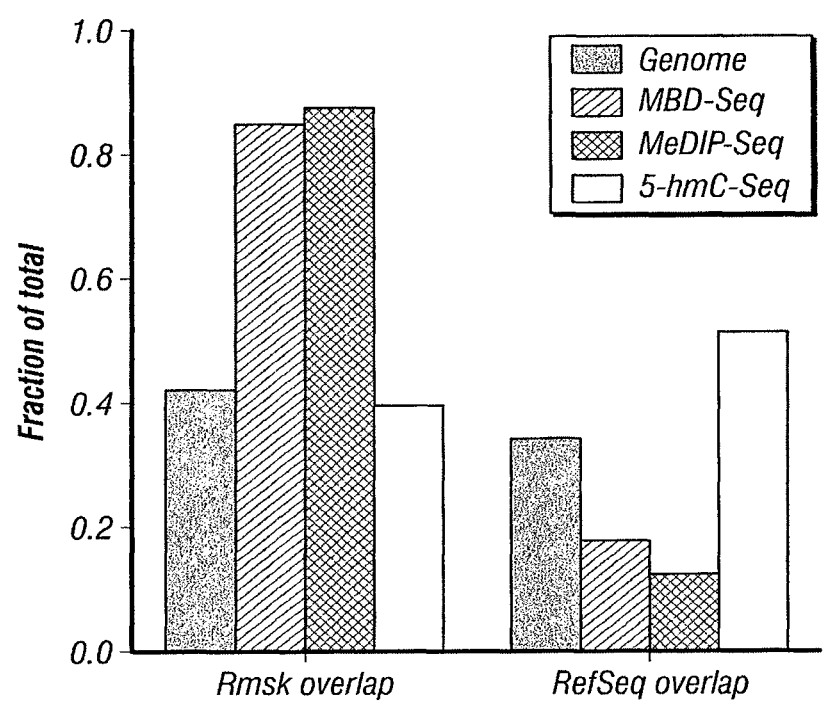

FIG. 15. Percentages of sequencing reads from MBD-Seq, MeDIP-Seq and 5-hmC-Seq mapped to RepeatMasker (Rmsk) and RefSeq. MeDIP-Seq, MBD-Seq, and 5-hmC reads were aligned to the NCBI37, mm9 using identical parameters and identified as RepeatMasker (Rmsk) or RefSeq if overlapping ≥1 bp of a particular annotation. The fraction of total reads corresponding to each was then determined. The expected fraction of reads based on the fraction of genomic sequence corresponding to either Rmsk or RefSeq was also plotted for comparison.

Figure 16:
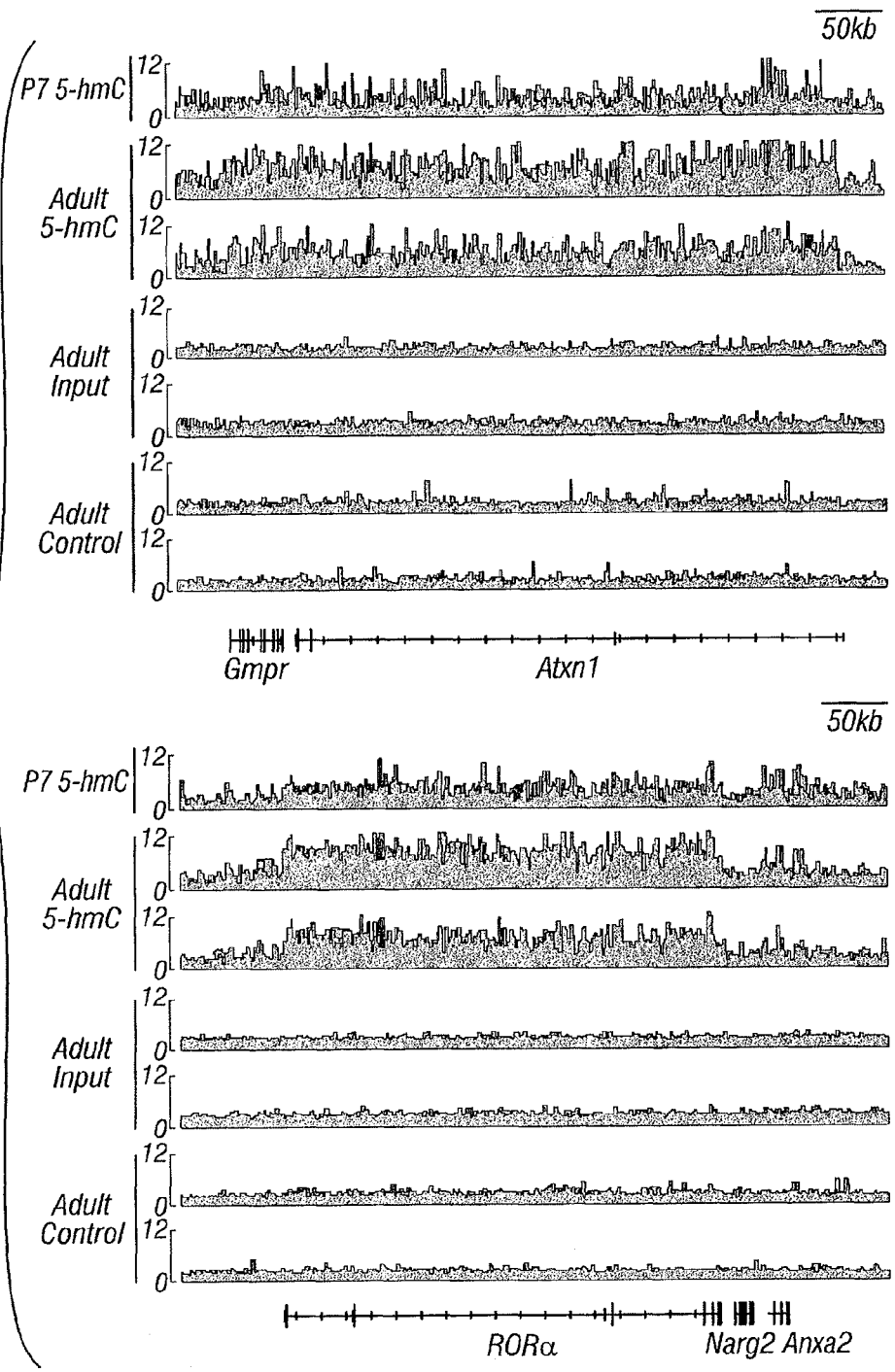

FIG. 16. Examples of intragenic enrichment of 5-hmC at genes that have been linked to ataxia and disorders of Purkinje cell degeneration in mouse and human. Top panel shows Ataxin 1 while bottom panel shows RORα, with pink representing female and blue representing male.

Figure 17:
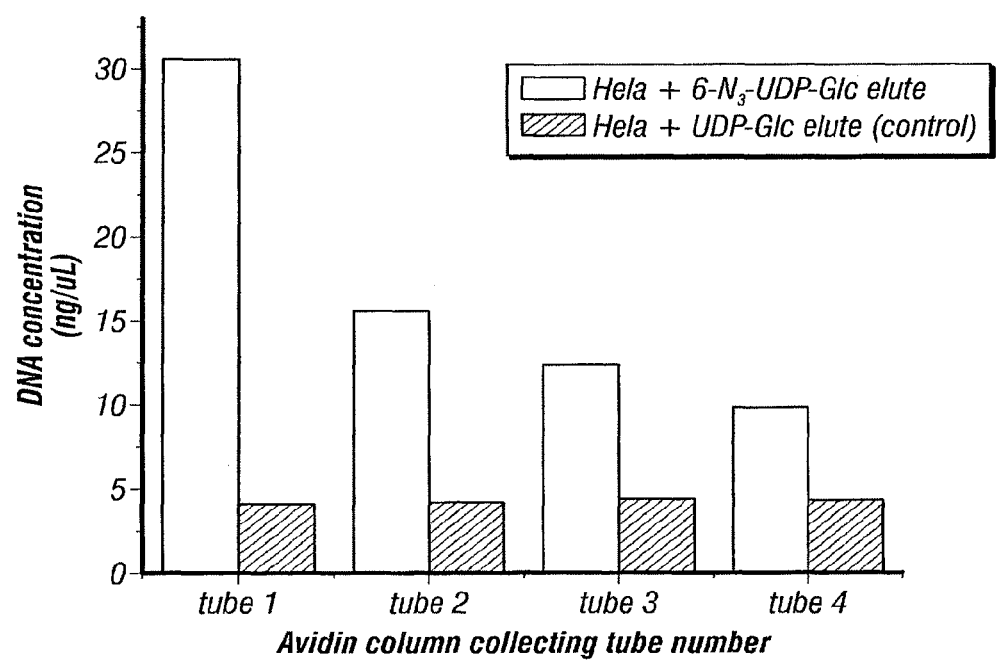

FIG. 17. Genomic DNA was extracted from Hela cells and subsequently sonicated into 100-500 bp fragments. These fragments were divided into two groups, each added either azide-glucose or regular glucose (control group) to potential 5-hmC using β-glucoyltransferase, followed by biotinylation of these fragments using click chemistry. Only the azide-glucose group will be biotinylated, the control group will not. Both groups were then subjected to monomeric-avidin column. After elution, UV showed that only the azide-glucose group had pull-down DNA, the control group did not.

Figure 18:
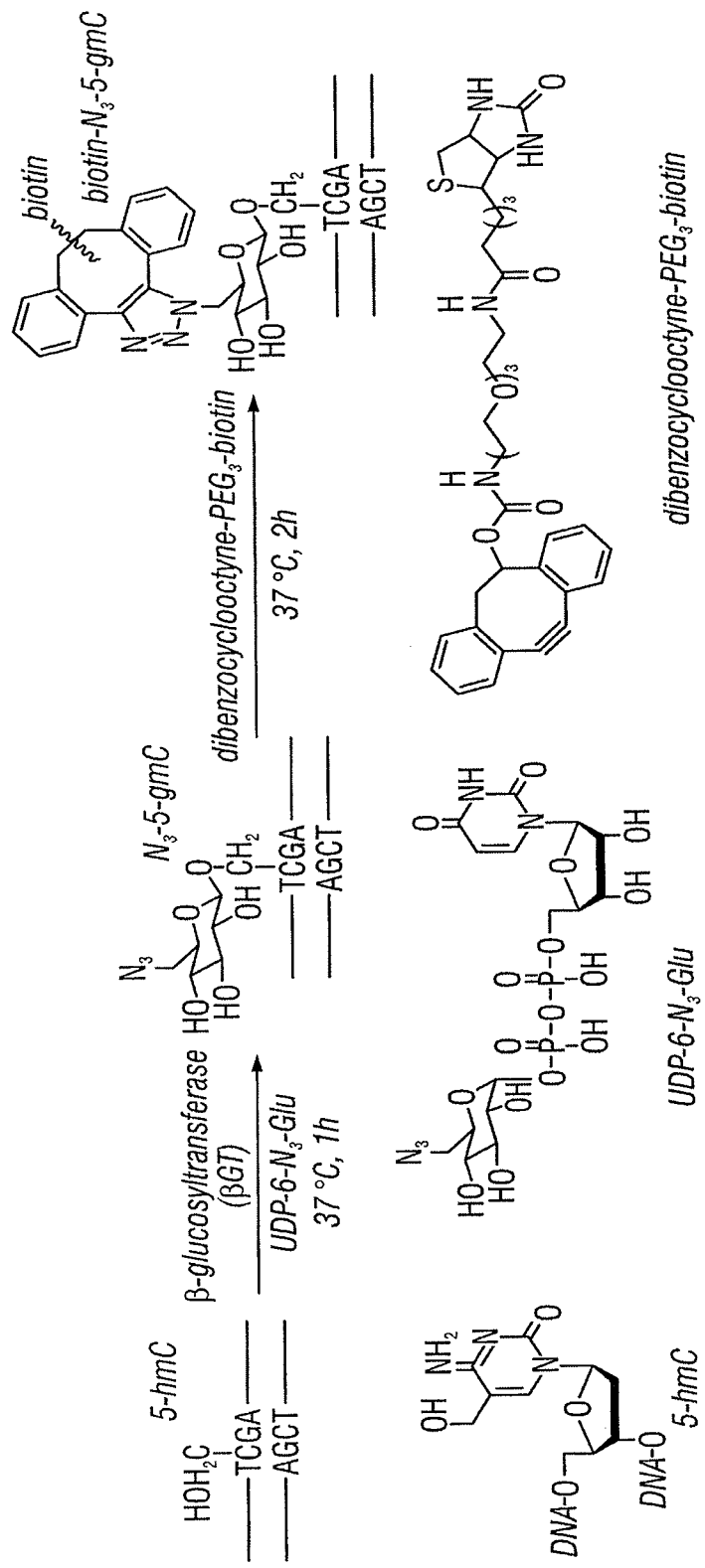

FIG. 18. The βGT-catalyzed formation of $N_3$-5-gmC and the subsequent click chemistry to yield biotin-$N_3$-5-gmC on the TCGA site in duplex DNA. Modification on only one strand is shown.

Figure 19A:
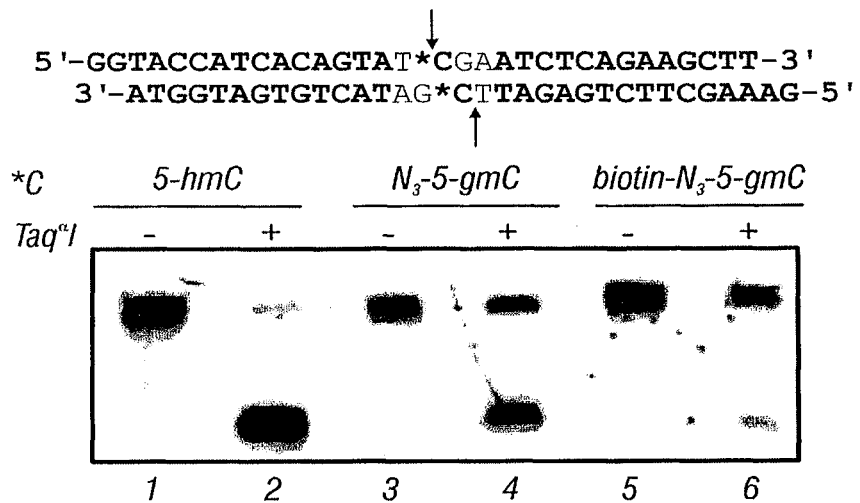
Figure 19B:
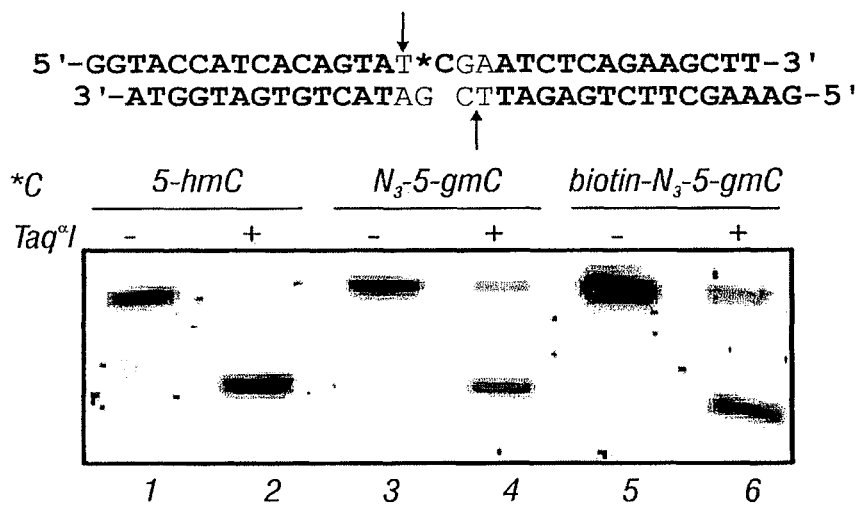

FIGS. 19A-19B. Taq$^{\alpha}$I-mediated digestion of 5-hmC-, $N_3$-5-gmC-, and biotin-$N_3$-5-gmC-containing DNA with the sequences showing on top. *C indicates the modified position; arrows indicate Taq$^{\alpha}$I cutting sites. (A), Digestion of fully-modified DNA. (B), Digestion of hemi-modified DNA. The 32-mer dsDNA (1 pmol) was digested with 100 U of Taq$^{\alpha}$I (New England BioLabs) for 1 hr at 65° C. Samples were analyzed by 16% PAGE/Urea gel and visualized using SYBR Green I staining (Lumiprobe).

Figure 20A:
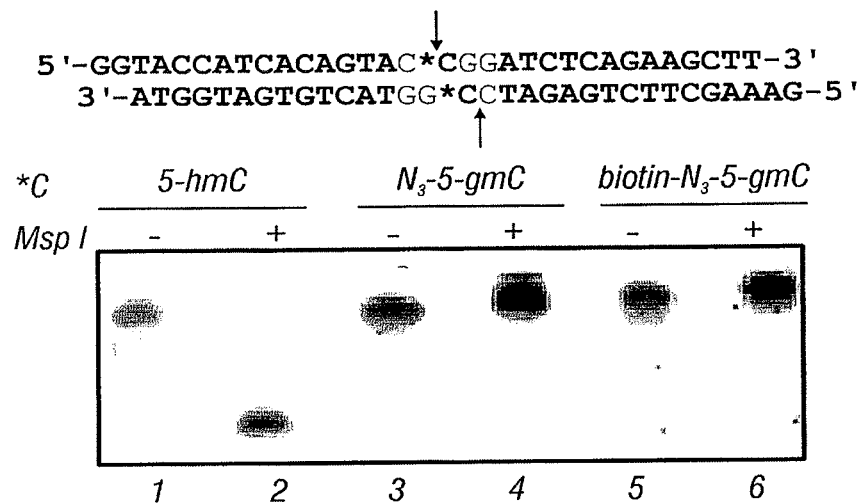
Figure 20B:
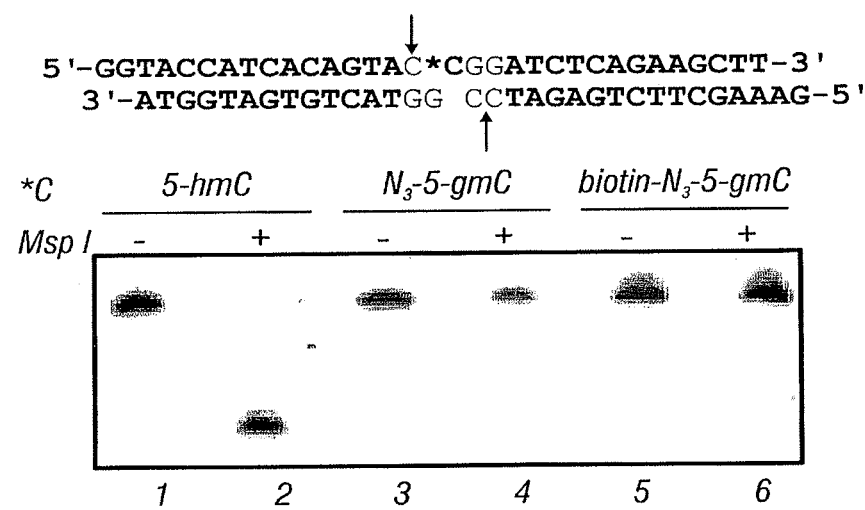

FIGS. 20A-20B. MspI digestion of 5-hmC-, $N_3$-5-gmC-, and biotin-$N_3$-5-gmC-containing DNA with the sequences showing on top. *C indicates the modified position; arrows indicate MspI cutting sites. (A), Digestion of fully-modified DNA. (B), Digestion of hemi-modified DNA. The 32-mer dsDNA (1 pmol) was digested with 100 U of MspI (New England BioLabs) for 1 hr at 37° C. Samples were analyzed by 16% PAGE/Urea gel and visualized using SYBR Green I staining (Lumiprobe).

Figure 21:
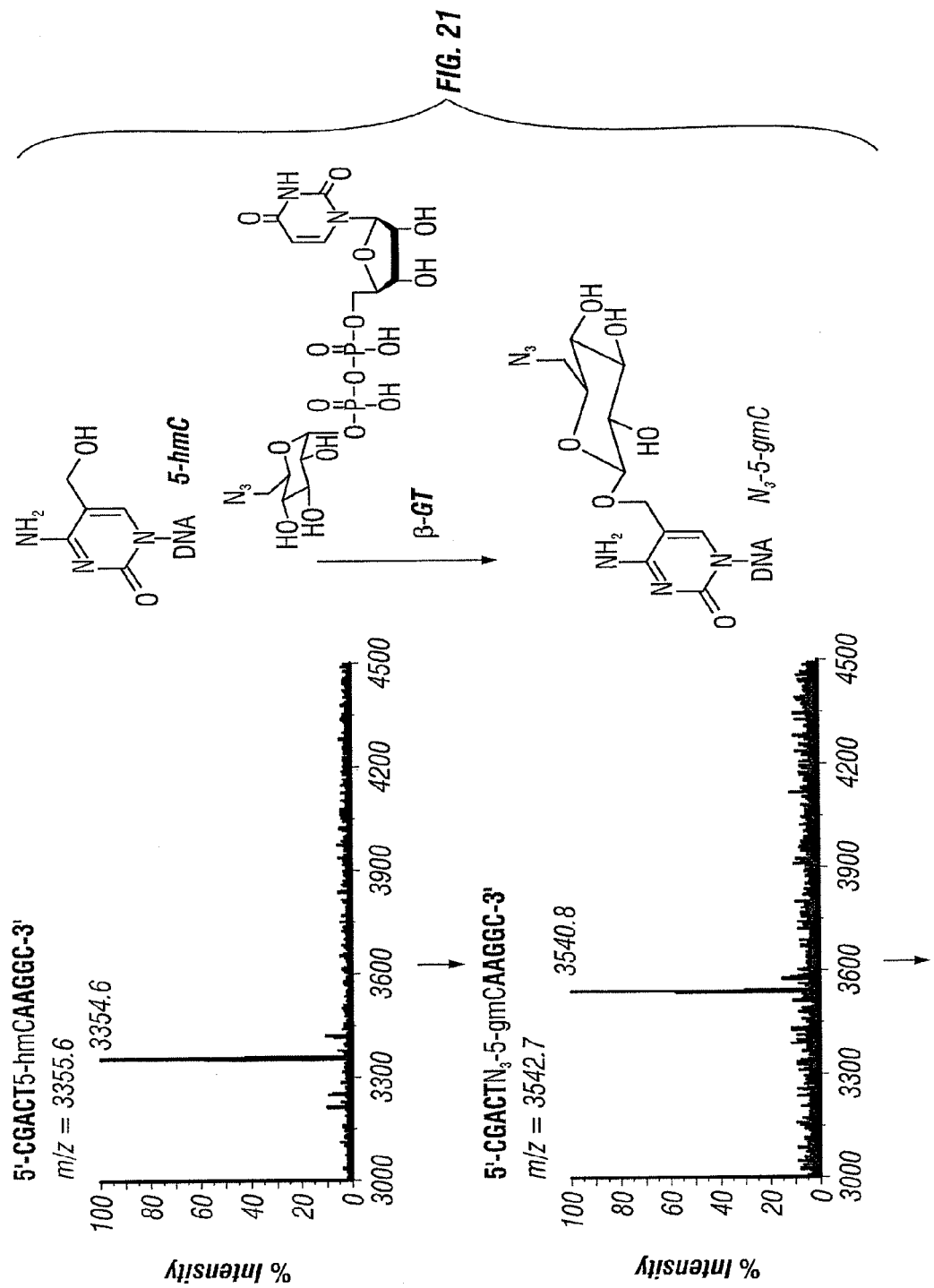
Figure 21:
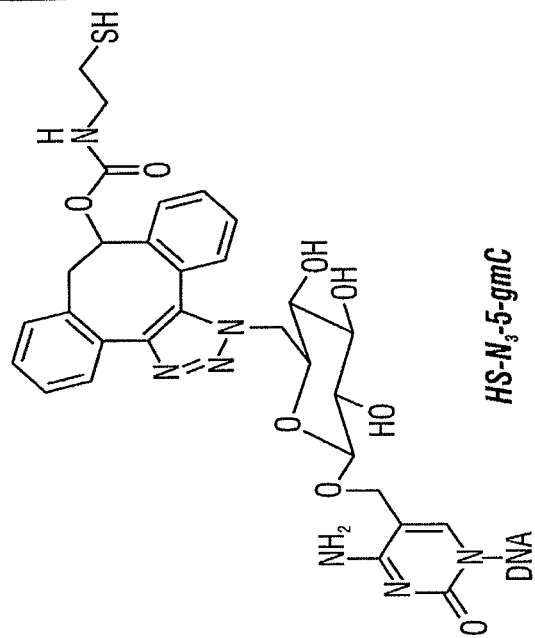
Figure 21:
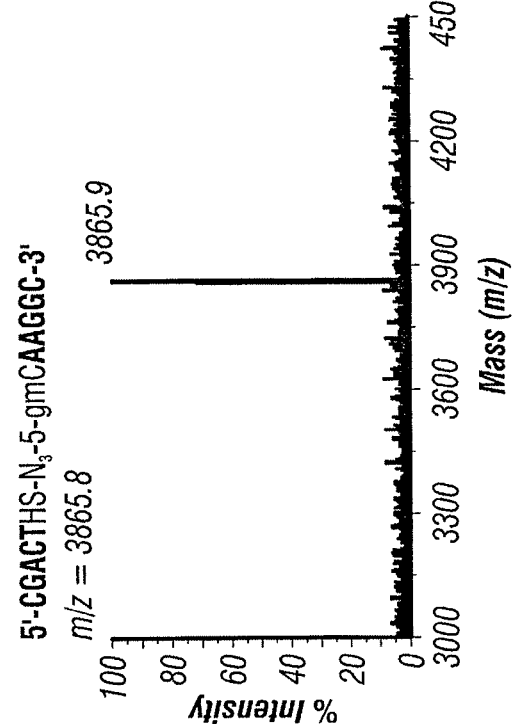

FIG. 21. Shows the development of a cleavable biotin-containing capture agent with a disulfide linker as the click reaction partner to form biotin-S-S-$N_3$-5-gmC.

DETAILED DESCRIPTION OF THE INVENTION

Certain embodiments are directed to methods and compositions for modifying 5-hmC, detecting 5-hmC, and/or evaluating 5-hmC in nucleic acids. In certain aspects, 5-hmC is glycosylated. In a further aspect 5-hmC is coupled to a labeled or modified glucose moiety. Using the methods described herein a large variety of detectable groups (biotin, fluorescent tag, radioactive groups, etc.) can be coupled to 5-hmC via a glucose modification.

Modification of 5-hmC can be performed using the enzyme β-glucosyltransferase (βGT), or a similar enzyme, that catalyzes the transfer of a glucose moiety from uridine diphosphoglucose (UDP-Glu) to the hydroxyl group of 5-hmC, yielding β-glycosyl-5-hydroxymethyl-cytosine (5-gmC). The inventors have found that this enzymatic glycosylation offers a strategy for incorporating modified glucose molecules for labeling or tagging 5-hmC in eukaryotic nucleic acids. For instance, a glucose molecule chemically modified to contain an azide ($N_3$) group may be covalently attached to 5-hmC through this enzyme-catalyzed glycosylation. Thereafter, phosphine-activated reagents, including but not limited to biotin-phosphine, fluorophore-phosphine, and NHS-phosphine, or other affinity tags can be specifically installed onto glycosylated 5-hmC via reactions with the azide.

Chemical tagging can be used to determine the precise locations of 5-hmC in a high throughput manner. The inventors have shown that the 5-gmC modification renders the labeled DNA resistant to restriction enzyme digestion and/or polymerization. In certain aspects, glycosylated and unmodified genomic DNA may be treated with restriction enzymes and subsequently subjected to various sequencing methods to reveal the precise locations of each cytosine modification that hampers the digestion.

The inventors have shown that a functional group (e.g., an azide group) can be incorporated into DNA using methods described herein. This incorporation of a functional group allows further labeling or tagging cytosine residues with biotin and other tags. The labeling or tagging of 5-hmC can use, for example, click chemistry or other functional/coupling groups know to those skilled in the art. The labeled or tagged DNA fragments containing 5-hmC can be isolated and/or evaluated using modified methods being currently used to evaluate 5-mC containing nucleic acids.

Furthermore, methods and compositions of the invention may be used to introduce a sterically bulky group to 5-hmC. The presence of a bulky group on the DNA template strand will interfere with the synthesis of a nucleic acid strand by DNA polymerase or RNA polymerase, or the efficient cleavage of DNA by a restriction endonuclease or inhibition of other enzymatic modifications of nucleic acid containing 5-hmC. As a result, primer extensions or other assays can be employed, for example, to evaluate a partially extended primer of certain length and the modification sites can be revealed by sequencing the partially extended primers. Other approaches taking advantage of this chemical tagging method are also contemplated.

In certain aspects, differential modification of nucleic acid between two or more samples can be evaluated. Studies including heart, liver, lungs, kidney, muscle, testes, spleen, and brain indicate that under normal conditions 5-hmC is predominately in normal brain cells. Additional studies have shown that 5-hmC is also present in mouse embryonic stem cells. The Ten-eleven translocation 1 (TET1) protein has been identified as the catalyst for converting 5-mC to 5-hmC. Studies have shown that TET1 expression is inversely correlated to 5-mC expression. Overexpression of TET1 in cells seems to correlate with increased expression of 5-hmC. Also, TET1 is known to be involved in pediatric and adult acute myeloid leukemia and acute lymphoblastic leukemia. Thus, evaluating and comparing 5-hmC levels can be used in evaluating various disease states and comparing various nucleic acid samples.

I. Modification of 5-hmC

Certain embodiments are directed to methods and compositions for modifying eukaryotic nucleic acids containing 5-hmC. In certain aspects a target nucleic acid is contacted with a β-glucosyltransferase enzyme and a UDP substrate comprising a modified or modifiable glucose moiety.

A. β-glycosyltransferase (βGT)

A glucosyl-DNA beta-glucosyltransferase (EC 2.4.1.28, β-glycosyltransferase (βGT)) is an enzyme that catalyzes the chemical reaction in which a beta-D-glucosyl residue is transferred from UDP-glucose to a glucosylhydroxymethylcytosine residue in a nucleic acid. This enzyme resembles DNA beta-glucosyltransferase in that respect. This enzyme belongs to the family of glycosyltransferases, specifically the hexosyltransferases. The systematic name of this enzyme class is UDP-glucose:D-glucosyl-DNA beta-D-glucosyltransferase. Other names in common use include T6-glucosyl-HMC-beta-glucosyl transferase, T6-beta-glucosyl transferase, uridine diphosphoglucose-glucosyldeoxyribonucleate, and beta-glucosyltransferase.

In certain aspects, the a β-glucosyltransferase is a His-tag fusion protein having the amino acid sequence (βGT begins at amino acid 25(met)):

(SEQ ID NO: 1)
SHHHHHHSSGVDLGTENLYFQSNAMKIAIINMGNNVINFKTVPSS

ETIYLFKVISEMGLNVDIISLKNGVYTKSFDEVDVNDYDRLIVVNSSINF

FGGKPNLAILSAQKFMAKYKSKIYYLFTDIRLPFSQSWPNVKNRPWAYLY

TEEELLIKSPIKVISQGINLDIAKAAHKKVDNVIEFEYFPIEQYKIHMND

FQLSKPTKKTLDVIYGGSFRSGQRESKMVEFLFDTGLNIEFFGNAREKQF

KNPKYPWTKAPVFTGKIPMNMVSEKNSQAIAALIIGDKNYNDNFITLRVW

ETMASDAVMLIDEEFDTKHRIINDARFYVNNRAELIDRVNELKHSDVLRK

EMLSIQHDILNKTRAKKAEWQDAFKKAIDL.

In other embodiments, the protein may be used without the His-tag (hexa-histidine tag shown above) portion. For example, βGT was cloned into the target vector pMCSG19 by Ligation Independent Cloning (LIC) method according to Donnelly et al. (2006). The resulting plasmid was transformed into BL21 star (DE3) competent cells containing pRK1037 (Science Reagents, Inc.) by heat shock. Positive colonies were selected with 150 μg/ml Ampicillin and 30 μg/ml Kanamycin. One liter of cells was grown at 37° C. from a 1:100 dilution of an overnight culture. The cells were induced with 1 mM of IPTG when OD600 reaches 0.6-0.8. After overnight growth at 16° C. with shaking, the cells were collected by centrifugation, suspended in 30 mL Ni-NTA buffer A (20 mM Tris-HCl pH 7.5, 150 mM NaCl, 30 mM imidazole, and 10 mM β-ME) with protease inhibitor PMSF. After loading to a Ni-NTA column, proteins were eluted with a 0-100% gradient of Ni-NTA buffer B (20 mM Tris-HCl pH 7.5, 150 mM NaCl, 400 mM imidazole, and 10 mM β-ME). βGT-containing fractions were further purified by MonoS (Buffer A: 10 mM Tris-HCl pH 7.5; Buffer B: 10 mM Tris-HCl pH 7.5, and 1M NaCl) to remove DNA. Finally, the collected protein fractions were loaded onto a Superdex 200 (GE) gel-filtration column equilibrated with 50 mM Tris-HCl pH 7.5, 20 mM $MgCl_2$, and 10 mM β-ME. SDS-PAGE gel revealed a high degree of purity of βGT. βGT was concentrated to 45 μM and stored frozen at −80° C. with an addition of 30% glycerol.

A variety of proteins can be purified using methods known in the art. Protein purification is a series of processes intended to isolate a single type of protein from a complex mixture. Protein purification is vital for the characterization of the function, structure and interactions of the protein of interest. The starting material is usually a biological tissue or a microbial culture. The various steps in the purification process may free the protein from a matrix that confines it, separate the protein and non-protein parts of the mixture, and finally separate the desired protein from all other proteins. Separation of one protein from all others is typically the most laborious aspect of protein purification. Separation steps exploit differences in protein size, physico-chemical properties and binding affinity.

Evaluating Purification Yield.

The most general method to monitor the purification process is by running a SDS-PAGE of the different steps. This method only gives a rough measure of the amounts of different proteins in the mixture, and it is not able to distinguish between proteins with similar molecular weight. If the protein has a distinguishing spectroscopic feature or an enzymatic activity, this property can be used to detect and quantify the specific protein, and thus to select the fractions of the separation, that contains the protein. If antibodies against the protein are available then western blotting and ELISA can specifically detect and quantify the amount of desired protein. Some proteins function as receptors and can be detected during purification steps by a ligand binding assay, often using a radioactive ligand.

In order to evaluate the process of multistep purification, the amount of the specific protein has to be compared to the amount of total protein. The latter can be determined by the Bradford total protein assay or by absorbance of light at 280 nm, however some reagents used during the purification process may interfere with the quantification. For example, imidazole (commonly used for purification of polyhistidine-tagged recombinant proteins) is an amino acid analogue and at low concentrations will interfere with the bicinchoninic acid (BCA) assay for total protein quantification. Impurities in low-grade imidazole will also absorb at 280 nm, resulting in an inaccurate reading of protein concentration from UV absorbance.

Another method to be considered is Surface Plasmon Resonance (SPR). SPR can detect binding of label free molecules on the surface of a chip. If the desired protein is an antibody, binding can be translated to directly to the activity of the protein. One can express the active concentration of the protein as the percent of the total protein. SPR can be a powerful method for quickly determining protein activity and overall yield. It is a powerful technology that requires an instrument to perform.

Methods of Protein Purification.

The methods used in protein purification can roughly be divided into analytical and preparative methods. The distinction is not exact, but the deciding factor is the amount of protein that can practically be purified with that method. Analytical methods aim to detect and identify a protein in a mixture, whereas preparative methods aim to produce large quantities of the protein for other purposes, such as structural biology or industrial use.

Depending on the source, the protein has to be brought into solution by breaking the tissue or cells containing it. There are several methods to achieve this: Repeated freezing and thawing, sonication, homogenization by high pressure, filtration (either via cellulose-based depth filters or cross-flow filtration), or permeabilization by organic solvents. The method of choice depends on how fragile the protein is and how sturdy the cells are. After this extraction process soluble proteins will be in the solvent, and can be separated from cell membranes, DNA etc. by centrifugation. The extraction process also extracts proteases, which will start digesting the proteins in the solution. If the protein is sensitive to proteolysis, it is usually desirable to proceed quickly, and keep the extract cooled, to slow down proteolysis.

In bulk protein purification, a common first step to isolate proteins is precipitation with ammonium sulfate $(NH_4)_2SO_4$. This is performed by adding increasing amounts of ammonium sulfate and collecting the different fractions of precipitate protein. One advantage of this method is that it can be performed inexpensively with very large volumes.

The first proteins to be purified are water-soluble proteins. Purification of integral membrane proteins requires disruption of the cell membrane in order to isolate any one particular protein from others that are in the same membrane compartment. Sometimes a particular membrane fraction can be isolated first, such as isolating mitochondria from cells before purifying a protein located in a mitochondrial membrane. A detergent such as sodium dodecyl sulfate (SDS) can be used to dissolve cell membranes and keep membrane proteins in solution during purification; however, because SDS causes denaturation, milder detergents such as TRITON X-100 (2-ethanediyl),α-(4-(1,1,3,3-tetramethylbutyl)phenyl)-ω-hydroxy-poly(oxy-1)) or CHAPS (3-[(3-cholamidopropyl) dimethylammonio]-1-propanesulfonate) be used to retain the protein's native conformation during complete purification.

Centrifugation is a process that uses centrifugal force to separate mixtures of particles of varying masses or densities suspended in a liquid. When a vessel (typically a tube or bottle) containing a mixture of proteins or other particulate matter, such as bacterial cells, is rotated at high speeds, the angular momentum yields an outward force to each particle that is proportional to its mass. The tendency of a given particle to move through the liquid because of this force is offset by the resistance the liquid exerts on the particle. The net effect of "spinning" the sample in a centrifuge is that massive, small, and dense particles move outward faster than less massive particles or particles with more "drag" in the liquid. When suspensions of particles are "spun" in a centrifuge, a "pellet" may form at the bottom of the vessel that is enriched for the most massive particles with low drag in the liquid. Non-compacted particles still remaining mostly in the liquid are called the "supernatant" and can be removed from the vessel to separate the supernatant from the pellet. The rate of centrifugation is specified by the angular acceleration applied to the sample, typically measured in comparison to the g. If samples are centrifuged long enough, the particles in the vessel will reach equilibrium wherein the particles accumulate specifically at a point in the vessel where their buoyant density is balanced with centrifugal force. Such an "equilibrium" centrifugation can allow extensive purification of a given particle.

Sucrose gradient centrifugation is a linear concentration gradient of sugar (typically sucrose, glycerol, or a silica based density gradient media, like Percoll™) is generated in a tube such that the highest concentration is on the bottom and lowest on top. A protein sample is then layered on top of the gradient and spun at high speeds in an ultracentrifuge. This causes heavy macromolecules to migrate towards the bottom of the tube faster than lighter material. After separating the protein/particles, the gradient is then fractionated and collected.

Usually a protein purification protocol contains one or more chromatographic steps. The basic procedure in chromatography is to flow the solution containing the protein through a column packed with various materials. Different proteins interact differently with the column material, and can thus be separated by the time required to pass the column, or the conditions required to elute the protein from the column. Usually proteins are detected as they are coming off the column by their absorbance at 280 nm. Many different chromatographic methods exist:

Chromatography can be used to separate protein in solution or denaturing conditions by using porous gels. This technique is known as size exclusion chromatography. The principle is that smaller molecules have to traverse a larger volume in a porous matrix. Consequentially, proteins of a certain range in size will require a variable volume of eluent (solvent) before being collected at the other end of the column of gel.

In the context of protein purification, the eluant is usually pooled in different test tubes. All test tubes containing no measurable trace of the protein to purify are discarded. The remaining solution is thus made of the protein to purify and any other similarly-sized proteins.

Ion exchange chromatography separates compounds according to the nature and degree of their ionic charge. The column to be used is selected according to its type and strength of charge. Anion exchange resins have a positive charge and are used to retain and separate negatively charged compounds, while cation exchange resins have a negative charge and are used to separate positively charged molecules. Before the separation begins a buffer is pumped through the column to equilibrate the opposing charged ions. Upon injection of the sample, solute molecules will exchange with the buffer ions as each competes for the binding sites on the resin. The length of retention for each solute depends upon the strength of its charge. The most weakly charged compounds will elute first, followed by those with successively stronger charges. Because of the nature of the separating mechanism, pH, buffer type, buffer concentration, and temperature all play important roles in controlling the separation.

Affinity Chromatography is a separation technique based upon molecular conformation, which frequently utilizes application specific resins. These resins have ligands attached to their surfaces which are specific for the compounds to be separated. Most frequently, these ligands function in a fashion similar to that of antibody-antigen interactions. This "lock and key" fit between the ligand and its target compound makes it highly specific, frequently generating a single peak, while all else in the sample is unretained.

Many membrane proteins are glycoproteins and can be purified by lectin affinity chromatography. Detergent-solubilized proteins can be allowed to bind to a chromatography resin that has been modified to have a covalently attached lectin. Proteins that do not bind to the lectin are washed away and then specifically bound glycoproteins can be eluted by adding a high concentration of a sugar that competes with the bound glycoproteins at the lectin binding site. Some lectins have high affinity binding to oligosaccharides of glycoproteins that is hard to compete with sugars, and bound glycoproteins need to be released by denaturing the lectin.

A common technique involves engineering a sequence of 6 to 8 histidines into the N- or C-terminal of the protein. The polyhistidine binds strongly to divalent metal ions such as nickel and cobalt. The protein can be passed through a column containing immobilized nickel ions, which binds the polyhistidine tag. All untagged proteins pass through the column. The protein can be eluted with imidazole, which competes with the polyhistidine tag for binding to the column, or by a decrease in pH (typically to 4.5), which decreases the affinity of the tag for the resin. While this procedure is generally used for the purification of recombinant proteins with an engineered affinity tag (such as a 6×His tag or Clontech's HAT tag), it can also be used for natural proteins with an inherent affinity for divalent cations.

Immunoaffinity chromatography uses the specific binding of an antibody to the target protein to selectively purify the protein. The procedure involves immobilizing an antibody to a column material, which then selectively binds the protein, while everything else flows through. The protein can be eluted by changing the pH or the salinity. Because this method does not involve engineering in a tag, it can be used for proteins from natural sources.

Another way to tag proteins is to engineer an antigen peptide tag onto the protein, and then purify the protein on a column or by incubating with a loose resin that is coated with an immobilized antibody. This particular procedure is known as immunoprecipitation. Immunoprecipitation is quite capable of generating an extremely specific interaction which usually results in binding only the desired protein. The purified tagged proteins can then easily be separated from the other proteins in solution and later eluted back into clean solution. Tags can be cleaved by use of a protease. This often involves engineering a protease cleavage site between the tag and the protein.

High performance liquid chromatography or high pressure liquid chromatography is a form of chromatography applying high pressure to drive the solutes through the column faster. This means that the diffusion is limited and the resolution is improved. The most common form is "reversed phase" hplc, where the column material is hydrophobic. The proteins are eluted by a gradient of increasing amounts of an organic solvent, such as acetonitrile. The proteins elute according to their hydrophobicity. After purification by HPLC the protein is in a solution that only contains volatile compounds, and can easily be lyophilized. HPLC purification frequently results in denaturation of the purified proteins and is thus not applicable to proteins that do not spontaneously refold.

At the end of a protein purification, the protein often has to be concentrated. Different methods exist. If the solution doesn't contain any other soluble component than the protein in question the protein can be lyophilized (dried). This is commonly done after an HPLC run. This simply removes all volatile component leaving the proteins behind.

Ultrafiltration concentrates a protein solution using selective permeable membranes. The function of the membrane is to let the water and small molecules pass through while retaining the protein. The solution is forced against the membrane by mechanical pump or gas pressure or centrifugation.

Gel electrophoresis is a common laboratory technique that can be used both as preparative and analytical method. The principle of electrophoresis relies on the movement of a charged ion in an electric field. In practice, the proteins are denatured in a solution containing a detergent (SDS). In these conditions, the proteins are unfolded and coated with negatively charged detergent molecules. The proteins in SDS-PAGE are separated on the sole basis of their size.

In analytical methods, the protein migrate as bands based on size. Each band can be detected using stains such as Coomassie blue dye or silver stain. Preparative methods to purify large amounts of protein, require the extraction of the protein from the electrophoretic gel. This extraction may involve excision of the gel containing a band, or eluting the band directly off the gel as it runs off the end of the gel.

In the context of a purification strategy, denaturing condition electrophoresis provides an improved resolution over size exclusion chromatography, but does not scale to large quantity of proteins in a sample as well as the late chromatography columns.

B. Modified Glucose Molecule

A functionalized or labeled glucose molecule can be used in conjunction with βGT to modify 5-hmC in a nucleic polymer such as DNA or RNA.

In certain aspects, the βGT UDP substrate comprises a functionalized or labeled glucose moiety. In a further aspect, the glucose moiety can be modified or functionalized using click chemistry or other coupling chemistries known in the art. Click chemistry is a chemical philosophy introduced by K. Barry Sharpless in 2001 (Kolb et al., 2001; Evans, 2007) and describes chemistry tailored to generate substances quickly and reliably by joining small units.

The label can be any label that is detected, or is capable of being detected. Examples of suitable labels include, e.g., chromogenic label, a radiolabel, a fluorescent label, and a biotinylated label. Thus, the label can be, e.g., fluorescent glucose, biotin-labeled glucose, radiolabeled glucose and the like. In certain aspects, the label is a chromogenic label. The term "chromogenic label" includes all agents that have a distinct color or otherwise detectable marker. In addition to chemical structures having intrinsic, readily-observable colors in the visible range, other markers used include fluorescent groups, biotin tags, enzymes (that may be used in a reaction that results in the formation of a colored product), magnetic and isotopic markers, and so on. The foregoing list of detectable markers is for illustrative purposes only, and is in no way intended to be limiting or exhaustive.

The label may be attached to the agent using methods known in the art. Labels include any detectable group attached to the glucose molecule, or detection agent that does not interfere with its function. Further labels that may be used include fluorescent labels, such as Fluorescein, TEXAS RED (sulforhodamine 101 acid chloride), Lucifer Yellow, Rhodamine, Nile-red (NILE BLUE oxazone), tetramethylrhodamine-5-isothiocyanate, 1,6-diphenyl-1,3,5-hexatriene, cis-Parinaric acid, Phycoerythrin, Allophycocyanin, 4',6-diamidino-2-phenylindole (DAPI), HOECHST 33258 (2'-(4-hydroxyphenyl)-5-(4-methyl-1-piperazinyl)-2,5'-bi-1H-benzimidazole trihydrochloride hydrate), 2-aminobenzamide, and the like. Further labels include electron dense metals, such as gold, ligands, haptens, such as biotin, radioactive labels.

A fluorophore contains or is a functional group that will absorb energy of a specific wavelength and re-emit energy at a different (but equally specific) wavelength. The amount and wavelength of the emitted energy depend on both the fluorophore and the chemical environment of the fluorophore. Fluorophores can be attached to protein using functional groups and or linkers, such as amino groups (Active ester, Carboxylate, Isothiocyanate, hydrazine); carboxyl groups (carbodiimide); thiol (maleimide, acetyl bromide); azide (via click chemistry or non-specifically (glutaraldehyde).

Fluorophores can be proteins, quantum dots (fluorescent semiconductor nanoparticles), or small molecules. Common dye families include, but are not limited to Xanthene derivatives: fluorescein, rhodamine, OREGON GREEN (2',7'-difluorofluorescein), eosin, TEXAS RED, etc.; Cyanine derivatives: cyanine, indocarbocyanine, oxacarbocyanine, thiacarbocyanine and merocyanine; Naphthalene derivatives (dansyl and prodan derivatives); Coumarin derivatives; oxadiazole derivatives: pyridyloxazole, nitrobenzoxadiazole and benzoxadiazole; Pyrene derivatives: cascade blue etc.; BODIPY (Invitrogen); Oxazine derivatives: Nile red, Nile blue, cresyl violet, oxazine 170 etc.; Acridine derivatives: proflavin, acridine orange, acridine yellow etc.; Arylmethine derivatives: auramine, crystal violet, malachite green; CF dye (Biotium); ALEXA FLUOR (Invitrogen); ATTO and TRACY (Sigma Aldrich); FLUOPROBES (Interchim); Tetrapyrrole derivatives: porphin, phtalocyanine, bilirubin; cascade yellow; azure B; acridine orange; DAPI; HOECHST 33258; lucifer yellow; piroxicam; quinine and anthraqinone; squarylium; oligophenylenes; and the like.

Other fluorophores include: Hydroxycoumarin; Aminocoumarin; Methoxycoumarin; CASCADE BLUE ([4-[(4-diethylaminophenyl)-(4-ethylaminonaphthalen-2-yl)methylidene]-1-cyclohexa-2,5-dienylidene]-diethyl-azanium) Pacific Blue; Pacific Orange; Lucifer yellow; NBD (nitrobenzoxadiazole); R-Phycoerythrin (PE); PE-Cy5 conjugates; PE-Cy7 conjugates; Red 613 (PE-TEXAS RED; or conjugate of TEXAS RED with R-phycoerythrin); PerCP (Peridinin chlorophyll); TruRed (PerCP-Cy5.5 conjugate); Fluor X; Fluorescein; BODIPY-FL (4,4-difluoro-4-bora-3a,4adiazas-indacene conjugate substitute for fluoroscein); TRITC (isothiocyanate derivative of rhodamine); X-Rhodamine; Lissamine Rhodamine B; TEXAS RED; Allophycocyanin; APC-Cy7 conjugates.

ALEXA FLUOR dyes (Molecular Probes) include: ALEXA FLUOR 350, ALEXA FLUOR 405, ALEXA FLUOR 430, ALEXA FLUOR 488, ALEXA FLUOR 500, ALEXA FLUOR 514, ALEXA FLUOR 532, ALEXA FLUOR 546, ALEXA FLUOR 555, ALEXA FLUOR 568, ALEXA FLUOR 594, ALEXA FLUOR 610, ALEXA FLUOR 633, ALEXA FLUOR 647, ALEXA FLUOR 660, ALEXA FLUOR 680, ALEXA FLUOR 700, ALEXA FLUOR 750, and ALEXA FLUOR 790.

Cy Dyes (GE Heathcare) include Cyt, Cy3, Cy3B, Cy3.5, Cy5, Cy5.5 and Cy7.

Nucleic acid probes include HOECHST 33342 (2'-(4-ethoxyphenyl)-5-(4-methyl-1-piperazinyl)-2,5-bi(1H-benzimidazole), DAPI, HOECHST 33258, SYTOX Blue, ChromomycinA3, Mithramycin, YOYO-1 (2-([1-(3-[[3-(dimethyl (3-[4-[(E)-(3-methyl-1,3-benzoxazol-3-ium-2-yl) methylidene]-1(4H)-quinolinyl]propyl)ammonio)propyl] diethyl)ammonio]propyl)-4(1H)-quinolinylidene]methyl)-3-methyl-1,3-benzoxazol-3-ium tetraiodide), Ethidium Bromide, Acridine Orange, SYTOX Green, TOTO-1 (thiazole orange dye), TO-PRO-1 (quinolinium, 4-[(3-methyl-2 (3H)-benzothiazolylidene)methyl]-1-[3-(trimethylammonio)propyl]-, diiodide), TO-PRO: Cyanine Monomer, Thiazole Orange, Propidium Iodide (PI), LDS 751, Styryl 8,7-AAD, SYTOX Orange, TOTO-3 (quinolinium, 1,1'-[1,3-propanediylbis[(dimethyliminio)-3,1-propanediyl]]bis[4-[3-(3-methyl-2(3H)-benzothiazolylidene)-1-propenyl]-, tetraiodide), TO-PRO-3 (quinolinium, 4-[3-(3-methyl-2(3H)-benzothiazolylidene)-1-propenyl]-1-[3-(trimethylammonio) propyl]-, diiodide), and DRAQ5.

Cell function probes include Indo-1, Fluo-3, DCFH, DHR, SNARF.

Fluorescent proteins include Y66H, Y66F, EBFP, EBFP2, Azurite, GFPuv, T-Sapphire, Cerulean, mCFP, ECFP, CyPet, Y66W, mKeima-Red, TagCFP, AmCyan1, mTFP1, S65A, Midoriishi Cyan, Wild Type GFP, S65C, TurboGFP, TagGFP, S65L, Emerald, S65T (Invitrogen), EGFP (Clontech), Azami Green (MBL), ZsGreen1 (Clontech), TagYFP (Evrogen), EYFP (Clontech), Topaz, Venus, mCitrine, YPet, TurboYFP, ZsYellow1 (Clontech), Kusabira Orange (MBL), mOrange, mKO, TurboRFP (Evrogen), tdTomato, TagRFP (Evrogen), DsRed (Clontech), DsRed2 (Clontech), mStrawberry, TurboFP602 (Evrogen), AsRed2 (Clontech), mRFP1, J-Red, mCherry, HcRed1 (Clontech), Katusha, Kate (Evrogen), TurboFP635 (Evrogen), mPlum, and mRaspberry.

1. Click Chemistry

The Huisgen 1,3-dipolar cycloaddition, in particular the Cu(I)-catalyzed stepwise variant, is often referred to simply as the "click reaction". The Cu(I)-catalyzed variant (Tomoe et al., 2002) was first reported by Morten Meldal and co-workers from Carlsberg Laboratory, Denmark for the synthesis of peptidotriazoles on solid support. Fokin and Sharpless independently described it as a reliable catalytic process offering "an unprecedented level of selectivity, reliability, and scope for those organic synthesis endeavors which depend on the creation of covalent links between diverse building blocks", firmly placing it among the most reliable processes fitting the click criteria.

One of the most popular reactions within the click chemistry philosophy is the azide alkyne Huisgen cycloaddition using a Cu catalyst at room temperature discovered concurrently and independently by the groups of K. Barry Sharpless and Morten Meldal. This was an improvement over the same reaction first popularized by Rolf Huisgen in the 1970s, albeit at elevated temperatures in the absence of water and without a Cu catalyst (it is explained fully in 1,3-Dipolar Cycloaddition Chemistry, published by Wiley and updated in 2002). However, the azides and alkynes are both kinetically stable. Copper and Ruthenium are the commonly used catalysts in the reaction.

Copper catalyzed click reactions work essentially on terminal alkynes. The Cu species undergo metal insertion reaction into the terminal alkynes. Commonly used solvents are polar aprotic solvents such as THF, DMSO, $CH_3CN$, DMF as well as in non-polar aprotic solvents such as toluene. Neat solvents or a mixture of solvents may be used.

Click chemistry has widespread applications. Some of them are: preparative organic synthesis of 1,4-substituted triazoles; modification of peptide function with triazoles; modification of natural products and pharmaceuticals; drug discovery; macrocyclizations using Cu(1) catalyzed triazole couplings; modification of DNA and nucleotides by triazole ligation; supramolecular chemistry: calixarenes, rotaxanes, and catenanes; dendrimer design; carbohydrate clusters and carbohydrate conjugation by Cu(1) catalyzed triazole ligation reactions; polymers; material science; and nanotechnology (Moses and Moorhouse, 2007; Hein et al., 2008, each of which is incorporated herein by reference).

2. Synthesis of Modified Uridine Diphosphate Glucose (UDP-Glu) Bearing Thiol or Azide.

The initial success of 5-hmC glycosylation led to the hypothesis that thiol- or azide-modified glucose can be similarly transferred to 5-hmC in duplex DNA. Thus, the inventors have synthesized azide-substituted UDP-Glu and contemplate synthesizing thiol-substituted UDP-Glu for 5-hmC labeling. An azide tag is preferred since this functional group is not present inside cells. The click chemistry to label this group is completely bio-orthogonal, meaning no interference from biological samples (Kolb et al., 2001). An azide-substituted UDP-Glu shown in FIG. 3. The azide-substituted glucoses can be transferred to 5-hmC, see Song et al., 2011, which is incorporated herein by reference.

3. Biotinylation of 5-hmC in Genomic DNA for Affinity Purification

The functional group installed on 5-gmC can be readily labeled with commercially available maleimide or alkyne (click chemistry) linked with a biotin, respectively. The reaction of thiol with maleimide is highly efficient; however, this labeling reaction cannot tolerate proteins or small molecules that bear thiol groups. Thus, genomic DNA must be isolated from other cellular components prior to the labeling, which can be readily achieved. The azide labeling with commercially available biotin-linked alkyne is completely bio-orthogonal, thus genomic DNA with bound proteins can be directly used. In both cases, the biotin-labeled DNA fragments may pulled down with streptavidin and submitted for high-throughput sequencing in order to map out global distributions and the locations of 5-hmC in chromosome. This will reveal a distribution map of 5-hmC in genomic DNA at different development stages of a particular cell or cell line.

4. Labeling 5-gmC with a Photosensitizer

An alternative strategy that does not rely on converting 5-hmC:G base pair to a different base pair is to tether a photosensitizer to 5-gmC using approaches indicated in FIG. 1. Photosensitized one-electron oxidation can lead to site-specific oxidation of the modified 5-gmC or the nearby guanines (Tanabe et al., 2007; Meyer et al., 2003). Subsequent base (piperidine) treatment will lead to specific strand cleavage on the oxidized site (FIG. 4B) (Tanabe et al., 2007; Meyer et al., 2003). Thus, genomic DNA containing 5-gmC labeled with photosensitizer can be subjected to photo-oxidation and base treatment. DNA fragments will be generated with oxidation sites at the end. High-throughput sequencing will reveal these modification sites.

5. Attachment of a Sterically Bulky Group to 5-gmC

In another strategy, a sterically bulky group such as polyethyleneglycol (PEG), a dendrimer, or a protein such as streptavidin can be introduced to the thiol- or azide-modified 5-gmC. Although 5-gmC in duplex DNA does not interfere with the polymerization reaction catalyzed by various different polymerases, the presence of an additional bulky group on 5-gmC on the DNA template strand can interfere with the synthesis of the new strand by DNA polymerase. As a result, primer extension will lead to a partially extended primer of certain length. The modification sites can be revealed by sequencing the partially extended primers. This method can be very versatile. It can be used to determine the modification sites for a given promoter site of interest. A high-throughput format can be developed as well. DNA fragments containing multiple 5-hmC can be affinity purified and random or designed primers can be used to perform primer extension experiments on these DNA fragments. Partially extended primers can be collected and subjected to high-throughput sequencing using a similar protocol as described in the restriction enzyme digestion method. A bulky modification may stop the polymerization reaction a few bases ahead of the modification site. Still, this method will map the modification sites to the resolution of a few bases. Considering that most 5-hmC exists in a CpG sequence, the resolution can be adequate for most applications. With a bulky substitution on 5-gmC digestion of modified DNA by restriction enzymes could be blocked for the restriction enzyme digestion-based assay.

II. Assays Utilizing 5-hmc Modification

Nucleic acid analysis and evaluation includes various methods of amplifying, fragmenting, and/or hybridizing nucleic acids that have or have not been modified.

A. Genomic Analysis

Methodologies are available for large scale sequence analysis. In certain aspects, the methods described exploit these genomic analysis methodologies and adapt them for uses incorporating the methodologies described herein. In certain instances the methods can be used to perform high resolution hydroxtmethylation analysis on several thousand CpGs in genomic DNA. Therefore, methods are directed to analysis of the hydroxymethylation status of a genomic DNA sample, comprising one or more of the steps: (a) fragmenting the sample and enriching the sample for sequences comprising CpG islands, (b) generating a single stranded DNA library, (c) subjecting the sample to bisulfite treatment, (d) amplifying individual members of the single stranded DNA library by means of PCR, e.g., emulsion PCR, and (e) sequencing the amplified single stranded DNA library.

The present methods allow for analyzing the hydroxymethylation status of all regions of a complete genome, where changes in hydroxymethylation status are expected to have an influence on gene expression. Due to the combination of bisulfite treatment, amplification and high throughput sequencing, it is possible to analyze the hydroxymethylation status of at least 1000 and preferably 5000 CpG islands in parallel.

A "CpG island" as used herein refers to regions of DNA with a high G/C content and a high frequency of CpG dinucleotides relative to the whole genome of an organism of interest. Also used interchangeably in the art is the term "CG island." The 'p' in "CpG island" refers to the phosphodiester bond between the cytosine and guanine nucleotides.

DNA may be isolated from an organism of interest, including, but not limited to eukaryotic organisms and prokaryotic organisms, preferably mammalian organisms, such as humans.

In certain aspects, the step of enriching a sample for sequences comprising CpG islands can be done in different ways. One technique for enrichment is immunoprecipitation of methylated DNA using a methyl-Cytosine specific antibody (Weber et al., 2005). Alternatively, an enrichment step can comprise digesting the sample with a one or more restriction enzymes which more frequently cut regions of DNA comprising no CpG islands and less frequently cut regions comprising CpG islands, and isolating DNA fragments with a specific size range.

The inventors have demonstrated that while the methylation-insensitive restriction enzyme MspI can completely cut C(5-meC)GG and partially cut C(5-hmC)GG, its activity is completely blocked by C(5-gmC)GG. This indicates that the introduction of a glucose moiety can change the property of 5-hmC in duplex DNA. With bulkier groups on 5-hmC, digestions by other restriction enzymes that recognize DNA sequences containing CpG can be blocked. Since 5-gmC can block restriction enzyme digestion, the genomic DNA modified with 5-gmC can be treated with and without restriction enzymes and subjected to known methods of mapping the genome-wide distribution and location of the 5-hmC modification.

Such restrictions enzymes can be selected by a person skilled in the art using conventional Bioinformatics approaches. The selection of appropriate enzymes also has a substantial influence on the average size of fragments that ultimately will be generated and sequenced. The selection of appropriate enzymes may be designed in such a way that it promotes enrichment of a certain fragment length. Thus, the selection may be adjusted to the kind of sequencing method which is finally applied. For most sequencing methods, a fragment length between 100 and 1000 by has been proven to be efficient. Therefore, in one embodiment, said fragment size range is from 100, 200 or 300 base pairs to 400, 500, 600, 700, 800, 900, or 1000 base pairs (bp), including all ranges and values there between.

The human genome reference sequence (NCBI Build 36.1 from March 2006; assembled parts of chromosomes only) has a length of 3,142,044,949 bp and contains 26,567 annotated CpG islands (CpGs) for a total length of 21,073,737 bp (0.67%). In certain aspects, a DNA sequence read hits a CpG if the read overlaps with the CpG by at least 50 bp.

As a non-limiting example, the following enzymes or their isoschizomers (with the following restriction sites) can be used for a method according to the present invention: MseI (TTAA), Tsp509 (AATT), AluI (AGCT), N1aIII (CATG), BfaI (CTAG), HpyCH4 (TGCA), Dpu1 (GATC), MboII (GAAGA), M1yI (GAGTC), BCCI (CCATC). Isoschizomers are pairs of restriction enzymes specific to the same recognition sequence and cut in the same location.

Embodiments include a CG island enriched library produced from genomic DNA by digestion with several restriction enzymes that preferably cut within non-CG island regions. In certain aspects, the restriction enzymes are selected in such a way that digestion can result in fragments with a size range between 300, 400, 500, 600 to 500, 600, 800, 900 bp or greater, including all ranges and values there between. The library fragments are ligated to adaptors. Subsequently, a conventional bisulfite treatment is performed according to methods that are well known in the art. As a result, unmethylated cytosine residues are converted to Uracil residues, which in a subsequent sequencing reaction base calling are identified as "T" instead of "C", when compared with a non bisulfite treated reference. Subsequent to bisulfite treatment, the sample is subjected to a conventional sequencing protocol.

As one example, the 454 Genome Sequencer System supports the sequencing of samples from a wide variety of starting materials including, but not limited to, eukaryotic or bacterial genomic DNA. Genomic DNAs are fractionated into small, 100- to 1000-bp fragments with an appropriate specific combination of restriction enzymes which enriches for CpG island containing fragments. In one embodiment, the restriction enzymes used for a method according to the present invention are selected from a group consisting of MseI, Tsp509, Alu1, N1aIII, BfaI, HpyCH4, Dpu1, MboII, M1yI, and BCCI, or any isoschizomer of any of the enzymes mentioned. Preferably, 4-5 different enzymes are selected.

Using a series of standard molecular biology techniques, short adaptors (A and B) are added to each fragment. The adaptors are used for purification, amplification, and sequencing steps. Single-stranded fragments with A and B adaptors compose the sample library used for subsequent steps.

Prior to ligation of the adaptors, the fragments can be completely double stranded without any single stranded overhang. A fragment polishing reaction is performed using e.g. $E.\ coli$ T4 DNA polymerase. In one embodiment, the polishing reaction is performed in the presence of hydroxymethyl-dCTP instead of dCTP. In another embodiment, the fragment polishing reaction is performed in the presence of a DNA polymerase which lacks proofreading activity, such as Tth DNA polymerase (Roche Applied Science Cat. No: 11 480 014 001).

The two different double stranded adaptors A and B are ligated to the ends of the fragments. Some or all of the C-residues of adaptors A and B can be hydroxymethyl-C residues. Subsequently, the fragments containing at least one B adaptor are immobilized on a streptavidin coated solid support and a nick repair-fill-in synthesis is performed using a strand displacement enzyme such as Bst Polymerase (New England Biolabs). Preferably said reaction is performed in the presence of hydroxymethyl-dCTP instead of dCTP. Subsequently single stranded molecules comprising one adaptor A and one adaptor B are removed from the streptavidin coated beads as disclosed in (Margulies et al., 2005). In those cases where hydroxymethyl-dCTP replaces dCTP, it can be used at the same concentrations as dCTP is used in the original protocol.

The bisulfite treatment can be done according to standard methods that are well known in the art (Frommer et al., 1992; Zeschnigk et al., 1997; Clark et al., 1994). The sample can be purified, for example by a Sephadex size exclusion column or, at least by means of precipitation. It is also within the scope of the present invention, if directly after bisulfite treatment, or directly after bisulfite treatment followed by purification, the sample is amplified by means of performing a conventional PCR using amplification primers with sequences corresponding to the A and B adaptor sequences.

In certain aspects, the bisulfite treated and optionally purified and/or amplified single-stranded DNA library is immobilized onto specifically designed DNA Capture Beads. Each bead carries a unique single-stranded DNA library fragment.

A library fragment can be amplified within its own microreactor comprised of a water-in-oil emulsion, excluding competing or contaminating sequences. Amplification of the entire fragment collection can be done in parallel; for each fragment, this results in a copy number of several million clonally amplified copies of the unique fragment per bead. After PCR amplification within the emulsion, the emulsion is broken while the amplified fragments remain bound to their specific beads.

B. Modification Sensitive Enzymes.

DNA methyltransferases (MTases) that transfer a methyl group from S-adenosylmethionine to either adenine or cytosine residues, are found in a wide variety of prokaryotes and eukaryotes. Methylation should be considered when digesting DNA with restriction endonucleases because cleavage can be blocked or impaired when a particular base in the recognition site is methylated or otherwise modified.

In prokaryotes, MTases have most often been identified as elements of restriction/modification systems that act to protect host DNA from cleavage by the corresponding restriction endonuclease. Most laboratory strains of $E.\ coil$ contain three site-specific DNA methylases. Some or all of the sites for a restriction endonuclease may be resistant to cleavage when isolated from strains expressing the Dam or Dcm methylases if the methylase recognition site overlaps the endonuclease recognition site. For example, plasmid DNA isolated from dam+ $E.\ coli$ is completely resistant to cleavage by MboI, which cleaves at GATC sites.

Not all DNA isolated from $E.\ coli$ is methylated to the same extent. While pBR322 DNA is fully modified (and is therefore completely resistant to MboI digestion), only about 50% of $\lambda$ DNA Dam sites are methylated, presumably because the methylase does not have the opportunity to methylate the DNA fully before it is packaged into the phage head. As a result, enzymes blocked by Dam or Dcm modification will yield partial digestion patterns with $\lambda$ DNA. Restriction sites that are blocked by Dam or Dcm methylation can be unmethylated by cloning DNA into a dam-, dcm-strain of $E.\ coli$, such as dam/dcm-Competent $E.\ coli$ (NEB #C2925).

CpG MTases, found in higher eukaryotes (e.g., Dnmt1), transfer a methyl group to the C5 position of cytosine residues. Patterns of CpG methylation are heritable, tissue specific and correlate with gene expression. Consequently, CpG methylation has been postulated to play a role in differentiation and gene expression (fosse and Kornberg, 1962). The effects of CpG methylation are mainly a concern when digesting eukaryotic genomic DNA. CpG methylation patterns are not retained once the DNA is cloned into a bacterial host.

The table below summarizes methylation sensitivity for NEB restriction enzymes, indicating whether or not cleavage is blocked or impaired by Dam, Dcm or CpG methylation if or when it overlaps each recognition site. REBASE, the restriction enzyme database, can be consulted for more detailed information and specific examples. (Marinus and Morris, 1973; Geier and Modrich, 1979; May and Hattman, 1975; Siegfried and Cedar, 1997).

| Enzyme | Sequence | Dam | Dcm | CpG |
|---|---|---|---|---|
| AatII | GACGT/C | Not Sensitive | Not Sensitive | Blocked |
| Acc65I | G/GTACC | Not Sensitive | Blocked by Some Overlapping Combinations | Blocked by Some Overlapping Combinations |
| AccI | GT/MKAC | Not Sensitive | Not Sensitive | Blocked by Overlapping Methylation |
| AclI | CCGC(-3/-1) | Not Sensitive | Not Sensitive | Blocked |
| AclI | AA/CGTT | Not Sensitive | Not Sensitive | Blocked |
| AcuI | CTGAAG(16/14) | Not Sensitive | Not Sensitive | Not Sensitive |
| AfeI | AGC/GCT | Not Sensitive | Not Sensitive | Blocked |
| AflII | C/TTAAG | Not Sensitive | Not Sensitive | Not Sensitive |
| AflIII | A/CRYGT | Not Sensitive | Not Sensitive | Not Sensitive |
| AgeI | A/CCGGT | Not Sensitive | Not Sensitive | Blocked |
| AgeI-HF ™ | A/CCGGT | — | — | — |
| AhdI | GACNNN/NNGTC | Not Sensitive | Not Sensitive | Impaired by Some Overlapping Combinations |
| AleI | CACNN/NNGTG | Not Sensitive | Not Sensitive | Impaired by Some Overlapping Combinations |
| AluI | AG/CT | Not Sensitive | Not Sensitive | Not Sensitive |
| AlwI | GGATC(4/5) | Blocked | Not Sensitive | Not Sensitive |
| AlwNI | CAGNNN/CTG | Not Sensitive | Blocked by Overlapping Methylation | Not Sensitive |
| ApaI | GGGCC/C | Not Sensitive | Blocked by Overlapping Methylation | Blocked by Overlapping Methylation |
| ApaLI | G/TGCAC | Not Sensitive | Not Sensitive | Blocked by Overlapping Methylation |
| ApeKI | G/CWGC | Not Sensitive | Not Sensitive | Not Sensitive |
| ApoI | R/AATTY | Not Sensitive | Not Sensitive | Not Sensitive |
| AscI | GG/CGCGCC | Not Sensitive | Not Sensitive | Blocked |
| AseI | AT/TAAT | Not Sensitive | Not Sensitive | Not Sensitive |
| AsiSI | GCGAT/CGC | Not Sensitive | Not Sensitive | Blocked |
| AvaI | C/YCGRG | Not Sensitive | Not Sensitive | Blocked |
| AvaII | G/GWCC | Not Sensitive | Blocked by Overlapping Methylation | Blocked by Overlapping Methylation |
| AvrII | C/CTAGG | Not Sensitive | Not Sensitive | Not Sensitive |
| BaeGI | GKGCM/C | Not Sensitive | Not Sensitive | Not Sensitive |
| BaeI | (10/15)ACNNNNGTAYC(12/7) | Not Sensitive | Not Sensitive | Blocked by Some Overlapping Combinations |

-continued

| Enzyme | Sequence | Dam | Dcm | CpG |
|---|---|---|---|---|
| BamHI | G/GATCC | Not Sensitive | Not Sensitive | Not Sensitive |
| BamHI-HF ™ | G/GATCC | Not Sensitive | Not Sensitive | Not Sensitive |
| BanI | G/GYRCC | Not Sensitive | Blocked by Some Overlapping Combinations | Blocked by Some Overlapping Combinations |
| BanII | GRGCY/C | Not Sensitive | Not Sensitive | Not Sensitive |
| BbsI | GAAGAC(2/6) | Not Sensitive | Not Sensitive | Not Sensitive |
| BbvCI | CCTCAGC(-5/-2) | Not Sensitive | Not Sensitive | Impaired by Overlapping Methylation |
| BbvI | GCAGC(8/12) | Not Sensitive | Not Sensitive | Not Sensitive |
| BccI | CCATC(4/5) | Not Sensitive | Not Sensitive | Not Sensitive |
| BceAI | ACGGC(12/14) | Not Sensitive | Not Sensitive | Blocked |
| BcgI | (10/12)CGANNNNNNTGC(12/10) | Blocked by Overlapping Methylation | Not Sensitive | Blocked by Some Overlapping Combinations |
| BciVI | GTATCC(6/5) | Not Sensitive | Not Sensitive | Not Sensitive |
| BclI | T/GATCA | Blocked | Not Sensitive | Not Sensitive |
| BfaI | C/TAG | Not Sensitive | Not Sensitive | Not Sensitive |
| BfuAI | ACCTGC(4/8) | Not Sensitive | Not Sensitive | Impaired by Overlapping Methylation |
| BfuCI | /GATC | Not Sensitive | Not Sensitive | Blocked by Overlapping Methylation |
| BglI | GCCNNNN/NGGC | Not Sensitive | Not Sensitive | Blocked by Some Overlapping Combinations |
| BglII | A/GATCT | Not Sensitive | Not Sensitive | Not Sensitive |
| BlpI | GC/TNAGC | Not Sensitive | Not Sensitive | Not Sensitive |
| BmgBI | CACGTC(-3/-3) | Not Sensitive | Not Sensitive | Blocked |
| BmrI | ACTGGG(5/4) | Not Sensitive | Not Sensitive | Not Sensitive |
| BmtI | GCTAG/C | Not Sensitive | Not Sensitive | Not Sensitive |
| BpmI | CTGGAG(16/14) | Not Sensitive | Not Sensitive | Not Sensitive |
| Bpu10I | CCTNAGC(-5/-2) | Not Sensitive | Not Sensitive | Not Sensitive |
| BpuEI | CTTGAG(16/14) | Not Sensitive | Not Sensitive | Not Sensitive |
| BsaAI | YAC/GTR | Not Sensitive | Not Sensitive | Blocked |
| BsaBI | GATNN/NNATC | Blocked by Overlapping Methylation | Not Sensitive | Blocked by Some Overlapping Combinations |
| BsaHI | GR/CGYC | Not Sensitive | Blocked by Some Overlapping Combinations | Blocked |
| BsaI | GGTCTC(1/5) | Not Sensitive | Blocked by Overlapping Methylation | Blocked by Some Overlapping Combinations |

-continued

| Enzyme | Sequence | Dam | Dcm | CpG |
|---|---|---|---|---|
| BsaI-HF™ | GGTCTC(1/5) | — | Blocked by Overlapping Methylation | — |
| BsaJI | C/CNNGG | Not Sensitive | Not Sensitive | Not Sensitive |
| BsaWI | W/CCGGW | Not Sensitive | Not Sensitive | Not Sensitive |
| BsaXI | (9/12)ACNNNNNCTCC(10/7) | Not Sensitive | Not Sensitive | Not Sensitive |
| BseRI | GAGGAG(10/8) | Not Sensitive | Not Sensitive | Not Sensitive |
| BseYI | CCCAGC(-5/-1) | Not Sensitive | Not Sensitive | Blocked by Overlapping Methylation |
| BsgI | GTGCAG(16/14) | Not Sensitive | Not Sensitive | Not Sensitive |
| BsiEI | CGRY/CG | Not Sensitive | Not Sensitive | Blocked |
| BsiHKAI | GWGCW/C | Not Sensitive | Not Sensitive | Not Sensitive |
| BsiWI | C/GTACG | Not Sensitive | Not Sensitive | Blocked |
| BslI | CCNNNNN/NNGG | Not Sensitive | Blocked by Some Overlapping Combinations | Blocked by Some Overlapping Combinations |
| BsmAI | GTCTC(1/5) | Not Sensitive | Not Sensitive | Blocked by Some Overlapping Combinations |
| BsmBI | CGTCTC(1/5) | Not Sensitive | Not Sensitive | Blocked |
| BsmFI | GGGAC(10/14) | Not Sensitive | Blocked by Overlapping Methylation | Blocked by Overlapping Methylation |
| BsmI | GAATGC(1/-1) | Not Sensitive | Not Sensitive | Not Sensitive |
| BsoBI | C/YCGRG | Not Sensitive | Not Sensitive | Not Sensitive |
| Bsp1286I | GDGCH/C | Not Sensitive | Not Sensitive | Not Sensitive |
| BspCNI | CTCAG(9/7) | Not Sensitive | Not Sensitive | Not Sensitive |
| BspDI | AT/CGAT | Blocked by Overlapping Methylation | Not Sensitive | Blocked |
| BspEI | T/CCGGA | Blocked by Overlapping Methylation | Not Sensitive | Impaired |
| BspHI | T/CATGA | Blocked by Overlapping Methylation | Not Sensitive | Not Sensitive |
| BspMI | ACCTGC(4/8) | Not Sensitive | Not Sensitive | Not Sensitive |
| BspQI | GCTCTTC(1/4) | Not Sensitive | Not Sensitive | Not Sensitive |
| BsrBI | CCGCTC(-3/-3) | Not Sensitive | Not Sensitive | Blocked by Some Overlapping Combinations |
| BsrDI | GCAATG(2/0) | Not Sensitive | Not Sensitive | Not Sensitive |
| BsrFI | R/CCGGY | Not Sensitive | Not Sensitive | Blocked |
| BsrGI | T/GTACA | Not Sensitive | Not Sensitive | Not Sensitive |
| BsrI | ACTGG(1/-1) | Not Sensitive | Not Sensitive | Not Sensitive |
| BssHII | G/CGCGC | Not Sensitive | Not Sensitive | Blocked |

-continued

| Enzyme | Sequence | Dam | Dcm | CpG |
|---|---|---|---|---|
| BssKI | /CCNGG | Not Sensitive | Blocked by Overlapping Methylation | Blocked by Overlapping Methylation |
| BssSI | CACGAG(-5/-1) | Not Sensitive | Not Sensitive | Not Sensitive |
| BstAPI | GCANNNN/NTGC | Not Sensitive | Not Sensitive | Blocked by Some Overlapping Combinations |
| BstBI | TT/CGAA | Not Sensitive | Not Sensitive | Blocked |
| BstEII | G/GTNACC | Not Sensitive | Not Sensitive | Not Sensitive |
| BstNI | CC/WGG | Not Sensitive | Not Sensitive | Not Sensitive |
| BstUI | CG/CG | Not Sensitive | Not Sensitive | Blocked |
| BstXI | CCANNNNN/NTGG | Not Sensitive | Blocked by Some Overlapping Combinations | Not Sensitive |
| BstYI | R/GATCY | Not Sensitive | Not Sensitive | Not Sensitive |
| BstZ17I | GTA/TAC | Not Sensitive | Not Sensitive | Blocked by Some Overlapping Combinations |
| Bsu36I | CC/TNAGG | Not Sensitive | Not Sensitive | Not Sensitive |
| BtgI | C/CRYGG | Not Sensitive | Not Sensitive | Not Sensitive |
| BtgZI | GCGATG(10/14) | Not Sensitive | Not Sensitive | Impaired |
| BtsCI | GGATG(2/0) | Not Sensitive | Not Sensitive | Not Sensitive |
| BtsI | GCAGTG(2/0) | Not Sensitive | Not Sensitive | Not Sensitive |
| Cac8I | GCN/NGC | Not Sensitive | Not Sensitive | Blocked by Some Overlapping Combinations |
| ClaI | AT/CGAT | Blocked by Overlapping Methylation | Not Sensitive | Blocked |
| CspCI | (11/13)CAANNNNNGTGG(12/10) | Not Sensitive | Not Sensitive | Not Sensitive |
| CviAII | C/ATG | Not Sensitive | Not Sensitive | Not Sensitive |
| CviKI-1 | RG/CY | Not Sensitive | Not Sensitive | Not Sensitive |
| CviCI | G/TAC | Not Sensitive | Not Sensitive | Not Sensitive |
| DdeI | C/TNAG | Not Sensitive | Not Sensitive | Not Sensitive |
| DpnI | GA/TC | Not Sensitive | Not Sensitive | Blocked by Overlapping Methylation |
| DpnII | /GATC | Blocked | Not Sensitive | Not Sensitive |
| DraI | TTT/AAA | Not Sensitive | Not Sensitive | Not Sensitive |
| DraIII | CACNNN/GTG | Not Sensitive | Not Sensitive | Impaired by Overlapping Methylation |
| DrdI | GACNNNN/NNGTC | Not Sensitive | Not Sensitive | Blocked by Some Overlapping Combinations |

-continued

| Enzyme | Sequence | Dam | Dcm | CpG |
|---|---|---|---|---|
| EaeI | Y/GGCCR | Not Sensitive | Blocked by Overlapping Methylation | Blocked by Overlapping Methylation |
| EagI | C/GGCCG | Not Sensitive | Not Sensitive | Blocked |
| EagI-HF ™ | C/GGCCG | Not Sensitive | Not Sensitive | Blocked |
| EarI | CTCTTC(1/4) | Not Sensitive | Not Sensitive | Impaired by Overlapping Methylation |
| EciI | GGCGGA(11/9) | Not Sensitive | Not Sensitive | Blocked by Some Overlapping Combinations |
| Eco53kI | GAG/CTC | — | — | — |
| EcoNI | CCTNN/NNNAGG | Not Sensitive | Not Sensitive | Not Sensitive |
| EcoO109I | RG/GNCCY | Not Sensitive | Blocked by Overlapping Methylation | Not Sensitive |
| EcoP15I | CAGCAG(25/27) | Not Sensitive | Not Sensitive | Not Sensitive |
| EcoRI | G/AATTC | Not Sensitive | Not Sensitive | Blocked by Some Overlapping Combinations |
| EcoRI-HF ™ | G/AATTC | Not Sensitive | Not Sensitive | Blocked by Some Overlapping Combinations |
| EcoRV | GAT/ATC | Not Sensitive | Not Sensitive | Impaired by Some Overlapping Combinations |
| EcoRV-HF ™ | GAT/ATC | Not Sensitive | Not Sensitive | Impaired by Some Overlapping Combinations |
| FatI | /CATG | Not Sensitive | Not Sensitive | Not Sensitive |
| FauI | CCCGC(4/6) | Not Sensitive | Not Sensitive | Blocked |
| Fnu4HI | GC/NGC | Not Sensitive | Not Sensitive | Blocked by Overlapping Methylation |
| FokI | GGATG(9/13) | Not Sensitive | Impaired by Overlapping Methylation | Impaired by Overlapping Methylation |
| FseI | GGCCGG/CC | Not Sensitive | Impaired by Some Overlapping Combinations | Blocked |
| FspI | TGC/GCA | Not Sensitive | Not Sensitive | Blocked |
| HaeII | RGCGC/Y | Not Sensitive | Not Sensitive | Blocked |
| HaeIII | GG/CC | Not Sensitive | Not Sensitive | Not Sensitive |
| HgaI | GACGC(5/10) | Not Sensitive | Not Sensitive | Blocked |
| HhaI | GCG/C | Not Sensitive | Not Sensitive | Blocked |
| HincII | GTY/RAC | Not Sensitive | Not Sensitive | Blocked by Some Overlapping Combinations |

-continued

| Enzyme | Sequence | Dam | Dcm | CpG |
|---|---|---|---|---|
| HindIII | A/AGCTT | Not Sensitive | Not Sensitive | Not Sensitive |
| HinfI | G/ANTC | Not Sensitive | Not Sensitive | Blocked by Some Overlapping Combinations |
| HinP1I | G/CGC | Not Sensitive | Not Sensitive | Blocked |
| HpaI | GTT/AAC | Not Sensitive | Not Sensitive | Blocked by Some Overlapping Combinations |
| HpaII | C/CGG | Not Sensitive | Not Sensitive | Blocked |
| HphI | GGTGA(8/7) | Blocked by Overlapping Methylation | Not Sensitive | Not Sensitive |
| Hpy166II | GTN/NAC | Not Sensitive | Not Sensitive | Blocked by Overlapping Methylation |
| Hpy188I | TCN/GA | Blocked by Overlapping Methylation | Not Sensitive | Not Sensitive |
| Hpy188III | TC/NNGA | Blocked by Overlapping Methylation | Not Sensitive | Blocked by Overlapping Methylation |
| Hpy99I | CGWCG/ | Not Sensitive | Not Sensitive | Blocked |
| HpyAV | CCTTC(6/5) | Not Sensitive | Not Sensitive | Impaired by Overlapping Methylation |
| HpyCH4III | ACN/GT | Not Sensitive | Not Sensitive | Not Sensitive |
| HpyCH4IV | A/CGT | Not Sensitive | Not Sensitive | Blocked |
| HpyCH4V | TG/CA | Not Sensitive | Not Sensitive | Not Sensitive |
| I-CeuI | CGTAACTATAACGGTCCTAAGGTAGCGAA(-9/-13) | — | — | — |
| I-SceI | TAGGGATAACAGGGTAAT(-9/-13) | — | — | — |
| KasI | G/GCGCC | Not Sensitive | Not Sensitive | Blocked |
| KpnI | GGTAC/C | Not Sensitive | Not Sensitive | Not Sensitive |
| KpnI-HF ™ | GGTAC/C | — | — | — |
| MboI | /GATC | Blocked | Not Sensitive | Impaired by Overlapping Methylation |
| MboII | GAAGA(8/7) | Blocked by Overlapping Methylation | Not Sensitive | Not Sensitive |
| MfeI | C/AATTG | Not Sensitive | Not Sensitive | Not Sensitive |
| MfeI-HF ™ | C/AATTG | Not Sensitive | Not Sensitive | Not Sensitive |
| MluI | A/CGCGT | Not Sensitive | Not Sensitive | Blocked |
| MlyI | GAGTC(5/5) | Not Sensitive | Not Sensitive | |
| MmeI | TCCRAC(20/18) | Not Sensitive | Not Sensitive | Blocked by Overlapping Methylation |
| MnlI | CCTC(7/6) | Not Sensitive | Not Sensitive | Not Sensitive |

-continued

| Enzyme | Sequence | Dam | Dcm | CpG |
|---|---|---|---|---|
| MscI | TGG/CCA | Not Sensitive | Blocked by Overlapping Methylation | Not Sensitive |
| MseI | T/TAA | Not Sensitive | Not Sensitive | Not Sensitive |
| MslI | CAYNN/NNRTG | Not Sensitive | Not Sensitive | Not Sensitive |
| MspA1I | CMG/CKG | Not Sensitive | Not Sensitive | Blocked by Overlapping Methylation |
| MspI | C/CGG | Not Sensitive | Not Sensitive | Not Sensitive |
| MwoI | GCNNNNN/NNGC | Not Sensitive | Not Sensitive | Blocked by Some Overlapping Combinations |
| NaeI | GCC/GGC | Not Sensitive | Not Sensitive | Blocked |
| NarI | GG/CGCC | Not Sensitive | Not Sensitive | Blocked |
| Nb.BbvCI | CCTCAGC | Not Sensitive | Not Sensitive | Not Sensitive |
| Nb.BsmI | GAATGC | Not Sensitive | Not Sensitive | Not Sensitive |
| Nb.BsrDI | GCAATG | Not Sensitive | Not Sensitive | Not Sensitive |
| Nb.BtsI | GCAATG | — | — | — |
| NciI | CC/SGG | Not Sensitive | Not Sensitive | Impaired by Overlapping Methylation |
| NcoI | C/CATGG | Not Sensitive | Not Sensitive | Not Sensitive |
| NcoI-HF™ | C/CATGG | Not Sensitive | Not Sensitive | Not Sensitive |
| NdeI | CA/TATG | Not Sensitive | Not Sensitive | Not Sensitive |
| NgoMIV | G/CCGGC | Not Sensitive | Not Sensitive | Blocked |
| NheI | G/CTAGC | Not Sensitive | Not Sensitive | Blocked by Some Overlapping Combinations |
| NheI-HF™ | G/CTAGC | Not Sensitive | Not Sensitive | Blocked by Some Overlapping Combinations |
| NlaIII | CATG/ | Not Sensitive | Not Sensitive | Not Sensitive |
| NlaIV | GGN/NCC | Not Sensitive | Blocked by Overlapping Methylation | Blocked by Overlapping Methylation |
| NmeAIII | GCCGAG(21/19) | Not Sensitive | Not Sensitive | Not Sensitive |
| NotI | GC/GGCCGC | Not Sensitive | Not Sensitive | Blocked |
| NotI-HF™ | GC/GGCCGC | Not Sensitive | Not Sensitive | Blocked |
| NruI | TCG/CGA | Blocked by Overlapping Methylation | Not Sensitive | Blocked |
| NsiI | ATGCA/T | Not Sensitive | Not Sensitive | Not Sensitive |
| NspI | RCATG/Y | Not Sensitive | Not Sensitive | Not Sensitive |
| Nt.AlwI | GGATC(4/-5) | Blocked | Not Sensitive | Not Sensitive |

| Enzyme | Sequence | Dam | Dcm | CpG |
| --- | --- | --- | --- | --- |
| Nt.BbvCI | CCTCAGC(-5/-7) | Not Sensitive | Not Sensitive | Blocked by Some Overlapping Combinations |
| Nt.BsmAI | GTCTC(1/-5) | Not Sensitive | Not Sensitive | Blocked |
| Nt.BspQI | GCTCTTC(1/-7) | Not Sensitive | Not Sensitive | Not Sensitive |
| Nt.BstNBI | GAGTC(4/-5) | Not Sensitive | Not Sensitive | Not Sensitive |
| Nt.CviPII | (0/-1)CCD | Not Sensitive | Not Sensitive | Blocked |
| PacI | TTAAT/TAA | Not Sensitive | Not Sensitive | Not Sensitive |
| PaeR7I | C/TCGAG | Not Sensitive | Not Sensitive | Blocked |
| PciI | A/CATGT | Not Sensitive | Not Sensitive | Not Sensitive |
| PflFI | GACN/NNGTC | Not Sensitive | Not Sensitive | Not Sensitive |
| PflMI | CCANNNN/NTGG | Not Sensitive | Blocked by Overlapping Methylation | Not Sensitive |
| PhoI | GG/CC | Not Sensitive | Impaired by Some Overlapping Combinations | Impaired by Some Overlapping Combinations |
| PI-PspI | TGGCAAACAGCTATTATGGGTATTATGGGT (-13/-17) | — | — | — |
| PI-SceI | ATCTATGTCGGGTGCGGAGAAAGAGGTAAT (-15/-19) | — | — | — |
| PleI | GAGTC(4/5) | Not Sensitive | Not Sensitive | Blocked by Some Overlapping Combinations |
| PmeI | GTTT/AAAC | Not Sensitive | Not Sensitive | Blocked by Some Overlapping Combinations |
| PmlI | CAC/GTG | Not Sensitive | Not Sensitive | Blocked |
| PpuMI | RG/GWCCY | Not Sensitive | Blocked by Overlapping Methylation | Not Sensitive |
| PshAI | GACNN/NNGTC | Not Sensitive | Not Sensitive | Blocked by Some Overlapping Combinations |
| PsiI | TTA/TAA | Not Sensitive | Not Sensitive | Not Sensitive |
| PspGI | /CCWGG | Not Sensitive | Blocked | Not Sensitive |
| PspOMI | G/GGCCC | Not Sensitive | Blocked by Overlapping Methylation | Blocked by Overlapping Methylation |
| PspXI | VC/TCGAGB | Not Sensitive | Not Sensitive | Impaired |
| PstI | CTGCA/G | Not Sensitive | Not Sensitive | Not Sensitive |
| PstI-HF ™ | CTGCA/G | — | — | — |
| PvuI | CGAT/CG | Not Sensitive | Not Sensitive | Blocked |
| PvuII | CAG/CTG | Not Sensitive | Not Sensitive | Not Sensitive |
| PvuII-HF ™ | CAG/CTG | Not Sensitive | Not Sensitive | Not Sensitive |

-continued

| Enzyme | Sequence | Dam | Dcm | CpG |
|---|---|---|---|---|
| RsaI | GT/AC | Not Sensitive | Not Sensitive | Blocked by Some Overlapping Combinations |
| RsrII | CG/GWCCG | Not Sensitive | Not Sensitive | Blocked |
| SacI | GAGCT/C | Not Sensitive | Not Sensitive | Not Sensitive |
| SacI-HF ™ | GAGCT/C | Not Sensitive | Not Sensitive | Not Sensitive |
| SacII | CCGC/GG | Not Sensitive | Not Sensitive | Blocked |
| SalI | G/TCGAC | Not Sensitive | Not Sensitive | Blocked |
| SalI-HF ™ | G/TCGAC | Not Sensitive | Not Sensitive | Blocked |
| SapI | GCTCTTC(1/4) | Not Sensitive | Not Sensitive | Not Sensitive |
| Sau3AI | /GATC | Not Sensitive | Not Sensitive | Blocked by Overlapping Methylation |
| Sau96I | G/GNCC | Not Sensitive | Blocked by Overlapping Methylation | Blocked by Overlapping Methylation |
| SbfI | CCTGCA/GG | Not Sensitive | Not Sensitive | Not Sensitive |
| SbfI-HF ™ | CCTGCA/GG | Not Sensitive | Not Sensitive | Not Sensitive |
| ScaI | AGT/ACT | Not Sensitive | Not Sensitive | Not Sensitive |
| ScaI-HF ™ | AGT/ACT | Not Sensitive | Not Sensitive | Not Sensitive |
| ScrFI | CC/NGG | Not Sensitive | Blocked by Overlapping Methylation | Blocked by Overlapping Methylation |
| SexAI | A/CCWGGT | Not Sensitive | Blocked | Not Sensitive |
| SfaNI | GCATC(5/9) | Not Sensitive | Not Sensitive | Impaired by Some Overlapping Combinations |
| SfcI | C/TRYAG | Not Sensitive | Not Sensitive | Not Sensitive |
| SfiI | GGCCNNNN/NGGCC | Not Sensitive | Impaired by Overlapping Methylation | Blocked by Some Overlapping Combinations |
| SfoI | GGC/GCC | Not Sensitive | Blocked by Some Overlapping Combinations | Blocked |
| SgrAI | CR/CCGGYG | Not Sensitive | Not Sensitive | Blocked |
| SmaI | CCC/GGG | Not Sensitive | Not Sensitive | Blocked |
| SmlI | C/TYRAG | Not Sensitive | Not Sensitive | Not Sensitive |
| SnaBI | TAC/GTA | Not Sensitive | Not Sensitive | Blocked |
| SpeI | A/CTAGT | Not Sensitive | Not Sensitive | Not Sensitive |
| SphI | GCATG/C | Not Sensitive | Not Sensitive | Not Sensitive |
| SphI-HF ™ | GCATG/C | Not Sensitive | Not Sensitive | Not Sensitive |
| SspI | AAT/ATT | Not Sensitive | Not Sensitive | Not Sensitive |
| SspI-HF ™ | AAT/ATT | Not Sensitive | Not Sensitive | Not Sensitive |
| StuI | AGG/CCT | Not Sensitive | Blocked by Overlapping Methylation | Not Sensitive |

-continued

| Enzyme | Sequence | Dam | Dcm | CpG |
|---|---|---|---|---|
| StyD4I | /CCNGG | Not Sensitive | Blocked by Overlapping Methylation | Impaired by Overlapping Methylation |
| StyI | C/CWWGG | Not Sensitive | Not Sensitive | Not Sensitive |
| StyI-HF ™ | C/CWWGG | — | — | — |
| SwaI | ATTT/AAAT | Not Sensitive | Not Sensitive | Not Sensitive |
| TaqαI | T/CGA | Blocked by Overlapping Methylation | Not Sensitive | Not Sensitive |
| TfiI | G/AWTC | Not Sensitive | Not Sensitive | Blocked by Some Overlapping Combinations |
| TliI | C/TCGAG | Not Sensitive | Not Sensitive | Impaired |
| TseI | G/CWGC | Not Sensitive | Not Sensitive | Blocked by Some Overlapping Combinations |
| Tsp45I | /GTSAC | Not Sensitive | Not Sensitive | Not Sensitive |
| Tsp509I | /AATT | Not Sensitive | Not Sensitive | Not Sensitive |
| TspMI | C/CCGGG | Not Sensitive | Not Sensitive | Blocked |
| TspRI | NNCASTGNN/ | Not Sensitive | Not Sensitive | Not Sensitive |
| Tth111I | GACN/NNGTC | Not Sensitive | Not Sensitive | Not Sensitive |
| XbaI | T/CTAGA | Blocked by Overlapping Methylation | Not Sensitive | Not Sensitive |
| XcmI | CCANNNNN/NNNNTGG | Not Sensitive | Not Sensitive | Not Sensitive |
| XhoI | C/TCGAG | Not Sensitive | Not Sensitive | Impaired |
| XmaI | C/CCGGG | Not Sensitive | Not Sensitive | Impaired |
| XmnI | GAANN/NNTTC | Not Sensitive | Not Sensitive | Not Sensitive |
| ZraI | GAC/GTC | Not Sensitive | Not Sensitive | Blocked |

C. Microarray Analysis

Microarray methods can be used in conjunction with the methods described herein for simultaneous testing of numerous genetic alterations of the human genome. The subject matter described herein can also be used in various fields to greatly improve the accuracy and reliability of nucleic acid analyses, chromosome mapping, and genetic testing. Selected chromosomal target elements can be included on the array and evaluated for 5-hmC content in conjunction with hybridization to a nucleic acid array. In an implementation that uses a diagnostic array (hereafter, "array"), such as a microarray used for comparative genomic hybridization (CGH), a comprehensive battery of clinically relevant chromosomal loci can be selected and evaluated for 5-hmC status or content. 5-hmC in genomic DNA fragments are specifically labeled using radio-labels, fluorescent labels or amplifiable signals. These labeled target DNA fragments are then screened by hybridization using microarrays.

D. FRET-Based Hybridization Assay

Attach a fluorescent tag to the 5-hmC. Hybridize to a probe containing a nucleotide labeled with a fluorescent tag that functions as a FRET partner to the first. If the labeled based in the probe is juxtaposed with the labeled 5-hmC, a FRET signal will be observed.

E. Electrochemical Labeling

This method involves using AC impedance as a measurement for the presence of 5-hmC. Briefly, a nucleic acid probe specific for the sequence to be analyzed is immobilized on a gold electrode. The DNA fragment to be analyzed is added and allowed to hybridize to the probe. Excess non-hybridized, single-strand DNA is digested using nucleases. Biotin is covalently linked to the 5-hmC using the methods of the invention either before or after hybridization. Avidin-HRP is bound to the biotinylated DNA sequence then 4-chloronaphthol is added. If the HRP molecule is bound to the hybridized target DNA near the gold electrode, the HRP oxidizes the 4-chloronaphthol to a hydrophobic product that absorbs to the electrode surface. This results in a higher AC impedance if 5-hmC is present in the target DNA compared to a control sequence lacking 5-hmC.

F. Chromosomal Staining

Chromosomal DNA is prepared using standard karotyping techniques known in the art. The 5-hmC in the chromosomal DNA is labeled with a detectable moiety (fluorophore, radiolabel, amplifiable signal) and imaged in the context of the intact chromosomes.

III. Kits

The invention additionally provides kits for modifying cytosine bases of nucleic acids and/or subjecting such modified nucleic acids to further analysis. The contents of a kit can include one or more of a modification agent(s), a labeling reagent for detecting or modifying glucose or a 5-hmC, and, if desired, a substrate that contains or is capable of attaching to one or more modified 5-gmC. The substrate can be, e.g., a microsphere, antibody, or other binding agent.

Each kit preferably includes a 5-hmC modifying agent or agents, e.g., βGT and its functionalized substrate. One or more reagent is preferably supplied in a solid form or liquid buffer that is suitable for inventory storage, and later for addition into the reaction medium when the method of using the reagent is performed. Suitable packaging is provided. The kit may optionally provide additional components that are useful in the procedure. These optional components include buffers, capture reagents, developing reagents, labels, reacting surfaces, means for detection, control samples, instructions, and interpretive information.

The kit may optionally include a detectable label or a modified glucose-binding agent and, if desired, reagents for detecting the binding agent.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Labeling of 5-HMC

To elucidate the biology of 5-hmC, the first step is to identify the locations of 5-hmC within genomic DNA, but so far it has remained challenging to distinguish 5-hmC from 5-mC and to enrich 5-hmC-containing genomic DNA fragments.

Widely used methods to probe 5-mC, such as bisulfite sequencing and methylation-sensitive restriction digestion, cannot discriminate between 5-hmC and 5-mC (Huang et al., 2010; Jin et al., 2010). Anti-5-hmC antibodies have only recently become commercially available. However, attempts to use the antibodies to immuno-enrich 5-hmC-containing genomic DNA from complex genomes for sequencing have yet to be successful (Ito et al., 2010). A single-molecule, real-time sequencing technology has been applied to distinguish between cytosine, 5-mC and 5-hmC, but further improvements are necessary to affinity-enrich 5-hmC-containing DNA and to achieve base-resolution sequencing (Flusberg et al., 2010).

Figure 1A:
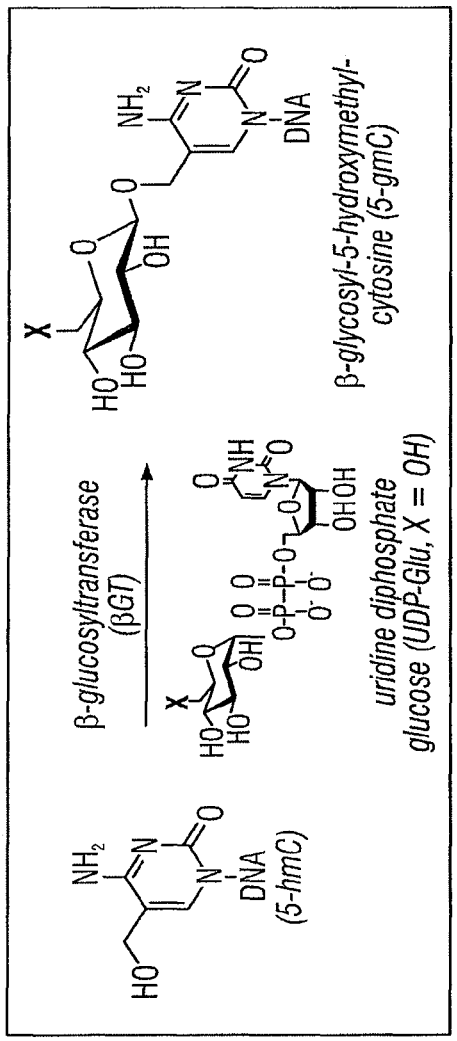
FIGS. 1A-1B. General strategy for 5-hmC modification and identification.
Figure 1B:
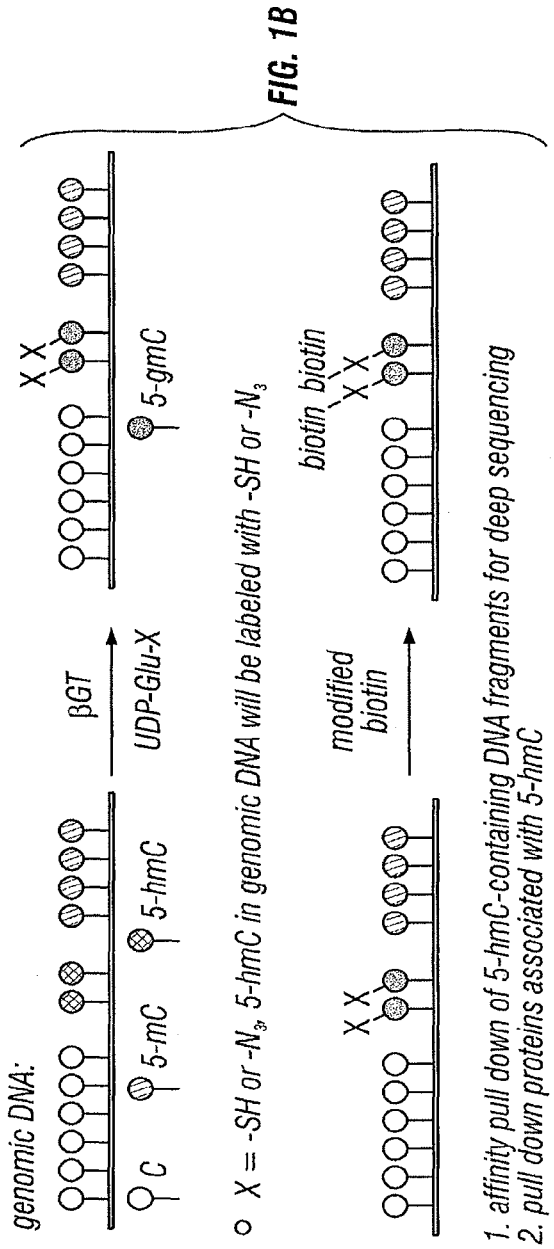

In certain aspects, the inventors describe a chemical tagging technology. It has been shown that 5-hmC is present in the genome of the T-even bacteriophages. A viral enzyme, β-glucosyltransferase (β-GT), can catalyze the transfer of a glucose moiety from uridine diphosphoglucose (UDP-Glu) to the hydroxyl group of 5-hmC, yielding β-glucosyl-5-hydroxymethyl-cytosine (5-gmC) in duplex DNA (Josse and Kornberg, 1962; Lariviere and Morera, 2004) (FIG. 1A). The inventors took advantage of this enzymatic process and used β-GT to transfer a chemically modified glucose, 6-N3-glucose, onto 5-hmC for selective bio-orthogonal labeling of 5-hmC in genomic DNA (FIG. 1B). With an azide group present, a biotin tag or any other tag can be installed using Huisgen cycloaddition (click) chemistry for a variety of enrichment, detection and sequencing applications (Kolb et al., 2001; Speers and Cravatt, 2004; Sletten and Bertozzi, 2009).

The inventors used the biotin tag for high-affinity capture and/or enrichment of 5-hmC-containing DNA for sensitive detection and deep sequencing to reveal genomic locations of 5-hmC (FIG. 1B). The covalent chemical labeling coupled with biotin-based affinity purification provides considerable advantages over noncovalent, antibody-based immunoprecipitation as it ensures accurate and comprehensive capture of 5-hmC-containing DNA fragments, while still providing high selectivity.

Figure 5A:
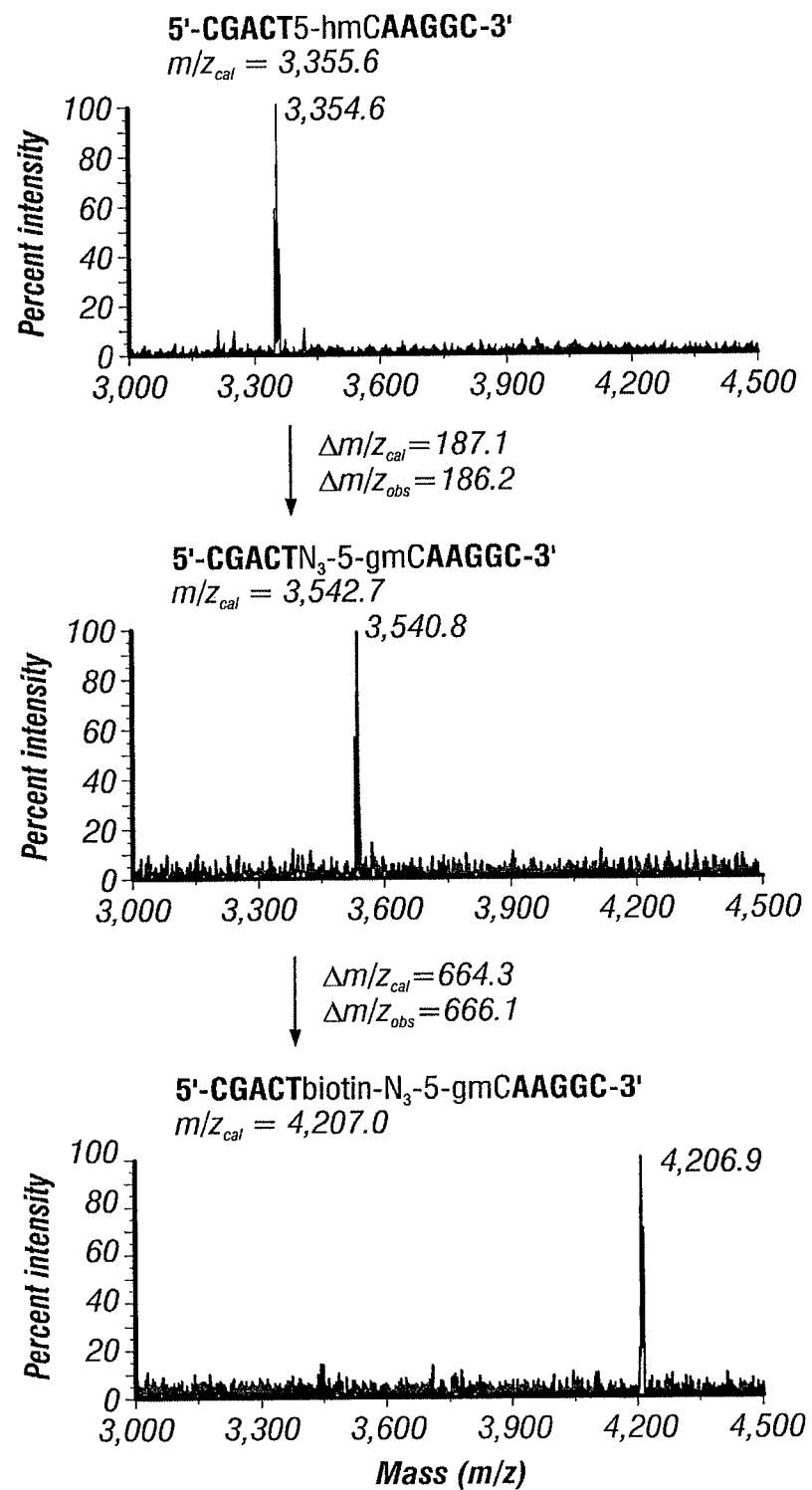
FIG. 5. Mass spec of 5-hmC, 5-$N_3$-gmC and biotin-5-$N_3$-gmC-containing 15 mer DNA with the corresponding reactions on the side. (FIG. A) MALDI-TOF of 5-hmC, 5-$N_3$-gmC and biotin-5-$N_3$-gmC-containing 15 mer DNA, respectively, with the calculated molecular weight and observed molecular weight indicated. (FIG. B) Corresponding reactions of βGT transferring 5-$N_3$-glucose to 5-$N_3$-gmC and the subsequent copper-free click chemistry on 5-$N_3$-gmC.
Figure 5B:
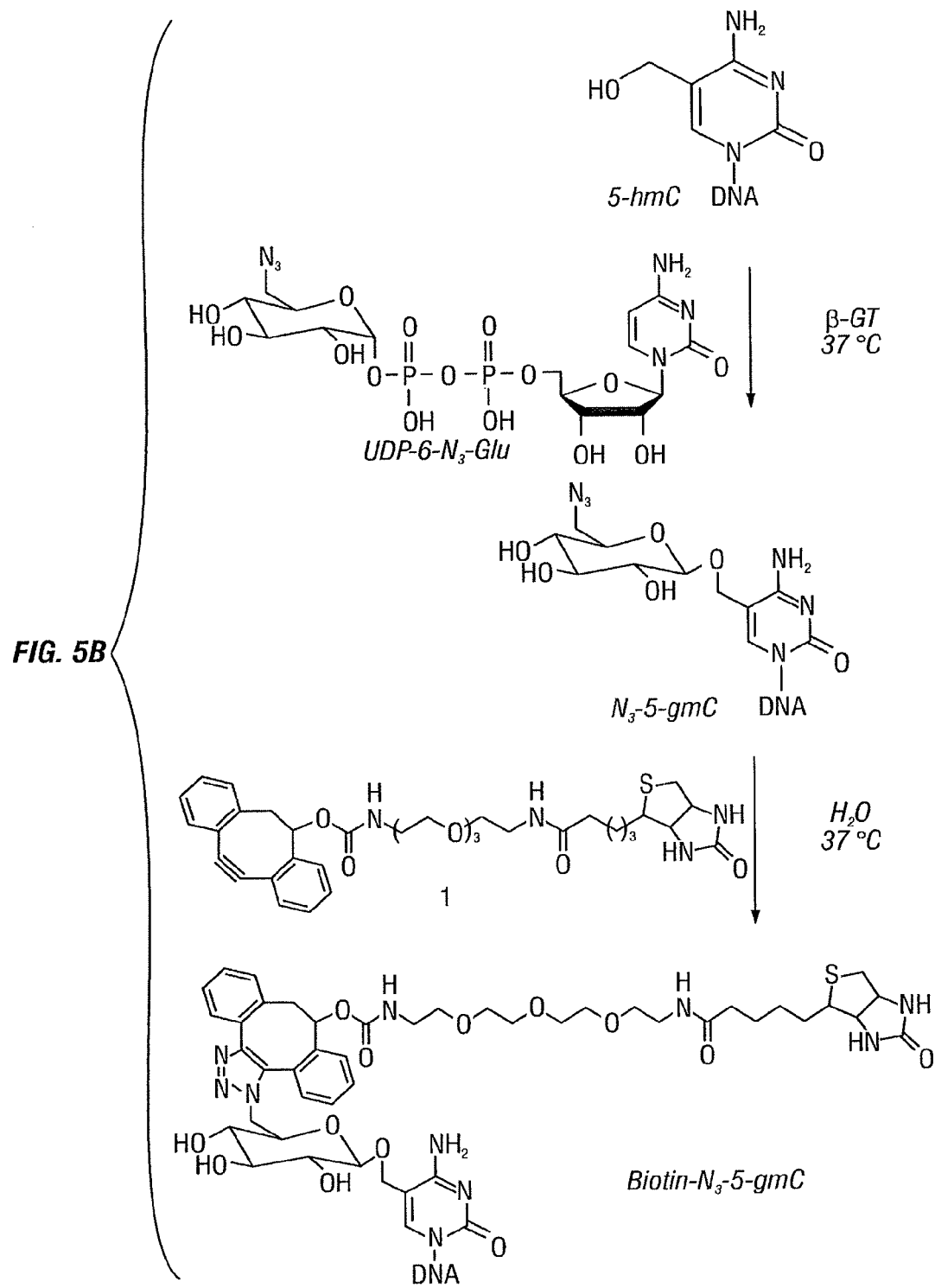
Figure 6:
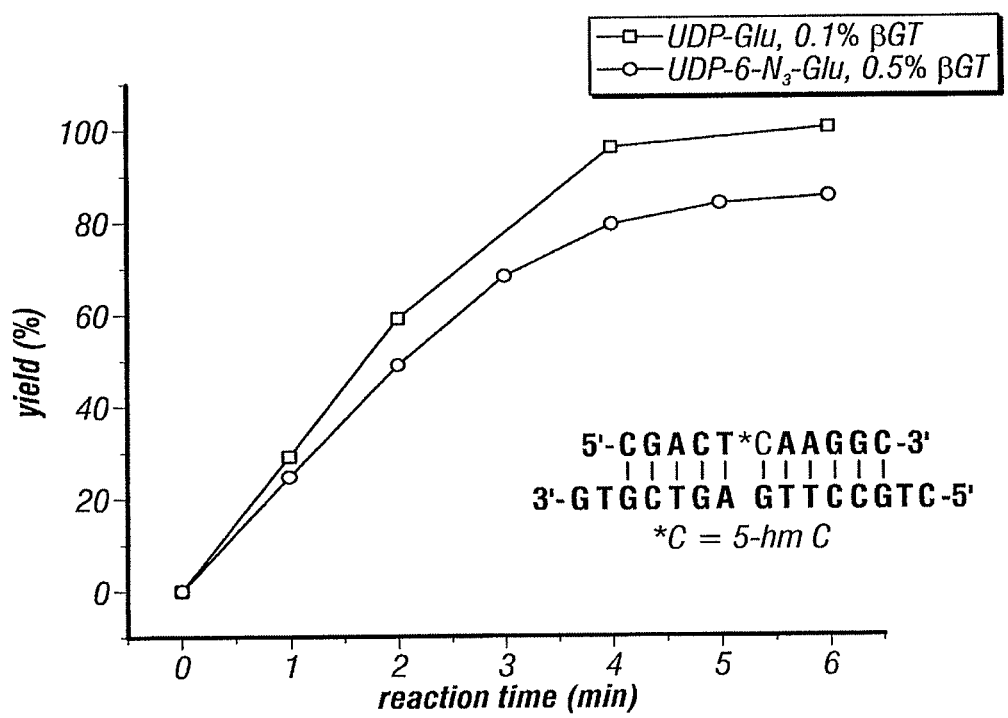
FIG. 6. Activity assays of wild-type βGT on UDP-Glu and UDP-6-N3-Glu. For all activity assays, a 60 μL reaction solution containing 50 mM HEPES buffer (pH 7.9), 25 mM $MgCl_2$, 30 dsDNA (sequence is shown in the inset), 300 μM UDP-Glu or UDP-6-N3-Glu, and 0.03 μM wild-type βGT (for UDP-Glu) or 0.15 μM wild-type βGT (for UDP-6-N3-Glu) was incubated at 37° C. The reaction was stopped at different incubation time points up to 6 min by immediately adding 100 mM EDTA and subjecting to Bio-Spin 6 column (Bio-Rad) to remove the excess UDP-Glu or UDP-6-N3-Glu. Samples were analyzed by HPLC with a C18 reverse-phase column equilibrated with buffer A (0.1 M TEAA, pH 7.0) and buffer B ($CH_3CN$), showing an approximately 6-fold decrease of rate (kcat) for reactions with UDP-6-N3-Glu compared to those with regular UDP-Glu.
Figure 8A:
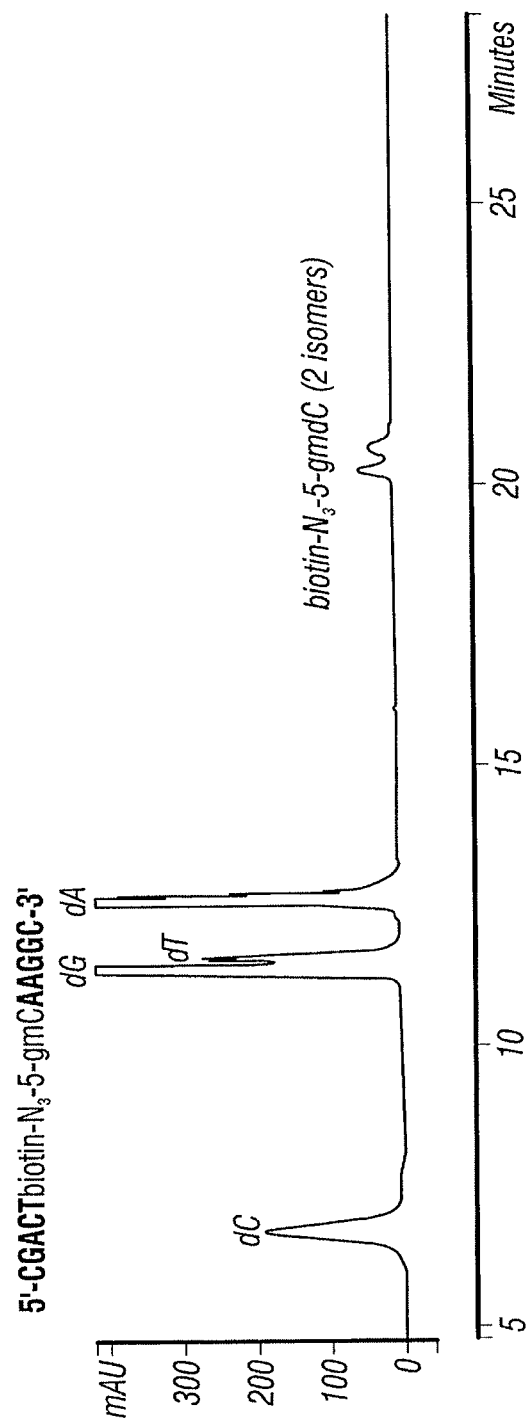
FIGS. 8A-8B. HPLC, and MS identification of biotin-N3-5-gmC. (A), HPLC chromatograms (260 nm) of the nucleosides derived from the 11-mer biotin-N3-5-gmC-containing synthetic DNA. The peaks corresponding to biotin-N3-5-gmC (a pair of isomers) were collected and subjected to HRMS analysis. (B), HRMS of biotin-N3-5-gmC (structures are shown in the insets). Theoretical m/z values are shown; observed m/z values are also shown.
Figure 8B:
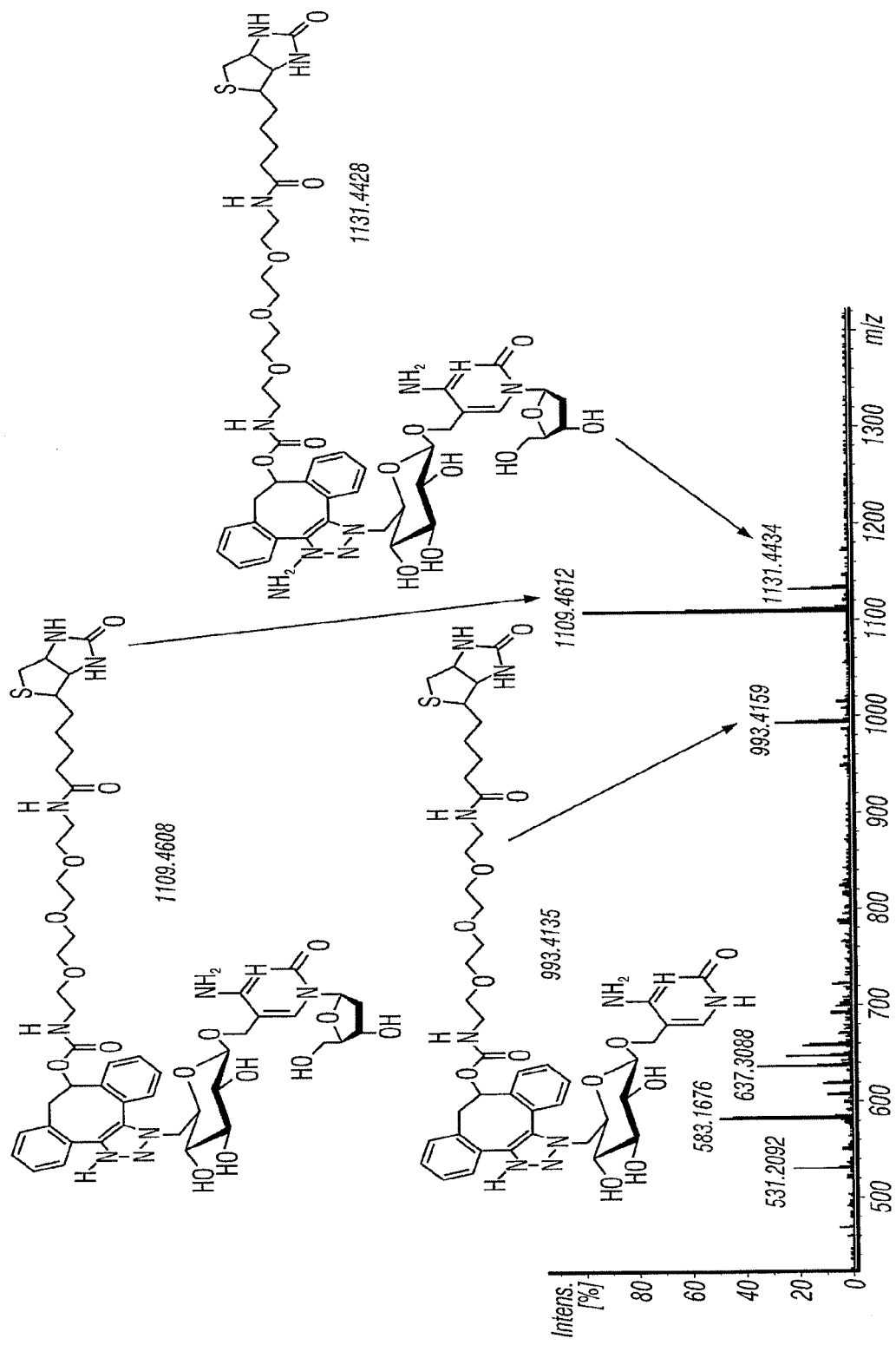
Figure 9A:
FIGS. 9A-9B. The streptavidin adduct of biotin-5-$N_3$-gmC hinders primer extension. (A) Sequence of 40 mer DNA containing cytosines derivatives used in primer extension. Cytosine 25, counting from right to left, with an asterisk presented the modified cytosines in the sequences, and also the position at which DNA polymerases tended to stall when the streptavidine adduct of biotin-5-$N_3$-gmC-containing DNA was used as template. The arrow corresponded to the reverse PCR primer used for primer extension. (B) Primer extension assays for 40 mer DNA containing different cytosine species, shown beside a Sanger sequencing ladder. No significant incomplete extension were observed in regular cytosine, 5-mC, 5-hmC-containing DNAs. Partial stalling of the primer extension at the modified position was observed in biotin-5-$N_3$-gmC-containing DNA. Primer extension were completely stalled when 5-$N_3$-gmC-containing DNA treated with 6 eq.-48 eq. of streptavidin. Position with the most significant stalling was position 24, one base before the modified position, although significant stalling still observed in the modified position (position 25, arrow). Primer extension using Sigma TaqRED polymerase, extension at 72° C. for 1 min. Sequencing ladder was performed with Sequenase from USB.
Figure 9B:
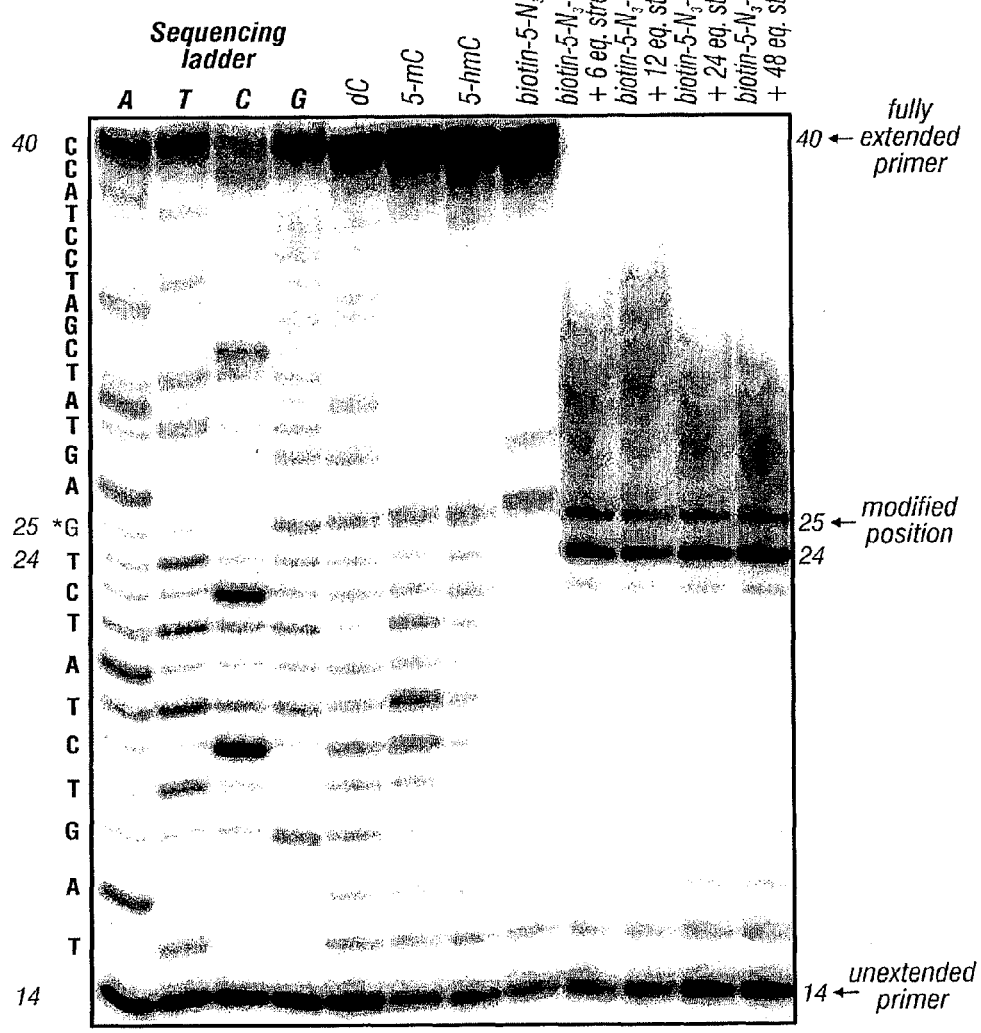

The inventors chemically synthesized UDP-6-N3-Glu (FIG. 3) and attempted the glycosylation reaction of an 11-mer duplex DNA containing a 5-hmC modification as a model system (FIG. 5). Wild-type β-GT worked efficiently using UDP-6-N3-Glu as the co-factor, showing only a sixfold decrease of the reaction rate compared to the native co-factor UDP-Glu (FIG. 6). The 6-N3-glucose transfer reaction finished within 5 min with as low as 1% enzyme concentration. The identity of the resulting β-6-azide-glucosyl-5-hydroxymethyl-cytosine (N3-5-gmC) of the 11-mer DNA was confirmed by matrix-assisted laser desorption/ionization—time of flight (MALDI-TOF) analysis (FIG. 5). One can readily couple N3-5-gmC with dibenzocyclooctyne-modified biotin (compound 1) by copper-free click chemistry to introduce a biotin group (FIG. 5) (Baskin et al., 2007; Ning et al., 2008). Again, the identity of the 11-mer DNA with the biotin-N3-5-gmC label was confirmed by MALDI-TOF analysis (FIG. 5). High-performance liquid chromatography (HPLC) analysis indicated that the click chemistry is high yielding (~90%) (FIG. 7). High-resolution mass spectroscopy (HRMS) analysis of the corresponding HPLC hydrolysates further verified that biotin-N3-5-gmC was formed (FIG. 8).

The properties of 5-hmC in duplex DNA are quite similar to those of 5-mC in terms of its sensitivity toward enzymatic reactions such as restriction enzyme digestion and polymerization (Flusberg et al., 2010; Josse and Kornberg, 1962; Lariviere and Morera, 2004). In an attempt to develop a method to differentiate these two bases in DNA, primer extension with a biotin-N3-5-gmC-modified DNA template was tested. Addition of streptavidin tetramer (binds biotin tightly) completely stops replication by Taq polymerase specifically at the modified position as well as one base before the modified position (FIG. 6). Therefore, this method has the potential to provide single-base resolution of the location of 5-hmC in DNA loci of interest.

Next, the inventors performed selective labeling of 5-hmC in genomic DNA from various cell lines and animal tissues (FIG. 10). Genomic DNA from various sources was sonicated into small fragments (~100-500 base pairs), treated with β-GT in the presence of UDP-6-N3-Glu or regular UDP-Glu (control group) to yield N3-5-gmC or 5-gmC modifications and finally labeled with cyclooctyne-biotin (1) to install biotin. Because each step is efficient and bio-orthogonal, this protocol ensures selective labeling of most 5-hmC in genomic DNA. The presence of biotin-N3-5-gmC allows affinity enrichment of this modification and accurate quantification of the amount of 5-hmC in a genome using avidin-horseradish peroxidase (HRP).

Figure 10A:
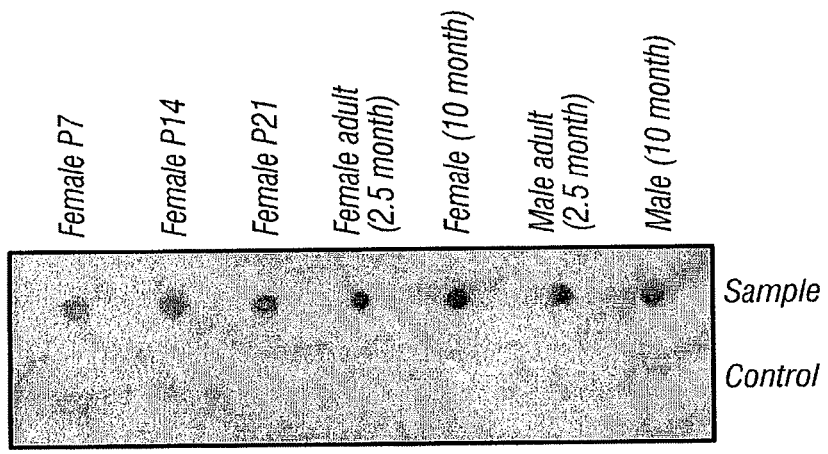
FIGS. 10A-10D. Quantification of 5-hmC in various cell lines and tissues. (A) Dot-blot assay of avidin-HRP detection and quantification of mouse cerebellum genomic DNA containing biotin-N3-5-gmC. Top row: 40 ng of biotin-labeled samples using UDP-6-N3-Glu. Bottom row: 40 ng of control samples using regular UDP-Glu without biotin label. The exact same procedures were followed for experiments in both rows. P7, P14 and P21 represent postnatal day 7, 14 and 21, respectively. (B) Amounts of 5-hmC are shown in percentage of total nucleotides of mouse genome. *, $P<0.05$, Student's t-test; means±s.e.m. for n=4 experiments. (C) Dot-blot assay of avidin-HRP detection and quantification of genomic DNA samples from four cell lines (from same blot as in a), except that each dot contains 700 ng DNA. (D) Amounts of 5-hmC are shown in percentage of total nucleotides of the genome; means±s.e.m. for n=4 experiments. The dashed line indicates the limit of detection (~0.004%).
Figure 10B:
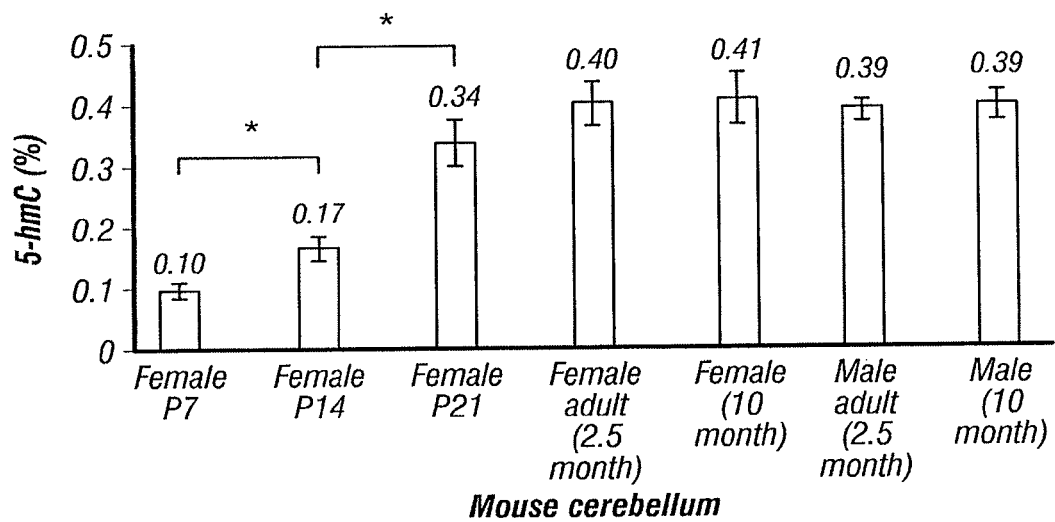

The inventors determined the total amount of 5-hmC in mouse cerebellum at different stages of development (FIGS. 10A and 10B). The control group showed almost no signal, demonstrating the high selectivity of this method. The amount of 5-hmC depends on the developmental stage of the mouse cerebellum (FIG. 10B). A gradual increase from postnatal day 7 (P7, 0.1% of total nucleotides in the genome) to adult stage (0.4% of total nucleotides) was observed (Munzel et al., 2010), which was further confirmed using antibody against 5-hmC through a dot-blot assay) (FIG. 11). These observations suggest that 5-hmC might play an important role in brain development. The 5-hmC level of mouse embryonic stem cells (mESC) was determined to be comparable to results reported previously (~0.05% of total nucleotides) (FIGS. 10C and 10D) (Tahiliani et al. 2009). In addition, the amount of 5-hmC in mouse adult neural stem cells (aNSC) was tested, which proved comparable to that of mESC (~0.04% of total nucleotides) (FIGS. 10C and 10D).

Figure 10C:
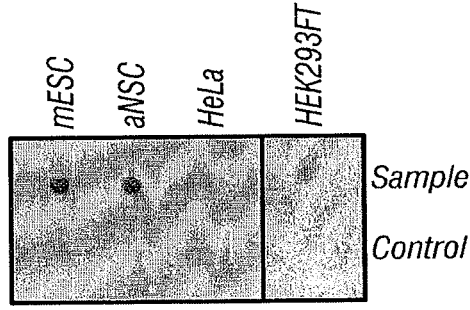
Figure 10D:
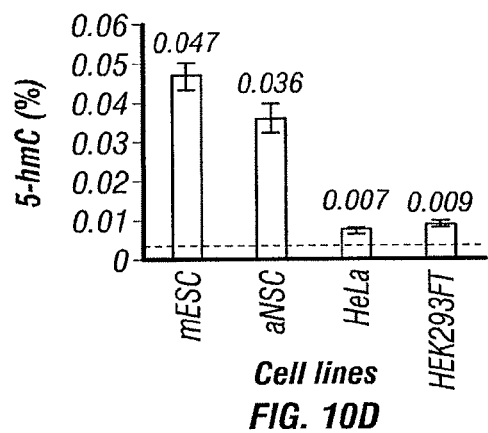
Figure 11A:
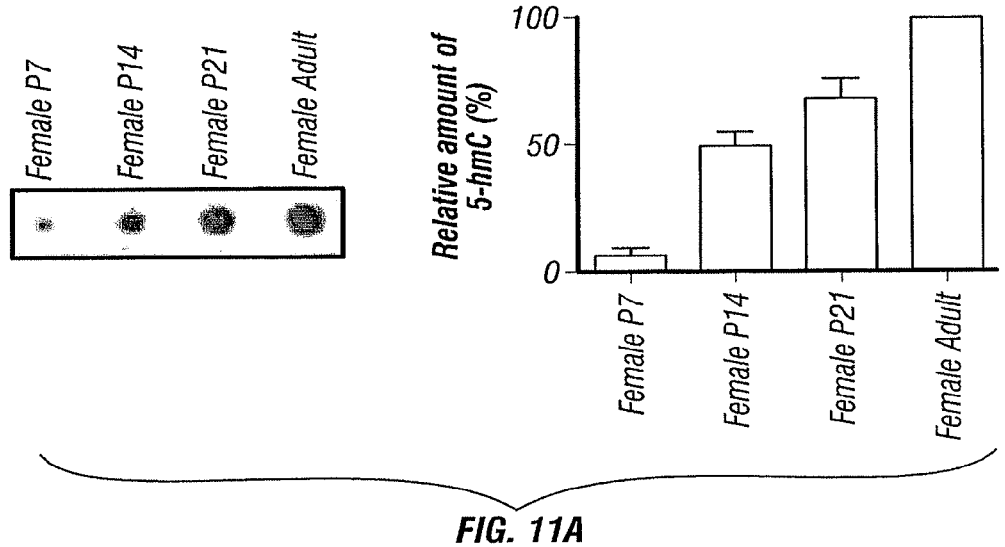
FIGS. 11A-11C. Validation of the 5-hmC labeling method by antibody and HRMS. (A), Dot-blot assay using anti-5-hmC antibody (Active Motif) with cerebellum genomic DNAs confirming an age-dependent accumulation of 5-hmC in mouse cerebellum. Quantification is shown on the right. (B), High resolution MS/MS CID spectrum (collision energy=15) of biotin-N3-5-gmC from the digestion of enriched HeLa genomic DNA labeled with biotin on 5-hmC. Structures are shown in the insets. Theoretical m/z values are shown; observed m/z values are also shown. Parent and fragment ion structures are shown in the panel. (C), MS/MS spectrum for $(M+2H)^{2+}$ of biotin-N3-5-gmC obtained from the digestion of enriched HeLa genomic DNA labeled with biotin on 5-hmC. Structures are shown in the insets. Theoretical m/z values and observed m/z values are shown.
Figure 11B:
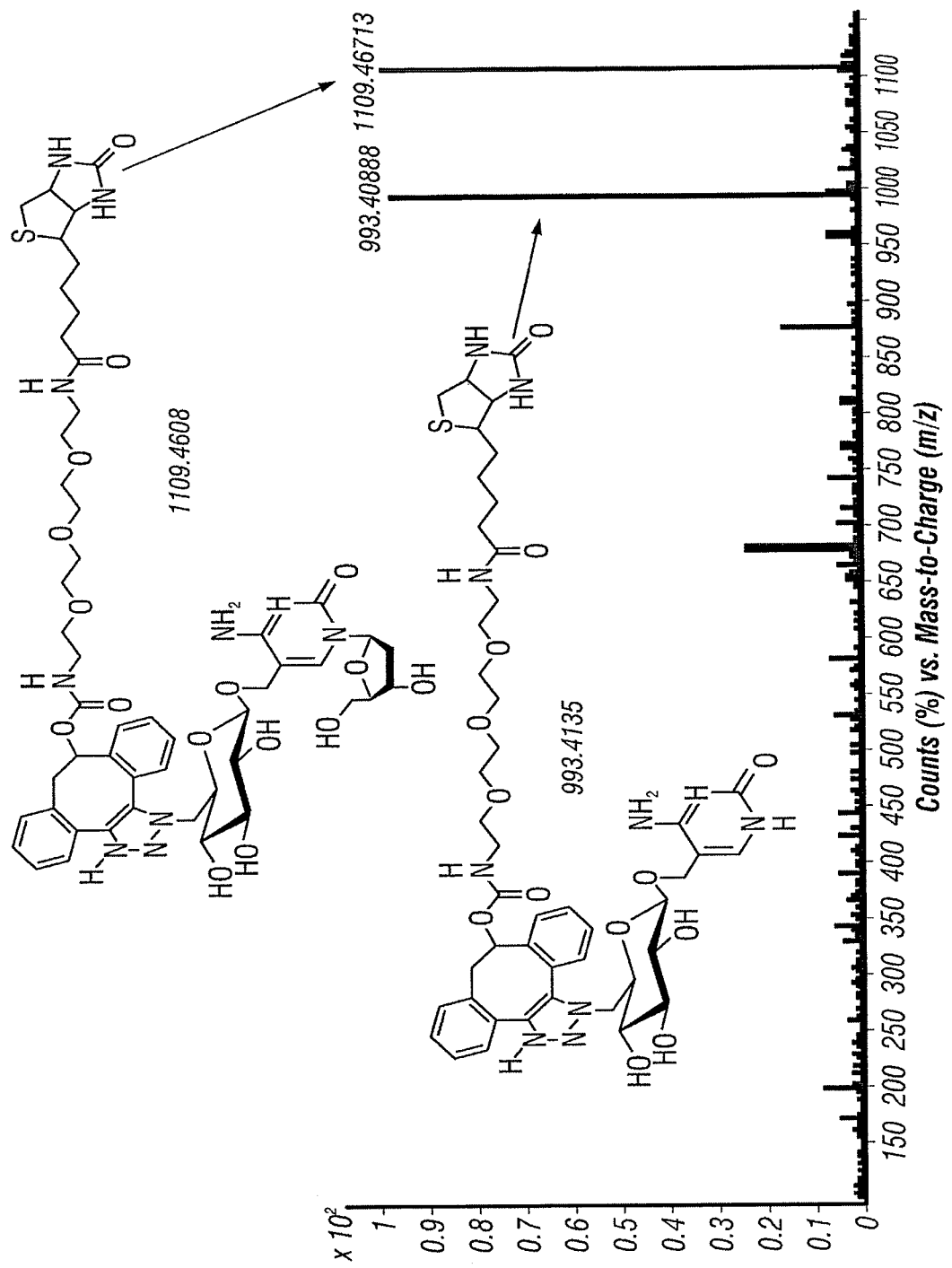
Figure 11C:
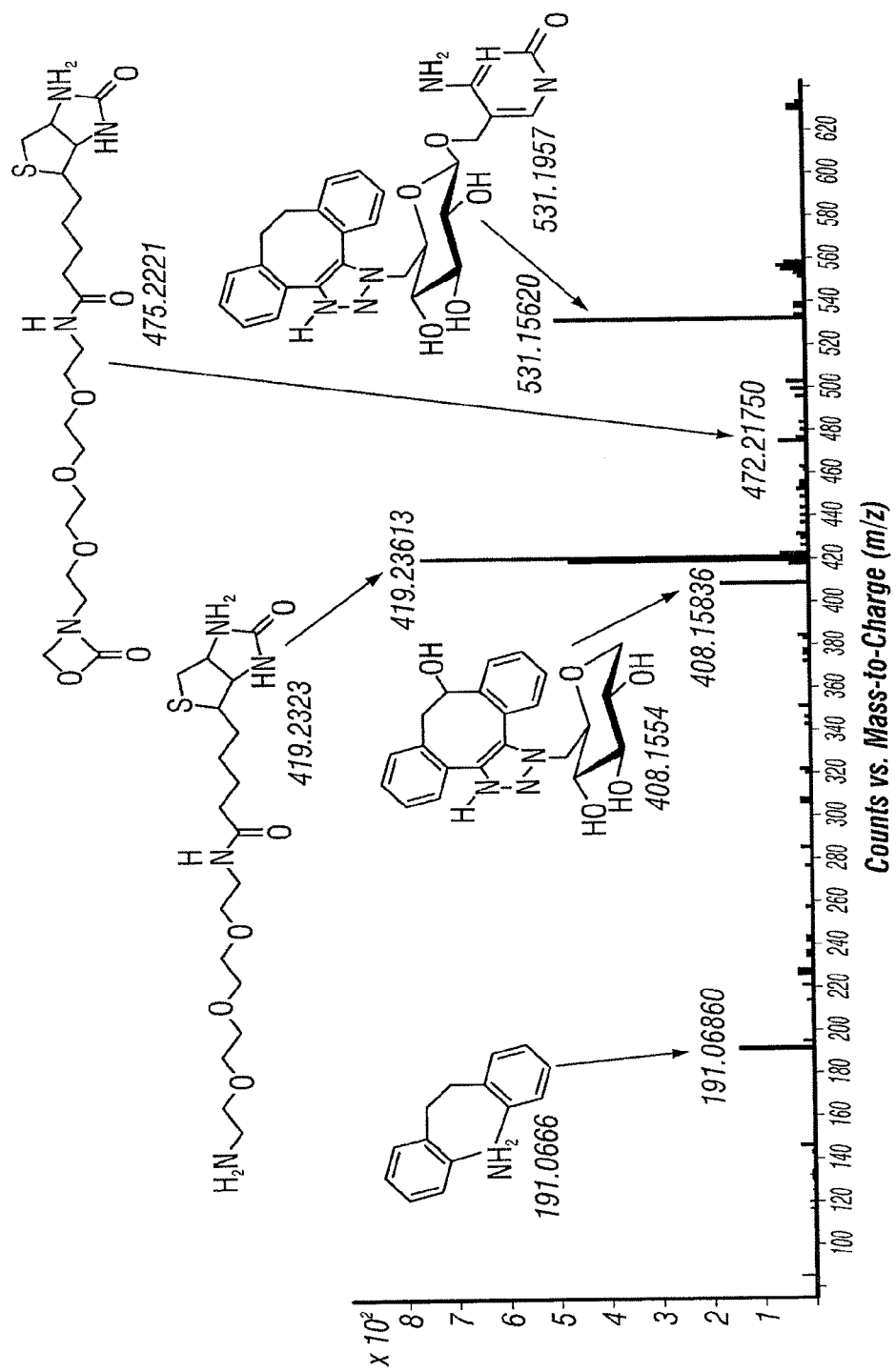

The inventors also tested human cell lines (FIGS. 10C and 10D). Notably, the presence of 5-hmC was detected in HeLa and HEK293FT cell lines, although in much lower abundance (~0.01% of total nucleotides) (FIG. 10D) than in other cells or tissues that have been previously reported to contain 5-hmC (previous studies did not show the presence of 5-hmC in HeLa cells due to the limited sensitivity of the methods employed (Kriaucionis and Heintz, 2009)). These results suggest that this modification may be more widespread than previously anticipated. By contrast, no 5-hmC signal was detected in wild-type Drosophila melanogaster, consistent with a lack of DNA methylation in this organism (Lyko et al., 2000).

Figure 12A:
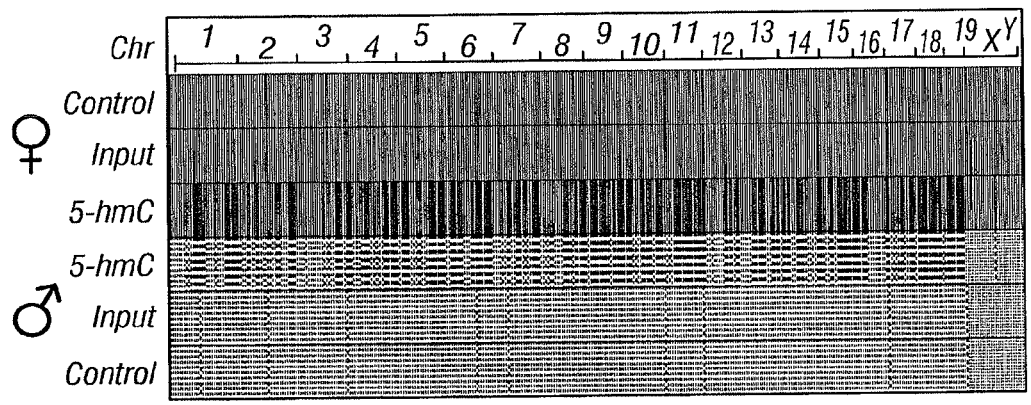
FIGS. 12A-12D. Genome-wide distribution of 5-hmC in adult mouse cerebellum and gene-specific acquisition of intragenic 5-hmC during mouse cerebellum development. (A) Genome-scale reproducibility of 5-hmC profiles and enrichment relative to genomic DNA and control-treated DNA in adult mouse cerebellum. Heatmap representations of read densities have been equally scaled and then normalized based on the total number of mapped reads per sample. Data are derived from a single lane of sequence from each condition. Control, UDP-Glu treated without biotin; Input, genomic DNA; 5-hmC, UDP-6-N3-Glu treated with biotin incorporated. (B) Metagene profiles of 5-hmC and input genomic DNA reads mapped relative to RefSeq transcripts expressed at different levels in adult mouse cerebellum. RefSeq transcripts were divided into four equally sized bins based on gene expression level and 5-hmC or input genomic DNA reads falling in 10-bp bins centered on transcription start sites or end sites. The reads were summed and normalized based on the total number of aligned reads (in millions). Input genomic DNA reads were mapped to each of the four gene expression level bins and are plotted here in black. The profiles completely overlap and so are collectively referred to as 'Input'. (C) Proximal and intragenic enrichment of 5-hmC relative to surrounding regions in adult and P7 mouse cerebellum. Reads from 5-hmC-captured samples and input genomic DNA were summed in 10-bp intervals centered on either TSS or txEnds and normalized to the total number of aligned reads from each sample (in millions). (D) Enrichment of pathways associated with age-related neurodegenerative diseases in genes acquiring intragenic 5-hmC in adult mice relative to P7 mice. Shown are the number of genes that acquired 5-hmC in adult cerebellum and the number of genes expected based on the total number of genes associated with that pathway in mouse. **, $P<10^{-10}$; *, $P<10^{-5}$.
Figure 12B:
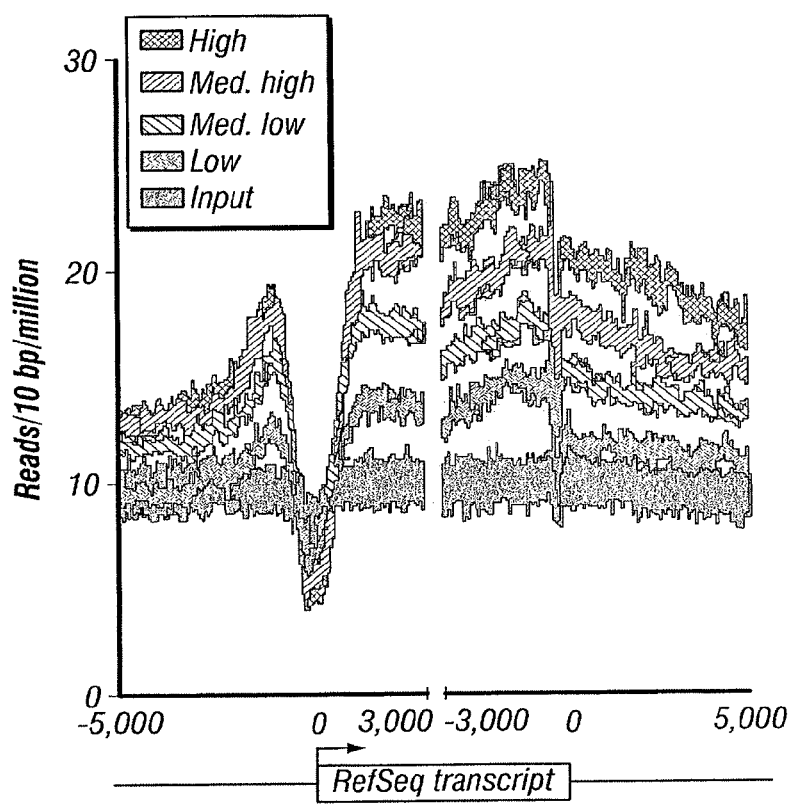
Figure 12C:
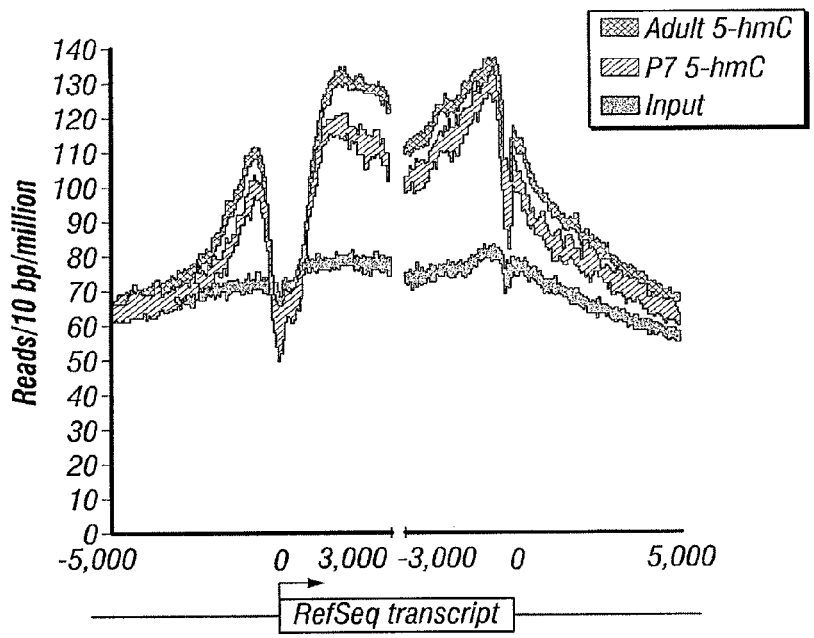
Figures 13A, 13B:
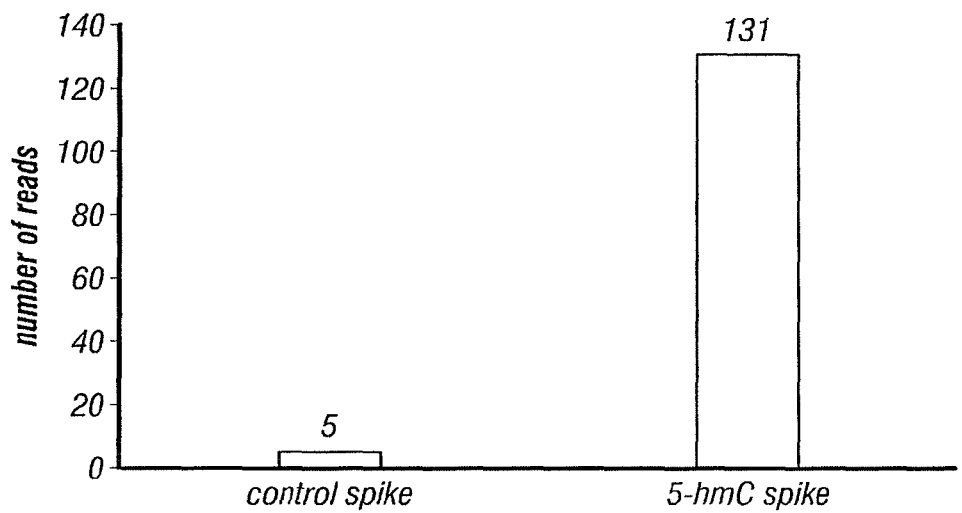
FIGS. 13A-13B. Reads mapping to 5-hmC and control spike. (A), Sequences of the 5-hmC spike and control spike. (B), Equal amount of two spikes were added into mouse genomic DNA. After 5-hmC labeling, enrichment and deep sequencing, reads mapping to the 5-hmC spike and the control spike are shown. There are total 131 reads mapped to 5-hmC spike and 5 reads mapped to the negative control, indicating that enrichment for 5-hmC was successful.

To further validate the utility of the method for biological samples the inventors confirmed the presence of 5-hmC in the genomic DNA from HeLa cells. A monomeric avidin column was used to pull down the biotin-N3-5-gmC-containing DNA after genomic DNA labeling. These enriched DNA fragments were digested into single nucleotides, purified by HPLC and subjected to HRMS analysis. The inventors obtained HRMS as well as MS/MS spectra of biotin-N3-5-gmC identical to the standard from synthetic DNA (FIG. 8, and FIGS. 12B and 12C). In addition, two 60-mer double-stranded (ds)DNAs, one with a single 5-hmC in its sequence and the other without the modification, were prepared. The inventors spiked equal amounts of both samples into mouse genomic DNA and performed labeling and subsequent affinity purification of the biotinylated DNA. The pull-down sample was subjected to deep sequencing, and the result showed that the 5-hmC-containing DNA was >25-fold higher than the control sample (FIG. 13).

Figure 14:
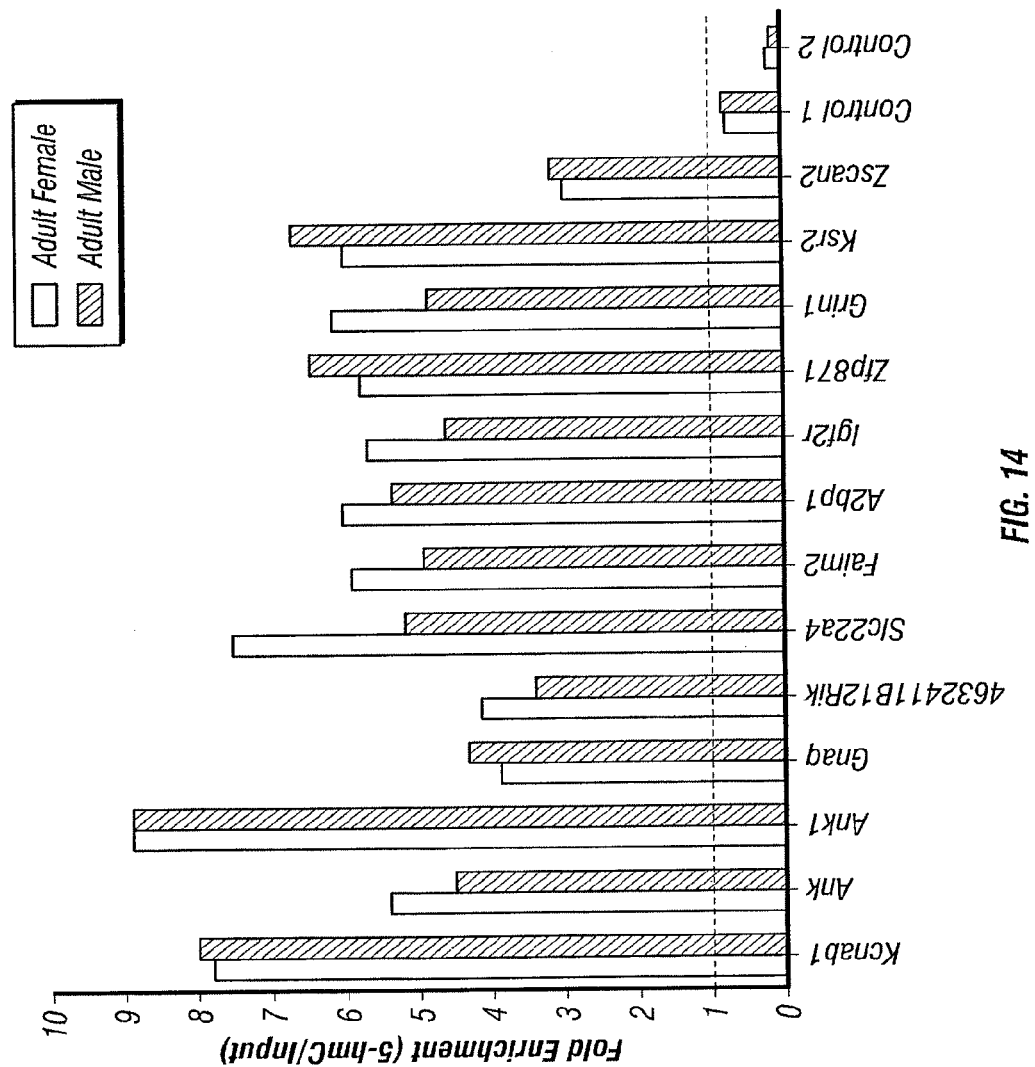
FIG. 14 Verification of 5-hmC-enriched regions by qPCR. Regions were identified as peaks in Adult Female relative to P7 and subsequently verified by qPCR in both Adult Female and Male. X-axis is labeled with the gene names within which the identified peak was identified. Fold Enrichment is calculated as $2^{-dCt}$, where dCt=Ct (5-hmC enriched)−Ct (Input).

The inventors performed chemical labeling of genomic DNA from mouse cerebellum, subjecting the enriched fragments to deep sequencing such that 5-hmC-containing genomic regions could be identified. Initially, the inventors compared male and female adult mice (2.5 months old), sequencing multiple independent biological samples and multiple libraries prepared from the same genomic DNA. Genome-scale density profiles are nearly identical between male and female and are clearly distinguishable from both input genomic DNA and control DNA labeled with regular glucose (no biotin) (FIG. 12A). Peak identification revealed a total of 39,011 high-confidence regions enriched consistently with 5-hmC in both male and female (FIG. 12A). All of the 13 selected, enriched regions were subsequently successfully verified in both adult female and male cerebellum by quantitative PCR (qPCR), whereas multiple control regions did not display enrichment (FIG. 14).

DNA methylation is widespread in mammalian genomes, with the exception of most transcription start sites (TSS) (Meissner et al., 2008; Lister et al., 2009; Edwards et al., 2010). Previous studies have mostly assessed DNA methylation by bisulfite sequencing and methylation-sensitive restriction digests. It has since been appreciated that neither of these methods adequately distinguishes 5-mC from 5-hmC (Huang et al., 2010; Jin et al., 2010). To determine the genome-wide distribution of 5-hmC, metagene 5-hmC read density profiles were generated for RefSeq transcripts. Normalized 5-hmC read densities differ by an average of $2.10\pm0.04\%$ (mean±s.e.m.) in adult male and female cerebellum samples, indicating that the profiles are accurate and reproducible. Enrichment of 5-hmC was observed in gene bodies as well as in proximal upstream and downstream regions relative to TSS, transcription termination sites (TTS) and distal regions (FIG. 12B). This is in contrast to previously generated methyl-binding domain-sequencing (MBD-Seq) (Skene et al., 2010), as well as our own methylated DNA immunoprecipitation sequencing (MeDIP-Seq) from mouse cerebellum genomic DNA, in which the majority (~80%) of 5-mC-enriched DNA sequences were derived from satellite and/or repeat regions (FIG. 15). Further analyses also reveal that both intragenic and proximal enrichment of 5-hmC is associated with more highly expressed genes, consistent with a role for 5-hmC in maintaining and/or promoting gene expression (FIG. 12B). Proximal enrichment of 5-hmC ~875 bp upstream of TSSs and ~160-200 bp downstream of the annotated TTSs further suggests a role for these regions in the regulation of gene expression through 5-hmC.

Quantification of bulk 5-hmC in the cerebellum of P7 and adult mice indicates genomic acquisition of 5-hmC during cerebellum maturation (FIG. 10A). The inventors further explored this phenomenon by sequencing 5-hmC-enriched DNA from P7 cerebellum and compared these sequences to those derived from adult mice. Metagene profiles at RefSeq transcripts confirmed an increase in proximal and intragenic 5-hmC in adult relative to P7 cerebellum, although there was little to no difference and minimal enrichment over input genomic DNA in distal regions (FIG. 12C). Peak identification using P7 as background identified a total of 20,092 enriched regions that showed significant differences between P7 and adult tissues. Of those, 15,388 (76.6%) occurred within 5,425 genes acquiring intragenic 5-hmC in adult females.

Figure 12D:
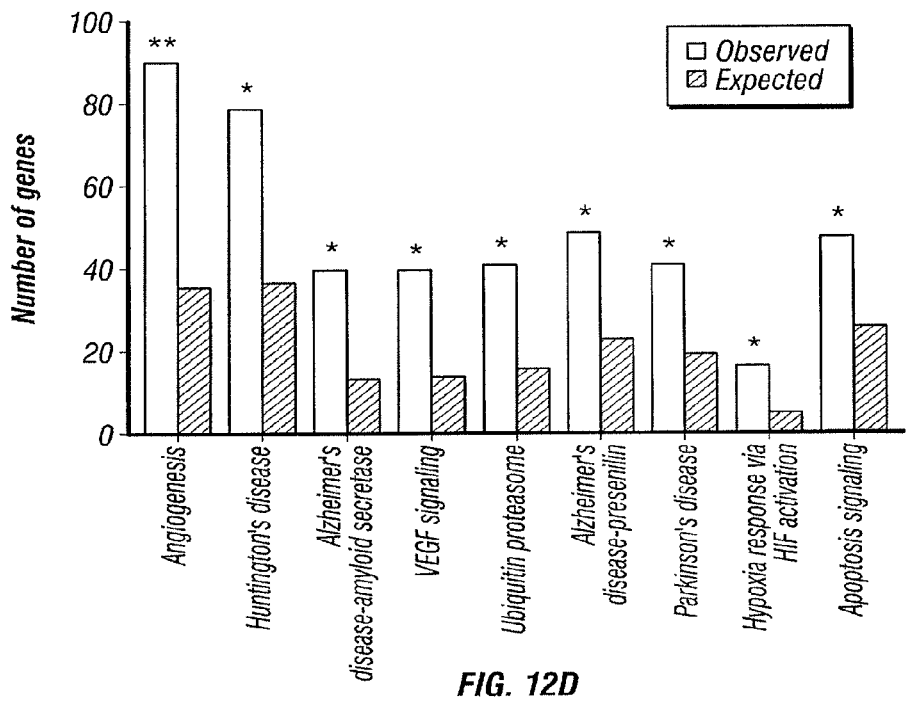

Gene ontology pathway analysis of the 5,425 genes acquiring 5-hmC during aging identified significant enrichment of pathways associated with age-related neurodegenerative disorders as well as angiogenesis and hypoxia response (FIG. 12D). This is of particular interest given that all these pathways have been linked to oxidation stress response and that the conversion of 5-mC to 5-hmC requires dioxygen. Furthermore, an assessment of the gene list revealed that 15/23 genes previously identified as causing ataxia and disorders of Purkinje cell degeneration in mouse and human acquired intragenic 5-hmC in adult mice (FIG. 16) (Lim et al., 2006). Together, these observations suggest that 5-hmC may play a role in age-related neurodegeneration.

Recently, β-GT was used to transfer a radiolabeled glucose for 5-hmC quantification (Szwagierczak et al., 2010). A major advantage of the technology described herein is its ability to selectively label 5-hmC in genomic DNA with any tag. With a biotin tag attached to 5-hmC, DNA fragments containing 5-hmC can be affinity purified for deep sequencing to reveal distribution and/or location of 5-hmC in mammalian genomes. Because biotin is covalently linked to 5-hmC and biotin-avidin/streptavidin interaction is strong and highly specific, this technology promises high robustness as compared to potential anti-5-hmC, antibody-based, immune-purification methods (Ito et al., 2010). Other fluorescent or affinity tags may be readily installed using the same approach for various other applications. For instance, imaging of 5-hmC in fixed cells or even live cells (if labeling can be performed in one step with a mutant enzyme) may be achieved with a fluorescent tag. In addition, the chemical labeling of 5-hmC with a bulky group could interfere with restriction enzyme digestion or ligation, which may be used to detect 5-hmC in specific genome regions. The attachment of biotin or other tags to 5-hmC also dramatically enhances the sensitivity and simplicity of the 5-hmC detection and/or quantification in various biological samples (Szwagierczak et al., 2010). The detection limit of this method can reach ~0.004% (FIG. 10D) and the method can be readily applied to study a large number of biological samples.

With the technology described herein, the inventors observed the developmental stage-dependent increase of 5-hmC in mouse cerebellum. Compared to postnatal day 7 at a time of massive cell proliferation in the mouse cerebellum, adult cerebellum has a significantly increased level of 5-hmC, suggesting that 5-hmC might be involved in neuronal development and maturation. Indeed, the inventors also observed an increase of 5-hmC in aNSCs upon differentiation (unpublished data).

This technology enables the selectively capture of 5-hmC-enriched regions in the cerebellums from both P7 and adult mice, and determine the genome-wide distribution of 5-hmC by deep sequencing. The inventor's analyses revealed general features of 5-hmC in mouse cerebellum. First, 5-hmC was enriched specifically in gene bodies as well as defined gene proximal regions relative to more distal regions. This differs from the distribution of 5-mC, where DNA methylation has been found both within gene bodies as well as in more distal regions (Meissner et al., 2008; Lister et al., 2009; Edwards et al., 2010; Maunakea et al., 2010). Second, the enrichment of 5-hmC is higher in gene bodies that are more highly expressed, suggesting a potential role for 5-hmC in activating and/or maintaining gene expression. It is possible that conversion of 5-mC to 5-hmC is a pathway to offset the gene repression effect of 5-mC during this process without going through demethylation (Wu and Zhang, 2010). Third, the inventors observed an enrichment of 5-hmC in genes linked to hypoxia and angiogenesis. The oxidation of 5-mC to 5-hmC by Tet proteins requires dioxygen (Tahiliani et al. 2009; Ito et al., 2010). A well-known oxygen sensor in mammalian systems that are involved in hypoxia and angiogenesis is the HIF protein, which belongs to the same mononuclear iron-containing dioxygenase superfamily as the active domain of the Tet proteins (Hausinger, 2004). It is tempting to speculate that oxidation of 5-mC to 5-hmC by Tet proteins may constitute another oxygen-sensing and regulation pathway in mammalian cells. Lastly, the association of 5-hmC with genes that have been implicated in neurodegenerative disorders suggests that this base modification could potentially contribute to the pathogenesis of human neurological disorders. Should a connection between 5-hmC levels and human disease be established, the affinity purification approach shown in the current work could be used to purify and/or enrich 5-hmC-containing DNA fragments as a simple and sensitive method for disease prognosis and diagnosis.

Construction, Expression and Purification of Wild-Type β-GT.

β-GT was cloned from the extract of T4 bacteriophage (American Type Culture Collection) into the target vector pMCSG19 by the ligation independent cloning method (Donnelly et al., 2006). The resulting plasmid was transformed into BL21 star (DE3)-competent cells containing pRK1037 (Science Reagents) by heat shock. Positive colonies were selected with 150 g/ml ampicillin and 30 g/ml kanamycin. One liter of cells was grown at 37° C. from a 1:100 dilution of an overnight culture. The cells were induced with 1 mM of isopropyl-β-d-thiogalactoside when OD600 reached 0.6-0.8. After overnight growth at 16° C. with shaking, the cells were collected by centrifugation, suspended in 30 ml Ni-NTA buffer A (20 mM Tris-HCl, pH 7.5, 150 mM NaCl, 30 mM imidazole and 10 mM β-mercaptoethanol) with protease inhibitor phenylmethylsulfonyl fluoride. After loading to a Ni-NTA column, proteins were eluted with a 0-100% gradient of Ni-NTA buffer B (20 mM Tris-HCl, pH 7.5, 150 mM NaCl, 400 mM imidazole and 10 mM β-mercaptoethanol). β-GT-containing fractions were further purified by MonoS (GE Healthcare) (buffer A: 10 mM Tris-HCl, pH 7.5; buffer B: 10 mM Tris-HCl, pH 7.5 and 1 M NaCl). Finally, the collected protein fractions were loaded onto a Superdex 200 (GE Healthcare) gel-filtration column equilibrated with 50 mM Tris-HCl (pH 7.5), 20 mM MgCl2 and 10 mM β-ME. The purity of the purified protein was determined by SDS-PAGE to be >95%. β-GT was concentrated to 45 μM and stored frozen at −80° C. with an addition of 30% glycerol.

βGT-Catalyzed 5-hmC Glycosylation in Duplex DNA.

The inventors synthesized the phosphoramidite of 5-hmC (now commercially available from Glen Research) and prepared duplex DNA with 5-hmC incorporated at specific locations. The inventors found that incubation of 5-hmC-containing duplex DNA (either 15 mer or 40 mer) with 10% purified βGT at 37° C. for 3 hours led to complete conversion of 5-hmC to 5-gmC, as judged by mass spectrometry analysis and digestion of DNA into single nucleosides for HPLC analysis. Primer extension and PCR experiments demonstrated that the presence of 5-gmC in DNA does not exhibit any interference to the polymerization reaction catalyzed by four different polymerases tested, and that guanine is incorporated into the complementary strand opposite 5-gmC. This result demonstrates that modification of 5-hmC with a molecule of glucose is not sufficient for use in primer extension and other polymerase-based assays to determine the exact location of this modification and that addition of much bulkier groups to 5-hmC using functionally modified glucose molecules is preferred.

A Restriction Enzyme Digestion-Based Method to Detect the Precise Locations of 5-hmC.

Figure 2:
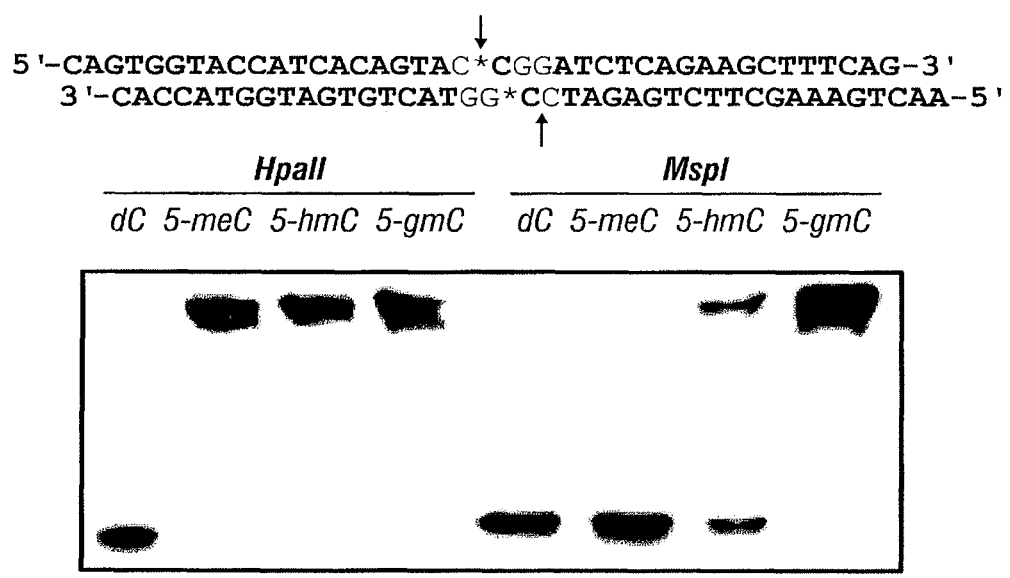
FIG. 2. Restriction enzyme digestion assay of a 40 mer DNA with CC*GG (where C*=C, 5-meC, 5-hmC, or 5-gmC). The 5-gmC modification in duplex DNA completely blocks the activity of the restriction enzyme MspI.

The inventors tested a restriction enzyme digestion assay with a 40-mer DNA containing a CC*GG (C*=C, 5-meC, 5-hmC, or 5-gmC) sequence in the middle. As expected, the methylation-sensitive restriction enzyme HpaII does not cut sequences containing 5-meC, 5-hmC, or 5-gmC. However, as shown in FIG. 2, while the methylation-insensitive restriction enzyme MspI can completely cut C(5-meC)GG and partially cut C(5-hmC)GG, its activity is completely blocked by C(5-gmC)GG. This indicates that the introduction of a glucose moiety can change the property of 5-hmC in duplex DNA. With bulkier groups on 5-hmC, digestions by other restriction enzymes that recognize DNA sequences containing CpG can be blocked.

Since 5-gmC can block restriction enzyme digestion, the genomic DNA modified with 5-gmC can be treated with and without restriction enzymes. The two samples can be subjected to next generation sequencing in order to map out the genome-wide distribution and location of the 5-hmC modification in the specific sequences recognized by corresponding restriction enzymes. Briefly, MspI-digested genomic DNA is ligated to a double-stranded adaptor with biotinylation on the upper strand. DNA is sheared further by partial nuclease digest, and size-selected for the 300-500 bp range. A second adaptor is then ligated onto ends that have not yet been filled by the first adaptor. Biotinylated fragments are then pulled down by streptavidin-coated beads, and denaturation will release single-stranded fragments flanked by both types of adaptors. These fragments are amplified by PCR for use in high-throughput sequencing. Internal MspI sites in the sequencing reads indicate resistance to MspI digest and hence the presence of 5-hmC at those sites. Bulky groups with modified glucose can be installed to interfere with other restriction enzymes.

Glycosylation of 5-hmC with Modified UDP-Glu, Including Azide-Substituted UDP-Glu.

Figure 3:
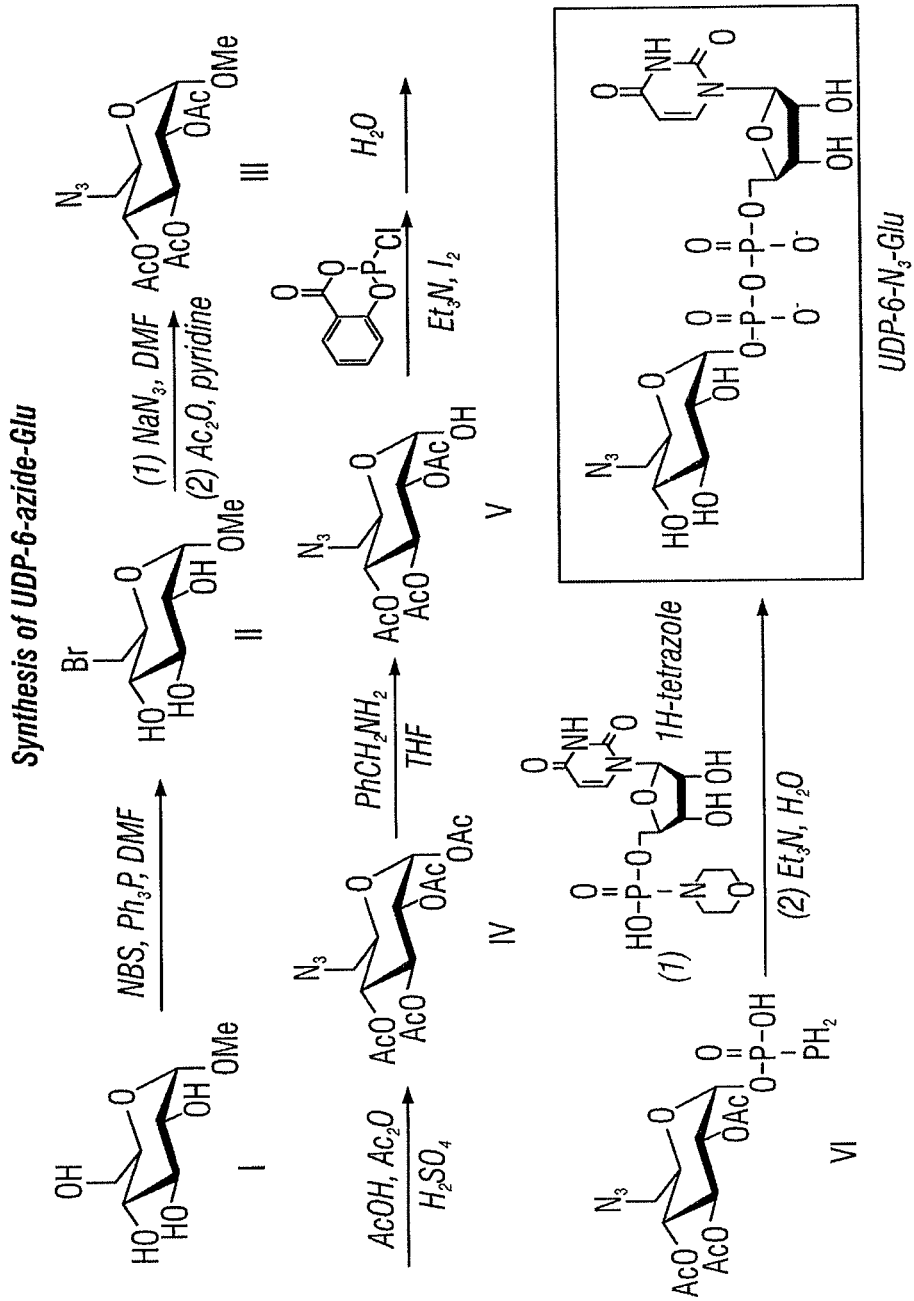
FIG. 3. Synthetic scheme for UDP-6-N3-UDP. The synthesis started from commercially available I. Treatment of I with NBS and Ph3P in DMF selectively afforded 6-bromo derivative II. Without isolation, treatment of II with sodium azide followed by acetylation of the hydroxyl groups in pyridine generated compound III. Conversion of the 1-MeO to the corresponding 1-OAc by treatment of III with acetic acid and acetic anhydride in the presence of sulfuric acid gave IV. Selective removal of the 1-α-acetyl protecting group with benzylamine provided compound V, which was converted to 1-α-phosphoric acid by treating V with 2-chloro-4H-1,3,2-benzodioxaphosphorin-4-one followed by hydrolysis and oxidation. The target molecule UDP-6-N3-UDP was obtained by treatment of VI with uridine 5-monophosphomorpholidate 4-morpholine-N,N-dicyclohexylcarboxamidine salt and tetrazole in pyridine and the subsequent treatment reaction with triethylamine and aqueous solution of NH4HCO3 in methanol to remove the acetyl groups. UDP-6-N3-UDP was purified by C18 reverse-phase HPLC and its structure was confirmed by 1H NMR, 13C NMR, 31P NMR, MALDI-TOF MS, and HRMS.

The structure of βGT with bound UDP-Glu has been solved and shows that the 6-hydroxyl group on the glucose of UDP-Glu is quite exposed on the protein surface with a water-filled channel located directly on top of it implying that modification of this 6-hydroxyl group may be modified to incorporate functional groups. The inventors have synthesized azide-substituted UDP-Glu (FIG. 3, Compound 8). The inventors have demonstrated that βGT can catalyze the transfer of 6-azide-glucose to 5-hmC-containing duplex DNA. The reaction with azide-substituted UDP-Glu proceeds as efficiently as with UDP-Glu. These results demonstrate that the azide substitution at this position can still be tolerated and recognized by βGT. Other substitutions at the same position of the azide are expected to be substrates for this reaction as well.

Biotination of 5-hmC in Genomic DNA for Affinity Purification and Sequencing.

The functional group installed on 5-gmC can be readily labeled with commercially available maleimide or alkyne (click chemistry) linked with a biotin, respectively. The reaction of thiol with maleimide is highly efficient; however, this labeling reaction cannot tolerate proteins or small molecules that bear thiol groups. Thus, genomic DNA must be isolated from other cellular components prior to the labeling, which can be readily achieved. The azide labeling with commercially available biotin-linked alkyne is completely bio-orthogonal, thus genomic DNA with bound proteins can be directly used. In both cases, the biotin-labeled DNA fragments may pulled down with streptavidin and submitted for high-throughput sequencing in order to map out global distributions and the locations of 5-hmC in chromosome. This will reveal a distribution map of 5-hmC in genomic DNA at different development stages of a particular cell or cell line.

Modified Bisulfate Sequencing Method.

Figure 4A:
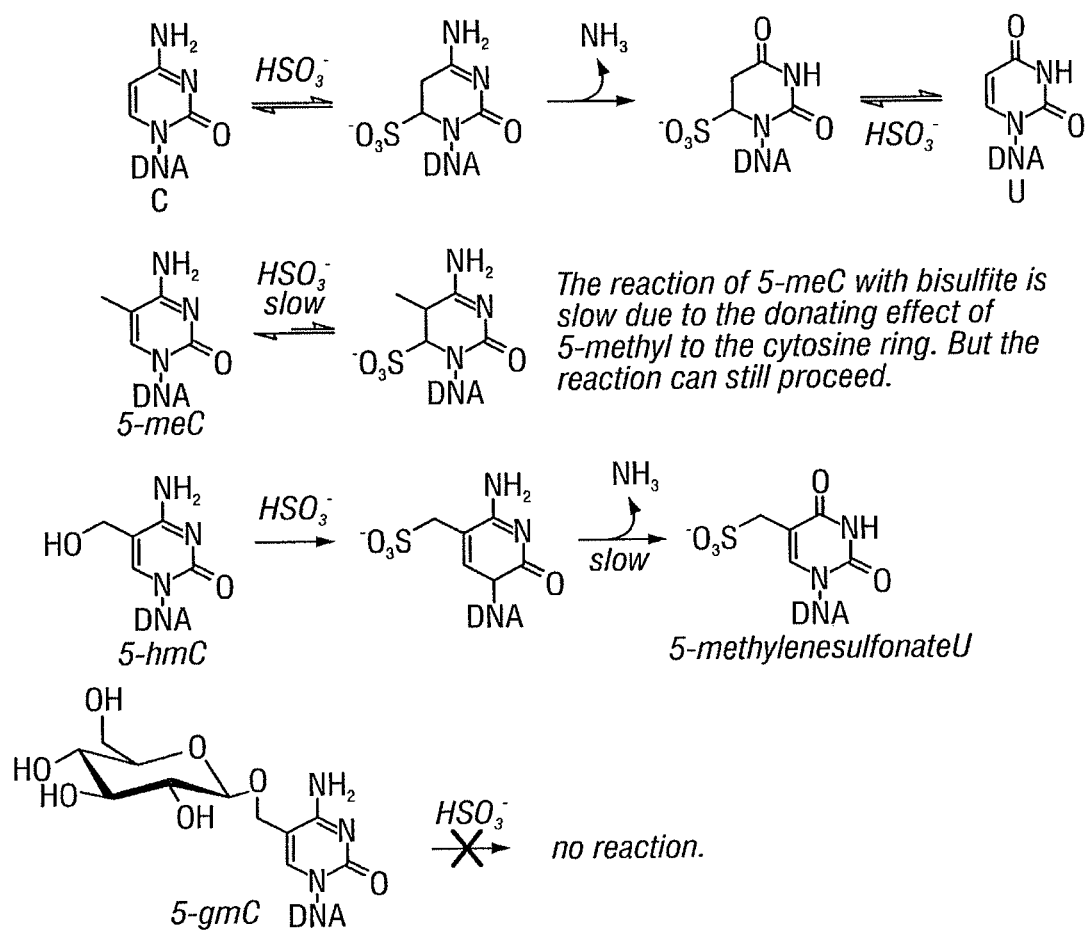
(FIG. 4A) Reactivity differences of 5-meC, 5-hmC, and 5-gmC to bisulfite can be exploited to differentiate 5-hmC or 5-gmC from 5-meC.
Figure 4B:
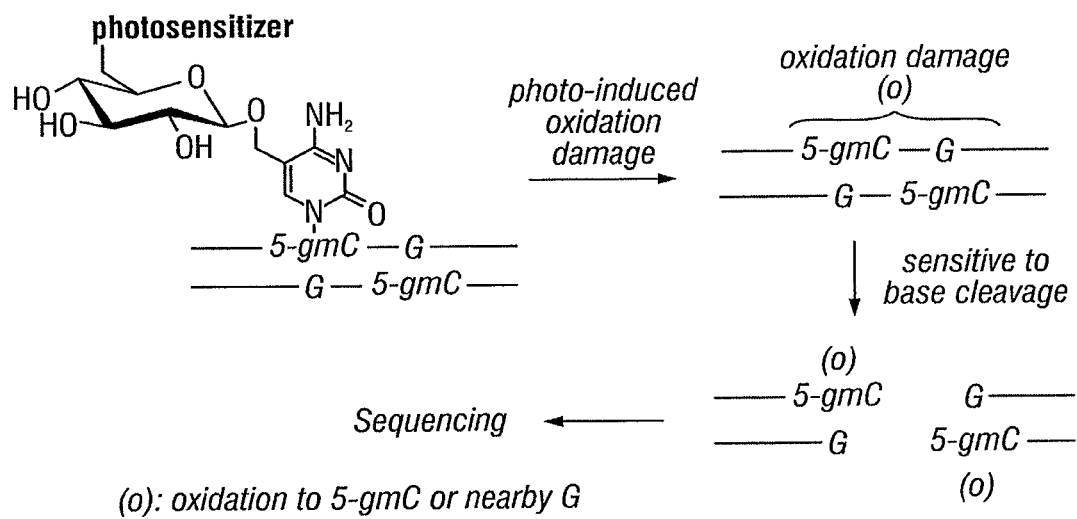
(FIG. 4B) A photosensitizer installed specifically on 5-gmC can lead to photosensitized oxidation of the labeled (5-gmC) pG, and subsequent base-mediated strand cleavage selective to this region.

5-meC in DNA reacts with bisulfite slowly, mostly due to the donating factor of the 5-methyl substitution to the cytosine ring (Hayatsu et al., 1970). Instead of attacking the 6-position of the cytosine, bisulfite actually reacts with the hydroxyl group of 5-hmC first. This process has been shown to be fast at pH 4.5 (Hayatsu and Shiragami, 1979). The resulting 5-methylenesulfonate cytosine deaminates slowly to afford 5-methlenesulfonate uracil (FIG. 4A). However, the 5-methylenesulfonate substitution renders this group less electronically donating compared to the methyl substitution. By varying the reaction temperature or pH, the inventors believe it is feasible to identify conditions in which bisulfite will react with 5-hmC, but not with 5-meC. Alternatively, at elevated temperature, both 5-meC and 5-hmC will react slowly with bisulfite. However, 5-gmC should be quite inactive since the sulfonation of the hydroxyl groups on the glucose will have minimum electronic effect on the cytosine ring. Through systematic variation of reaction conditions, a modified bisulfite sequencing method can be developed that allows the differentiation between 5-meC, 5-hmC, and 5-gmC.

Labeling 5-gmC with a Photosensitizer for High-Throughput Sequencing.

An alternative strategy that does not rely on converting 5-hmC:G base pair to a different base pair is to tether a photosensitizer to 5-gmC using approaches indicated in FIG. 1. Photosensitized one-electron oxidation can lead to site-specific oxidation of the modified 5-gmC or the nearby guanines (Tanabe et al., 2007; Meyer et al., 2003). Subsequent base (piperidine) treatment will lead to specific strand cleavage on the oxidized site (FIG. 4B) (Tanabe et al., 2007; Meyer et al., 2003). Thus, genomic DNA containing 5-gmC labeled with photosensitizer can be subjected to photo-oxidation and base treatment. DNA fragments will be generated with oxidation sites at the end. High-throughput sequencing will reveal these modification sites.

Attachment of a Sterically Bulky Group to 5-gmC.

In another strategy, a sterically bulky group such as polyethyleneglycol (PEG), a dendrimer, or a protein such as streptavidin can be introduced to the thiol- or azide-modified 5-gmC. Although 5-gmC in duplex DNA does not interfere with the polymerization reaction catalyzed by various different polymerases, the presence of an additional bulky group on 5-gmC on the DNA template strand can interfere with the synthesis of the new strand by DNA polymerase. As a result, primer extension will lead to a partially extended primer of certain length. The modification sites can be revealed by sequencing the partially extended primers. This method can be very versatile. It can be used to determine the modification sites for a given promoter site of interest. A high-throughput format can be developed as well. DNA fragments containing multiple 5-hmC can be affinity purified and random or designed primers can be used to perform primer extension experiments on these DNA fragments. Partially extended primers can be collected and subjected to high-throughput sequencing using a similar protocol as described in the restriction enzyme digestion method. A bulky modification may stop the polymerization reaction a few bases ahead of the modification site. Still, this method will map the modification sites to the resolution of a few bases. Considering that most 5-hmC exists in a CpG sequence, the resolution can be adequate for most applications. With a bulky substitution on 5-gmC digestion of modified DNA by restriction enzymes other than MspI could be blocked for the restriction enzyme digestion-based assay.

Applications in Embryonic Stem Cells and Neural Stem Cells.

To test the methods and to demonstrate their relevance to real biological situations, the inventors will apply them to the mapping of 5-hmC in several mammalian cell types. This involves two approaches. First, 5-hmC in mouse embryonic stem cells (ESCs) and fibroblasts are mapped. This would produces a general picture of how 5-hmC patterns compare and contrast between a pluripotent stem cell type and a terminally differentiated cell type. Second, 5-hmC is mapped in mouse neural stem cells (NSCs) as well as neurons and astrocytes derived via the differentiation of these NSCs. This elucidates how the process of lineage differentiation affects 5-hmC patterns.

These cell types have been selected to parallel a comprehensive set of whole-genome epigenetic studies, including the mapping of the methylome using bisulfite sequencing (which would not differentiate between 5-mC and 5-hmC), the transcriptome, and a variety of histone modifications implicated in gene regulation such as H3K4 acetylation, and H3K4, H3K9 and H3K27 methylation (Goldberg et al., 2007). Furthermore, it was also recently identified that a novel epigenetic state called "occlusion", whereby affected genes are silenced by cis-acting chromatin mechanisms in a manner that blocks them from responding the trans-acting transcriptional activators in the cell (Lee et al., 2009a; Lee et al., 2009b). Other labs are in the process of producing occludome maps (i.e., genome-wide maps of occluded genes) for the aforementioned cell types. Results from these comprehensive epigenetic studies would provide a highly informative context for interpreting the 5-hmC mapping data.

Affinity purified genomic DNA fragments enriched for 5-hmC as described in Example 3 can be directly subjected to high-throughput sequencing to identify these fragments.

Applications in Cancer Screening.

The redistribution of 5-meC in cancer cells is well documented across essentially every known human tumor type, and drugs that alter the DNA methylation state have become the standard of care for patients with myelodysplastic syndrome and hold promise for patients with other hematopoietic malignancies. Recently, mutations of the TET2 gene have been found in a variety of myelodysplastic syndromes, including in approximately 50% of cases of chronic myelomonocytic leukemia (CMML) (Abdel-Wahab et al., 2009; Kohlmann et al., 2009; Smith et al., 2009). The TET2 gene is closely related to TET1, which encodes an enzyme capable of converting 5-meC to 5-hmC, (Tahiliani et al., 2009) raising the issue that patients with CMML have altered content or distribution of 5hmC. Indeed, when lentiviruses have been used to increase the level of TET2 three-fold in leukemia cells, thin layer chromatography showed that 5-hmC content increased by 1.5-fold, and the bone marrow of patients with homozygous TET2 mutations showed a 20% decrease in 5-hmC levels (Szpurka et al., 2009).

These data suggest that alterations in TET2 levels influence the amount and/or location of 5-hmC within myeloid malignancies. To study this hypothesis, the inventors contemplate the use of the described methods to determine the precise location of 5-hmC bases within three cases of TET2-mutated CMML versus two CMML cases with wild-type TET2. Cases are identified using frozen tumor banks, which contain thousands of stored human leukemia samples. Cases of CMML are identified, and complete sequencing of the TET2 coding region is performed. Three cases of TET2-mutated CMML are chosen, giving preference to samples with a high disease burden (>85% bone marrow involvement) and with adequate cell numbers. For comparison, two cases of CMML will be analyzed that contain wild-type TET2. Determination of 5-hmC within these samples will allow the inventors to measure 5-hmC content as well as the precise location of this modified base. Of particular interest is to note whether the 5-hmC base occurs preferentially at promoter/CpG island/CpG shore regions, repetitive elements, or near centromeres, and whether 5-hmC is concentrated at particular chromosomes.

Labeling of 5-hmC in RNA Samples.

TET2 which is a homologue of TET1 modifies RNA. 5-hmC exist in human RNA. TET2 is defective in various leukemias (Abdel-Wahab et al., 2009).

Azide modified UDP-Glucose can be synthesized by the following reaction scheme.

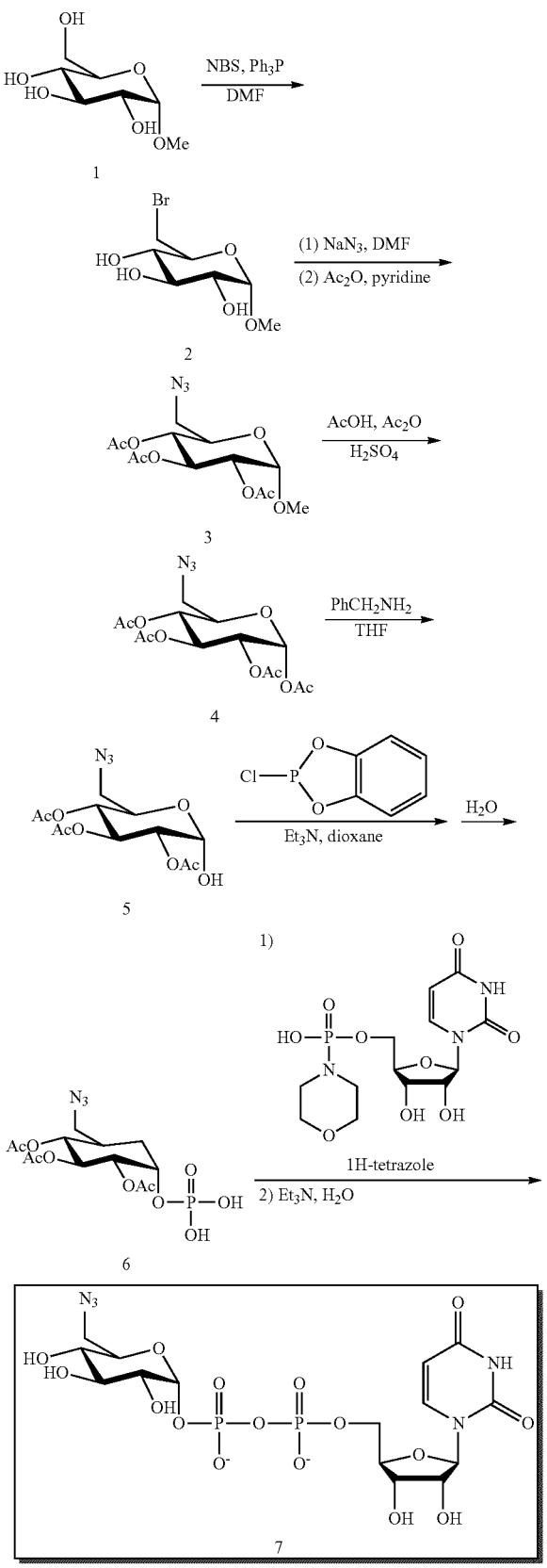

Scheme 1. Synthesis of 6-N₃-Glu-UDP (7)

Method used for the genomic DNA analysis can be divided into two general strategies. Initially genomic DNA is fragmented, for example by sonication or restriction enzyme digestion. After fragmentation 5-hmC in genomic DNA is detectably modified, for example using click chemistry after introduction of an azide-glucose. In a first strategy, the biotin-labeled DNA fragments will be pulled down using an avidin column. These affinity purified genomic DNA fragments are enriched for 5-hmC and will be directly subjected to high-throughput sequencing for sequence identification. This will give the global distribution map of 5-hmC in genomic DNA analyzed. Such analysis can be performed at different development stages or in various tissue or cell samples.

In a second strategy, biotin-labeled genomic DNA fragments the will be ligated to an adaptor with known sequence, then primer extension will then be performed in order to map out the exact location of 5-hmC.

Preparation of Genomic DNA.

All animal procedures were performed according to protocols approved by Emory University Institutional Animal Care and Use Committee. Genomic DNA from tissues and cell lines was purified using Wizard genomic DNA purification kit (Promega) with additional Proteinase K treatment and rehydrated in 10 mM Tris (pH 7.9). Genomic DNA samples were further sonicated in Eppendorf tubes into 100-500 bp by Misonix sonicator 3000 (using microtip, three pulses of 30 s each with 2 min of rest and a power output level of 2) or Bioruptor UCD-200 sonicator (Diagenode, Sparta). (The output selector switch was set on High (H), and sonication interval was 30 s with 30 cycles of sonication performed. In addition, samples were resuspended and centrifuged briefly every five cycles to keep the constancy of DNA shearing.) Cerebellums from P7 and 10-week-old C57BL/6 were used. Mouse feeder-free E14Tg2A ES cells (mESC) were cultured as reported (Silva et al., 2008). Adult neural stem cells (aNSCs) were isolated and cultured as described previously (Szulwach et al. 2010).

Accession codes. The sequencing data have been deposited in NCBI's Gene Expression Omnibus with accession number GSE25398.

Oligonucleotide Synthesis.

Oligonucleotides containing 5-hmC were prepared using Applied Biosystems 392 DNA synthesizer. 5-Hydroxymethyl-dC-CE phosphoramidite (Glen Research) was used to incorporate 5-hmC at the desired position during solid-phase synthesis, followed by postsynthetic deprotection by treatment with 30% ammonium hydroxide first and then 25-30% wt/wt solution of sodium methoxide in methanol (Alfa Aesar) overnight at 25° C. The 11-mer DNA was purified by reversed-phase HPLC and confirmed by MALDI-TOF. Other DNA was purified by denaturing PAGE. Concentrations of the oligonucleotides were estimated by UV at 260 nm. Duplexes were prepared by combining equimolar portions of the each strand in annealing buffer (10 mM Tris, pH 7.5, 100 mM NaCl), heating for 10 min at 95° C. followed by slow cooling overnight.

5-hmC Labeling Reaction and Click Chemistry.

The 5-hmC labeling reactions were performed in a 100-μl solution containing 50 mM HEPES buffer (pH 7.9), 25 mM $MgCl_2$, 300 ng/μl sonicated genomic DNA (100-500 bp), 250 μM UDP-6-N3-Glu, and 2.25 μM wild-type βGT. The reactions were incubated for 1 h at 37° C. After the reaction, the DNA substrates were purified by Qiagen DNA purification kit or by phenol-chloroform precipitation and reconstituted in $H_2O$. The click chemistry was performed with addition of 150 μM dibenzocyclooctyne modified biotin (compound 1) into the DNA solution, and the reaction mixture was incubated for 2 h at 37° C. The DNA samples were then purified by Qiagen DNA purification kit, which were ready for further applications.

Affinity Enrichment of the Biotinylated 5-hmC (Biotin-N3-5-gmC).

Genomic DNAs used for deep sequencing were purified/enriched by Pierce Monomeric Avidin Kit (Thermo) twice following manufacturer's recommendations. After elution, the biotin-N3-5-gmC containing DNA was concentrated by 10 K Amicon Ultra-0.5 ml Centrifugal Filters (Millipore) and purified by Qiagen DNA purification kit. Starting with 30 μg total genomic DNA, it is possible to obtain 100-300 ng enriched DNA samples following the labeling and pull-down protocol described here. The deep sequencing experiment can be performed with as low as 10 ng DNA sample.

The inventors have also developed a cleavable biotin-containing capture agent with a disulfide linker as the click reaction partner to form biotin-S-S-$N_3$-5-gmC (FIG. 21). The 5-hmC-containing DNA fragments from genomic DNA are captured by streptavidin beads, allowing non-modified DNA to be removed. A simple dithiothreitol (DTT) treatment releases the bound DNA fragments of interest with 5-hmC modified as HS-$N_3$-5-gmC (FIG. 21). This disulfide-reduction strategy to release desired DNA fragments is less time-consuming and more efficient than the previous monomeric avidin column-based purification method, increasing the pull-down efficiency by 2-3 fold. For comparison, pull-down yields of the previous method with mouse postnatal day 7 and mouse adult cerebellum genomic DNA were 0.46% and 1.3%, respectively, while the new method improved the yields to 1.6% and 3.1%, respectively.

Primer Extension Assay.

Reverse primer (14-mer, 5'-AAGCTTCTGGAGTG-3' (SEQ ID NO:2), purchased from Eurofins MWG Operon and PAGE purified) was end-labeled with T4 polynucleotide kinase (T4 PNK) (New England Biolabs) and 15 μCi of [γ-32P]-ATP (PerkinElmer) for 0.5 h at 37° C., and then purified by Bio-Spin 6 column (Bio-Rad). For primer extension assay, REDTaq DNA polymerase (Sigma) was used. The inventors first mixed 0.2 pmol template and 0.25 pmol γ-32P-labeled primers with dNTP in the polymerase reaction buffer without adding polymerase. The mixture was heated at 65° C. for 2 mM and allowed to cool slowly for 30 min. Streptavidin in PBS was then added if needed and allowed to mix at 25° C. for 5 mM. REDTaq DNA polymerase was then added (final volumn 20 μl) and the extension reaction was run at 72° C. for 1 min. The reaction was quenched by 2× stop solution (98% formamide, 10 mM EDTA, 0.1% xylene cyanol, 0.1% bromophenol blue) and loaded on to a 20% denaturing polyacrylamide gel (7 M urea). Sanger sequencing was performed using Sequenase DNA Sequencing Kit (USB) with 1 pmol template and 0.5 pmol [γ-32P]-labeled primer. The results were visualized by autoradiography.

Large-Scale HeLa 5-hmC Pull-Down.

Twenty dishes (15 cm) of HeLa cells were harvested and resuspended at 20 ml of 10 mM Tris (pH 8.0), 10 mM EDTA. Sodium dodecyl sulfate (SDS) and Proteinase K were added to final concentrations of 0.5% and 200 μg/ml, respectively, and the solution was allowed to incubate at 55° C. for 2 h. After adding NaCl to a final concentration of 0.2 M, the sample was extracted twice with equal volumes of phenol/chloroform/isoamyl alcohol (25:24:1) and once with chloroform. Chloroform was evaporated by placing the tube in 55° C. water bath for 1 h with cap open. RNase A was then added to a final concentration of 25 μg/ml and the solution incubated for 1 h at 37° C. DNA was then extracted once with phenol/chloroform/isoamyl alcohol (25:24:1) and once with chloroform and precipitated with 1.5 volumes of ethanol. Genomic DNA was washed twice with 20 ml of 70% ethanol, dried and resuspended in 10 mM Tris (pH 7.9) at 37° C. Genomic DNA was then sonicated by Bioruptor UCD-200 sonicator into 100-1,000 bp as noted before. The 5-hmC labeling reaction was carried out in a 4 ml solution containing 50 mM HEPES buffer (pH 7.9), 25 mM $MgCl_2$, 550 ng/μl sonicated HeLa genomic DNA, 250 μM UDP-6-N3-Glu and 2.25 μM wild-type β-GT. The reaction was incubated for 1 h at 37° C., purified by phenol-chloroform precipitation and reconstituted in 4 ml $H_2O$. The inventors added 20 μl of 30 mM dibenzocyclooctyne-modified biotin (compound 1) and incubated the mixture for 2 h at 37° C. The DNA sample was purified again by phenol-chloroform precipitation and then enriched for biotin-N3-5-gmC by monomeric avidin column as noted before. The pull-down DNA was concentrated and digested by nuclease P1 (Sigma), venom phosphodiesterase I (Type VI) (Sigma) and alkaline phosphatase (Sigma) according to published protocols (Crain, 1990). The sample was purified by HPLC C18 reversed-phase column as noted in FIG. 7. The peaks corresponding to the biotin-N3-5-gmC from synthetic DNA were collected, lyophilized and subjected to HRMS analysis. For HRMS analysis, lyophilized fractions were dissolved in 100 μl of 50% methanol and 5-20 μl samples were injected for LC-MS/MS analysis. The LC-MS/MS system is composed of an Agilent 1200 HPLC system and an Agilent 6520 QTOF system controlled by MassHunter Workstation Acquisition software (B.02.01 Build 2116). A reversed-phase C18 column (Kinetex C18, 50 mm×2.1 mm, 1.7 μm, with 0.2 μm guard cartridge) flowing at 0.4 ml $min^{-1}$ was used for online separation to avoid potential ion suppression. The gradient was from 98% solvent A (0.05% (vol/vol) acetic acid in MilliQ water), held for 0.5 min, to 100% solvent B (90% acetonitrile (vol/vol) with 0.05% acetic acid (vol/vol) in 4 min. MS and MS/MS data were acquired in extended dynamic range (1,700 m/z) mode, with post-column addition of reference mass solution for real time mass calibration.

Dot-Blot Assays and Quantification of Genomic DNA Containing 5-hmC.

Labeled genomic DNA samples (biotin-N3-5-gmC, 40 ng for mouse cerebellum samples, 700 ng for other samples) were spotted on an Amersham Hybond-N+ membrane (GE Healthcare). DNA was fixed to the membrane by Stratagene UV Stratalinker 2400 (auto-crosslink). The membrane was then blocked with 5% BSA and incubated with avidin-HRP (1:20,000) (Bio-Rad), which was visualized by enhanced chemiluminescence. Quantification was calculated using a working curve generated by 1-8 ng of 32 bp synthetic biotin-N3-5-gmC-containing DNA. Polyclonal antibody against 5-hmC (Active Motif) was also used for dot-blot assay (1:10, 000 dilution).

5-hmC-Enrichment Test.

Two solutions of 60-mer dsDNA (see FIG. 13) were prepared as noted. Mouse DNA (30 μg) was spiked with 3 pg from each DNA solution. The inventors did 5-hmC labeling and enrichment as noted. The pull-down DNA (10 ng) was end-repaired, adenylated, ligated to adapters (size selection 140-400 bp) and sequenced on an Illumina Genome Analyzer according to the manufacturer's recommendations for Illumina ChIP-Seq to identify spike enrichment.

Reads were mapped to the *Mus musculus* reference genome (NCBI37/mm9), excluding sequences that were not finished or that have not be placed with certainty (i.e., exclusion of sequences contained in the chrUN_random.fa and chrN_radom.fa files provided by the UCSC genome browser) and appended to contain fasta sequences corresponding to the positive and negative spiked controls. Sequence alignment was accomplished using bwa (Li and Durbin, 2009) and default alignment settings.

Deep Sequencing of Mouse Cerebellum Genomic DNA.

DNA libraries were generated following the Illumina protocol for "Preparing Samples for ChIP Sequencing of DNA" (Part#111257047 Rev. A). 25 ng genomic DNA, 5-hmC-captured DNA, or control captured DNA (in the absence of biotin) were used to initiate the protocol. In some instances <25 ng DNA was eluted in the no-biotin control treatment. In these cases the entire amount of eluted DNA was used to initiate library preparation. DNA fragments ~150-300 bp were gel purified after the adaptor ligation step. PCR amplified DNA libraries were quantified on an Agilent 2100 Bioanalyzer and diluted to 6 pM for cluster generation and sequencing. 38-cycle single end sequencing was performed using Version 4 Cluster Generation and Sequencing Kits (Part #15002739 and #15005236 respectively) and Version 7.0 recipes. Image processing and sequence extraction were done using the standard Illumina Pipeline.

Sequence alignment and peak identification. FASTQ sequence files were aligned to *Mus musculus* reference genome (NCBI37/mm9) using Bowtie (Langmead et al., 2009). The best alignment and reporting option was used for all conditions, corresponding to no more than 2 bp mismatches across each 38 bp read. 5-hmC peak identification was performed using nonduplicate reads with MACS (Zhang et al., 2008). Parameters were as follows: effective genome size=2.72e+09; tag size=38; band width=100; model fold=10; P value cutoff=1.00e−05; ranges for calculating regional lambda are: peak_region, 1,000, 5,000, 10,000.

For identification of high-confidence peaks consistently detected in adult female and male samples, data from all lanes were merged per condition (5-hmC enriched, nonenriched genomic DNA input) for each sex and used in the analysis described above. Using a combined input genomic DNA sequence set (male input plus female input) as background, 78.7% overlap in identified peaks were observed between male and female samples. As a more stringent analysis, the inventors also used sex-matched input genomic DNA as background/control samples for peak identification. A total of 91,751 peaks were identified in adult female cerebellum and a total of 240,147 peaks were identified in adult male cerebellum using these parameters; 39,011 peaks overlapped ≥1 bp by between sexes and are reported as the set of high-confidence peaks consistently detected adult cerebellum. Regions enriched for 5-hmC in adult cerebellum relative to P7 cerebellum were identified using a single lane of adult female 5-hmC reads as the treatment and the single lane of P7 reads as the background and/or control sample. A total of 20,092 regions were identified as enriched for 5-hmC in adult female cerebellum relative to P7 cerebellum. Of these, 15,388 (76.6%) were intragenic to 5,425 unique RefSeq transcripts. Genes acquiring 5-hmC during development are those with peaks overlapping ≥1 bp of a RefSeq gene.

Generation of Metagene Profiles and Heatmaps.

Metagene RefSeq transcript profiles were generated by first determining the distance between any given read and the closest TSS or TTS and then summing the number of 5'ends within 10 bp bins centered on either TSS or txEnds. Ten bp bins were then examined 5 kb upstream and 3 kb downstream to assess the level of 5-hmC in gene bodies relative to TSS and txEnds. The RefSeq reference file was obtained through the UCSC Genome Browser Tables (downloaded May 20, 2010).

Read densities (Reads/10bp) were calculated for each individual lane of sequence and then normalized per million reads of aligned sequence to generate a normalized read density.

For samples sequenced on multiple lanes, normalized read densities were averaged. To generate the metagene profile for adult cerebellum the inventors averaged normalized read densities from male and female. The inventors observed excellent consistency in normalized read densities between both technical replicates (independent library preparation and sequencing the same library on multiple lanes) as well as between biological replicates (male and female adult samples). For genomic DNA input libraries from male and female samples normalized read densities differed by 3.41±0.05% (mean±s.e.m.). For 5-hmC libraries from male and female samples normalized read densities differed by 2.10±0.04% (mean±s.e.m.).

To assess 5-hmC in genes expressed at different levels, the inventors obtained adult cerebellum gene expression data from the NCBI GEO sample GSM82974. Signal intensities were downloaded directly, divided into four bins of equal size, and converted into RefSeq mRNA IDs. The inventors then mapped 5-hmC reads to the TSS and txEnds as described above. Heatmap representations of sequence densities were generated using Integrated Genomics Viewer tools and browser (IGV 1.4.2, http://www.broadinstitute.org/igv) with a window size (-w) of 25 and a read extend (-e) of 200.

MeDIP-Seq, MBD-Seq Data and Analysis.

MBD-Seq data were downloaded from NCBI GEO number GSE19786, data sets SRR037089 and SRR037090 (Skene et al., 2010). Methyl cytosine containing DNA was immunoprecipitated as previously described (Szulwach et al., 2010) using 4 µg sonicated genomic DNA from adult female mouse cerebellum. The inventors used 25 ng immunoprecipitated DNA to generate libraries for sequencing as described above.

MeDIP-Seq and MBD-Seq reads were aligned to the NCBI37, mm9 using identical parameters as that used for 5-hmC reads. Using these parameters SRR037089 provided 15,351,672 aligned reads, SRR037090 provided 15,586,459 aligned reads and MeDIP-Seq provided 14,104,172 aligned reads. Reads were identified as either RepeatMasker (Rmsk, NCBI37, mm9) or RefSeq (based on May 20, 2010 UCSC download) if overlapping ≥1 bp of a particular annotation. The fraction of total reads corresponding to each was then determined. The expected fraction of reads based on the fraction of genomic sequence corresponding to either Rmsk or RefSeq was also plotted for comparison.

qPCR Validation of 5-hmC-Enriched Regions.

Input genomic DNA and 5-hmC enriched DNA were diluted to 1 ng/µl and 1 µl was used in triplicate 20 µl qPCR reactions each with 1× PowerSYBR Green PCR Master Mix (ABI), 0.5 µM forward and reverse primers, and water. Reactions were run on an SDS 7500 Fast Instrument using the standard cycling conditions. Primers were as follows, including the gene with which the identified peak associated the genomic location. Fold-enrichment was calculated as $2^{\wedge}-dCt$, where dCt=Ct (5-hmC enriched)−Ct (Input). Chr3: 65106415-65106915_Kcnab1: Forward (AAGCTATGC-CCGTGTCACTCA) (SEQ ID NO:3), Reverse (TGCAT-CAAGCGACACACAGA) (SEQ ID NO:4); Chr15: 27460605-27461105_Ank: Forward (ATCGGCAGAAGG-TAGGAGGAA) (SEQ ID NO:5), Reverse (CCTCACT-TGTCTCCCTGCTTATC) (SEQ ID NO:6); Chr8: 24136542-24137042_Ank1: Forward (GAGACCCTCT-TGGGACAGTTACC) (SEQ ID NO:7), Reverse (TGGGT-TACATTCCTCACTCGAA) (SEQ ID NO:8); Chr19: 16420423-16420923_Gnaq: Forward (ATGAGTGAAC-CATCCCATGCA) (SEQ ID NO:9), Reverse (TCAGC-CAGTGCCTCGTGAT) (SEQ ID NO:10); Chr1: 36417273-36417773_4632411B12Rik: Forward (TGCAACAAGTGCCTGACATACA) (SEQ ID NO:11), Reverse (TTGTGTGTGCAATCATTGTTCATT) (SEQ ID NO:12); Chr11: 53835569-53836069_Slc22a4: Forward (CCTCCAGTCCAGGCAGTGAT) (SEQ ID NO:13), Reverse (CGTCAAAGGAGTCCTGGTCAA) (SEQ ID NO:14); Chr15: 99352255-99352755_Faim2: Forward (CCTCCTTAGGGCCATTCTCAA) (SEQ ID NO:15), Reverse (CGGACCTGATGGGCATAGTAG) (SEQ ID NO:16); Chr16: 7197547-7198047_A2bp1: Forward (TC-TACTCCCGTTCACCGTFTATAT) (SEQ ID NO:17), Reverse (GCCCATGCAGCCAGTTG) (SEQ ID NO:18); Chr17: 12879263-12879763_Igf2r: Forward (AGAGGGA-CATGGGCATCACA) (SEQ ID NO:19), Reverse (AC-CGCTGACTGCCAGTACCT) (SEQ ID NO:20); Chr17: 32919340-32919840_Zfp871: Forward (GACCCAG-GAGAGAAAGCATGAG) (SEQ ID NO:21), Reverse (TGACTCCGTGAACAGGAATGG) (SEQ ID NO:22); Chr2: 25147087-25147587_Grin1: Forward (AGAGAGATAGAGGTGGAAGTCAGGTT) (SEQ ID NO:23), Reverse (AGGAGCCTGGAGCAGAAATG) (SEQ ID NO:24); Chr5: 117916917-117917417_Ksr2: Forward (GAACAGTGTAAGGTCCACCCAAGT) (SEQ ID NO:25); Reverse (GGAAAAACGGGTTCGGAAAG) (SEQ ID NO:26); Chr7: 88013448-88013948_Zscan2: Forward (TG-GCACACTTGAGCAAATCCTA) (SEQ ID NO:27); Reverse (TGCCAACTATTGGAATGGAAAATA) (SEQ ID NO:28); Control primers: Chr17: 31829767-31830267_Control1: Forward (GAACAGCCAGCAACCTTCTAAAA) (SEQ ID NO:29), Reverse (CAACAGCGTCATGG-GATAACA) (SEQ ID NO:30); Chr12: 98299598-98300098_Control2: Forward (ACAACCCGCCCAC-CAAT) (SEQ ID NO:31, Reverse (TTTAGCTACCCCCAAGTTTAATGG) (SEQ ID NO:32).

GO Pathway Analysis.

Peaks enriched for 5-hmC in adult female relative to P7 were overlapped with RefSeq annotations and those overlapping ≥1 bp were retained. A unique set of genes with ≥1 enriched 5-hmC region was then generated and used as input for the binomial gene list comparison tool provided by the Protein Analysis Through Evolutionary Relationships (PANTHER) classification system (Thomas et al., 2003; Thomas et al., 2006).

Chemical Synthesis.

Compound 1 was prepared according to previous literatures (Ning et al., 2008; Jung and Miller, 1981). UDP-6-N3-UDP was chemically synthesized, see Song et al, 2011.

Statistical Methods.

The inventors used unpaired two-tailed Student's t-tests (assuming equal variance) to determine significance and calculate P-values between mouse samples of different age. A minimum of three data points was used for each analysis.

Synthesis of Modified Uridine Diphosphate Glucose (UDP-Glu) Bearing Thiol or Azide.

The initial success of 5-hmC glycosylation led to the hypothesis that thiol- or azide-modified glucose can be similarly transferred to 5-hmC in duplex DNA. Thus, the inventors have synthesized azide-substituted UDP-Glu and expect to synthesize thiol-substituted UDP-Glu for 5-hmC labeling. An azide tag is preferred since this functional group is not present inside cells. The click chemistry to label this group is completely bio-orthogonal, meaning no interference from biological samples (Kolb et al., 2001). An azide-substituted UDP-Glu shown in FIG. 3. The azide-substituted glucoses can be transferred to 5-hmC, as shown below.

Methyl 2,3,4-tri-O-acetyl-6-azido-6-deoxy-α-D-glucopyranoside (III)

To a solution of methyl-α-D-glucopyranoside (I, 1.0 g, 5.14 mmol), triphenylphosphine (2.72 g, 10.3 mmol) in DMF (30 mL) and NBS (1.84 g, 10.3 mmol) were added and the mixture was stirred at 60° C. for 2 hr. Methanol (1 mL) was added to quench the reaction and sodium azide (2.0 g, 30 mmol) was added and the mixture was heated at 80° C. for 4 hr. Solvents were removed under the reduced pressure and the resulting residue was dissolved in water and washed with 1:1 chloroform-hexane. The water phase was then evaporated to dryness and the resulting residue was suspended in acetone. Filtration removed the solid and the filtrate was evaporated to dryness. Pyridine (10 mL) and acetic anhydride (2 mL) was added and the mixture was stirred overnight at room temperature (rt). Methanol (2 mL) was added to quench the reaction. Solvents were removed under the reduced pressure and the resulting residue was dissolved in dichloromethane and washed with 5% $NaHCO_3$ and brine, dried over sodium sulfate and concentrated. The residue was purified by silica gel chromatography, eluting with 2% methanol in dichloromethane, to give III (1.24 g, 70%) as a white foam. $^1H$ NMR (500.1 MHz) (CD3Cl) δ: 5.41 (t, J=12.5 Hz, 1H), 4.81-4.96 (m, 3H), 3.91 (m, 1H), 3.40 (s, 3H), 3.26 (m, 2H), 2.02 (s, 3H), 1.98 (s, 3H), 1.95 (s, 3H).

1,2,3,4-tetra-O-acetyl-6-azido-6-deoxy-α-D-glucopyranose (IV)

To a solution of methyl 2,3,4-tri-O-acetyl-6-azido-6-deoxy-α-D-glucopyranoside (III, 1.0 g, 2.9 mmol) in acetic acid (20 mL) and acetic anhydride (20 mL) at 0° C. was added sulfuric acid (97%, 1 mL) and the mixture was stirred at rt for 20 hr and then poured into ice (100 g). Extraction with dichloromethane (3×50 mL) and washed with water, saturated sodium bicarbonate, brine, dried over sodium sulfate and concentrated. The residue was purified by silica gel chromatography, eluting with 1:1 hexane-ethyl acetate, to give IV (886 mg, 82%) as a white foam. $^1H$ NMR (500.1 MHz) (CD3Cl) δ: 6.28 (d, J=4.0 Hz, 1H), 5.41 (t, J=9.5 Hz, 1H), 5.03 (m, 2H), 4.03 (m, 1H), 3.24-3.37 (m, 2H), 2.13 (s, 3H), 2.04 (s, 3H), 1.99 (s, 3H), 1.95 (s, 3H). 13C NMR (125.8 MHz) (CDCl3) δ: 170.11, 169.53, 169.33, 168.62, 88.78, 70.83, 69.58, 69.08, 68.94, 50.61, 20.75, 20.55, 20.46, 20.34.

2,3,4-tri-O-acetyl-6-azido-6-deoxy-α-D-glucopyranose (V)

To a solution of 1,2,3,4-tetra-O-acetyl-6-azido-6-deoxy-α-D-glucopyranose (IV, 850 mg, 2.78 mmol) in THF (12 mL) was added benzylamine (0.23 mL) and the mixture was stirred at rt overnight. Solvents were removed under the reduced pressure and the resulting residue was dissolved in dichloromethane (50 mL) and washed with water, saturated ammonia chloride, brine, dried over sodium sulfate and concentrated. The residue was purified by silica gel chromatography, eluting with 1:1 hexane-ethyl acetate, to give V (640 mg, 85%) as a white foam. $^1H$ NMR (500.1 MHz) (CD3Cl) δ: 5.50 (m, 2H), 5.03 (t, J=10.5 Hz, 1H), 4.90 (m, 1H), 4.24 (m, 1H), 3.35 (m, 2H), 2.12 (s, 3H), 2.05 (s, 3H), 2.02 (s, 3H). 13C NMR (125.8 MHz) (CDCl3) δ: 170.26, 170.23, 169.78, 89.98, 71.09, 69.71, 68.34, 51.05, 20.68, 20.62, 20.58.

2,3,4-tri-O-acetyl-6-azido-6-deoxy-α-D-glucopyranosyl phosphate mono-triethylamine salt (VI)

To a solution of 2,3,4-tri-O-acetyl-6-azido-6-deoxy-α-D-glucopyranose (V, 390 mg, 1.18 mmol) in diethyl ether at 0° C. triethylamine (1 mL) was added followed by 2-chloro-4H-1,3,2-benzodioxaphosphorin-4one (239 mg). After stirring at 0° C. for 1 hr, water (1 mL) was added and the mixture was concentrated. The residue was dissolved in THF (20 mL) and the generated precipitant was separated by filtration. The filtrate was passed through a cation-exchange resin column with additional THF. The filtrate was concentrated. To a solution of the resulting oil in THF was added iodine (100 mg) and the mixture was stirred at rt for 24 hr and triethylamine was added to neutralize the solution to pH=7. The concentrate was purified by a C18 reverse-phase column to give the phosphate VI. $^1H$ NMR (500.1 MHz) (CD$_3$OD) δ: 5.75 (dd, J=9.5, 4.0 Hz, 1H), 5.52 (m, 1H), 5.14 (t, J=12.0 Hz, 1H), 4.89 (m 1H), 4.29 (m 1H), 3.60 (dd, J=17.0, 4.0 Hz, 1H), 3.34 (m, 2H), 3.20 (q, 6H), 2.07 (s, 3H), 2.04 (s, 3H), 2.01 (s, 3H). 31P NMR (202.5 MHz) (CD3OD) δ: −0.94.

Uridine 5'-(2,3,4-tri-O-acetyl-6-azido-6-deoxy-α-D-glucopyranosyl)diphosphate bistriethylammonium salt (UDP-6-N3-UDP)

2,3,4-Tri-O-acetyl-6-azido-6-deoxy-α-D-glucopyranosyl phosphate mono-triethylamine salt (VI, 23 mg, 0.045 mmol) was co-evaporated with dry pyridine (5 mL) for three times under reduced pressure. Uridine 5'-monophosphomorpholidate 4-morpholine-N,N'-dicyclohexylcarboxamidine salt (77 mg) and tetrazole (250 µL, 0.45M) were added and the mixture was co-evaporated with dry pyridine (5 mL) for three times under reduced pressure. The residue was dried in vacuum for overnight and was added distilled pyridine (5 mL). The mixture was stirred at rt under argon atmosphere. After three days, pyridine was removed under reduced pressure and the residue was co-evaporated with toluene. The residue was then added with methanol (3.4 mL), aqueous solution of $NH_4HCO_3$ (0.1 M, 4.5 mL) and triethylamine (0.18 mL) and the mixture was stirred at 0 for 24 hr. Then water (20 mL) was added and pH was adjusted to 7.5 with DOWEX 50W (H+ form) resin. The resin was removed by filtration through a PTFE filter and the resin was washed with water (10 mL). After concentration, the product was purified by C18 reverse-phase HPLC, eluting with 0-20% $CH_3CN$ in 0.1 M TEAA. $^1H$ NMR (500.1 MHz) (D2O) δ: 7.85 (d, J=8.0 Hz, 1H), 5.85 (m, 2H), 5.46 (m, 1H), 4.09-4.66 (m, 7H), 3.63 (m, 2H), 3.43 (m, 2H), 3.37 (Et3NHOAc), 1.78 (Et3NHOAc), 1.15 (Et3NHOAc). 13C NMR (125.8 MHz) (D2O) δ: 181.46 (Et3NHOAc), 166.30, 151.87, 141.61, 102.66, 95.47, 88.38, 83.22, 73.78, 72.66, 71.62, 69.78, 69.61, 64.90, 50.53, 46.68 (Et3NHOAc), 23.25 (Et3NHOAc), 8.22 (Et3NHOAc). 31P NMR (202.5 MHz) (D2O) δ: −10.69 ppm (d, J=20.65 Hz) and −12.49 ppm (d, J=21.01 Hz). HRMS (ESI, negative mode) for C49H57N4NaO9P, [M-H]−: 590.0542 (calcd.); 590.0523 (found).

Example 2

Detection of 5-Hydroxymethylcytosine in a Combined Glycosylation Restriction Analysis (CGRA) Using Restriction Enzyme Taq$^α$I Here the inventors describe an example of using of a methylation-insensitive restriction enzyme coupled with selective chemical labeling of 5-hmC in a Combined Glycosylation Restriction Analysis (CGRA) to detect 5-hmC in TCGA sequences. This example provides a proof of principle demonstration using the methylation-insensitive restriction enzyme Taq$^α$I. This method, differentiates fully versus hemi-hydroxymethylated cytosine in the CpG dinucleotide, adds a new tool to facilitate biological studies of 5-hmC.

As described herein, the inventors developed a chemical labeling method to selectively label 5-hmC with glucose by β-glucosyltransferase (βGT), e.g., an azide modified glucose. The glucose is subsequently coupled to a probe that allows detection of 5-hmC in genomic DNA (Song et al., 2011). With this method, 5-hmC-containing genomic DNA fragments can be enriched and sequenced to provide the genomic distribution of this modification.

The use of methylation-sensitive restriction enzymes is a classic approach to the study of DNA methylation at specific loci (Singer-Sam et al., 1990). However, due to the similar size of the methyl and hydroxymethyl groups, 5-mC and 5-hmC are indistinguishable to most restriction enzymes (Jin et al., 2010; Nestor et al., 2010; Tardy-Planechaud et al., 1997; Szwagierczak et al., 2011). The inventors contemplated that after adding the bulky glucose group or a subsequent biotin attachment to 5-hmC, the glucosylated base would have different properties from 5-mC (Huang et al., 1982). For example, the resulting 5-$N_3$-gmC or biotin-5-$N_3$-gmC in a duplex DNA may be able to block digestion from the methylation-insensitive restriction enzyme, which can digest both 5-hmC- and 5-mC-containing DNA. Zymo Research and New England Biolabs have launched products based on this combined glycosylation restriction analysis (CGRA). They utilize βGT to transfer a regular glucose to 5-hmC and show that it can block the methylation-insensitive restriction enzyme MspI, which has a recognized sequence of C^CGG (Davis and Vaisvila, 2011). Although the use of MspI in CGRA can detect the presence of 5-hmC on CCGG site, it has several limitations: (i) MspI is also blocked if the outer C is 5-mC or 5-hmC, regardless of the cytosine modification status of the inner C, which limits the use of this approach on many CCGG sites where the outer C methylated (Tardy-Planechaud et al., 1997); (ii) it cannot tell whether 5-hmC occurs on only one strand or both strands of the CpG dinucleotide. The inventors demonstrate that Taq$^{\alpha}$I, another methylation-insensitive restriction enzyme that recognizes and cuts T^CGA, can also be used in CGRA when coupled with our chemical labeling method. This new approach can differentiate fully versus hemi-hydroxymethylated states in the CpG dinucleotide.

The inventors first synthesized a 32-mer double strand DNA bearing T*CGA (*C=5-hmC) on both strands (FIG. 19A). Instead of glucose, inventors employed βGT to transfer chemically modified 6-$N_3$-glucose, onto 5-hmC. Then the modified DNA was subjected to Taq$^{\alpha}$I-mediated digestion. Taq$^{\alpha}$I can completely cut unmodified 5-hmC, but only partially for $N_3$-5-gmC. (FIG. 19A, lane 1-4) (Huang et al., 1982). The relatively high tolerance of Taq$^{\alpha}$I to the cytosine modification requires more bulky modifications in order to achieve a satisfactory difference in CGRA. The presence of azide group on the glucose allows the further addition of modifications by using click chemistry (Rostovtsev et al., 2002; Sletten et al., 2009; Speers and Cravatt, 2004). $N_3$-5-gmC was coupled with dibenzocyclooctyne-modified biotin using copper-free click chemistry to introduce a sterically bulky dibenzocyclooctyne moiety (FIG. 18) (Ning et al., 2008; Jewett and Bertozzi, 2010). When the inventors introduced the biotin-$N_3$-5-gmC modification into Taq$^{\alpha}$I digestion, it showed an almost complete blocking effect (FIG. 19A, lane 5-6).

Due to the semi-conservative DNA replication, besides a full methylation state, hemi-methylation state also exists in mammalian genome. The conversion of 5-mC to 5-hmC suggests that fully and hemi-hydroxymethylation states may also exist in the mammalian genome. If this is the case, developing a method to distinguish between these two states can be used to understand the formation of 5-hmC and conversion process between 5-mC and 5-hmC. Since the blocking efficiency of Taq$^{\alpha}$I is largely dependent on the size of the modification group on the hydroxyl group, Taq$^{\alpha}$I was tested to see if it behaved differently over fully and hemi-hydroxymethylation states. The inventors prepared the same 32-mer double strand DNA with hemi-hydroxymethylation, performed the same labeling procedure, and subjected to Taq$^{\alpha}$I digestion (FIG. 19B). While the hemi-5-hmC can be cut, hemi-$N_3$-5-glocose cannot block digestion as well as the fully-modified one (FIG. 19B, lane 1-4). Even with the bulkier group, biotin-$N_3$-5-gmC, present, the majority of DNA was still digested (FIG. 19B, lane 5-6). Thus, Taq$^{\alpha}$I digests the hemi-modified sequence but is blocked by the fully-modified one with biotin-N3-5-gmC. This noticeable difference of Taq$^{\alpha}$I in response to fully- and hemi-hydroxymethylation states after modification provides a method to distinguish these two states on TCGA sites by comparison of the sensitivity to restriction.

To further investigate if the difference in digestion between fully and hemi-hydroxymethylation states is universal in restriction enzymes, the inventors replaced the T*CGA site with C*GG (*C=5-hmC) in the previous 32-mer duplex DNA and performed the same assays using MspI (FIG. 20). Both fully and hemi-5-hmC can be cut by MspI completely before modification (FIG. 20A, lane 1-2 and FIG. 20B, lane 1-2). For a fully 5-hmC site, both $N_3$-gmC and biotin-$N_3$-5-gmC can block MspI digestion completely (FIG. 20A, lane 3-6), suggesting that MspI is more sensitive towards the steric hindrance of cytosine modification of the CpG dinucleotide; the presence of a glucose group on the inner C is enough for the protection from digestion. For the hemi-5-hmC site, it gave the same results as the fully-modified one: both the $N_3$-5-gmC and biotin-$N_3$-5-gmC can be protected from digestion (FIG. 20B, lane 3-6). This result is in accordance with our assumption that MspI is much easier to block and that it cannot distinguish the fully-modified 5-hmC site from hemi-5-hmC site as Taq$^{\alpha}$I.

REFERENCES

The following references, to the extent that they provide exemplary procedural or other details supplementary to those set forth herein, are specifically incorporated herein by reference.

Abdel-Wahab et al., Blood, 114:144-147, 2009.
Baskin et al., Proc. Natl. Acad. Sci. USA, 104:16793-16797, 2007.
Clark et al., Nucleic Acids Res. 22:2990-2997, 1994.
Crain, Methods Enzymol., 193:782-790, 1990.
Davis et al., Vis. Exp., (48), 2011.
Donnelly et al., Protein Expr. Purif., 47(2):446-154, 2006.
Edwards et al., Genome Res., 20:972-980, 2010.
Evans, Austral. J. Chem., 60(6): 384-395, 2007.
Flusberg et al., Nat. Methods, 7:461-465, 2010.
Frommer et al.: Proc. Natl. Acad. Sci. USA, 89:1827-1831, 1992.
Geier and Modrich, J. Biol. Chem., 254:1408-1413, 1979.
Goldberg et al., Cell, 128:635-638, 2007.
Hausinger, Crit. Rev. Biochem. Mol. Biol., 39:21-68, 2004.
Hayatsu and Shiragami, Biochemistry, 18:632-637, 1979.
Hayatsu et al., Biochemistry, 9:2858-2865, 1970.
Hein et al., Pharmaceut. Res., 25(10):2216-2230, 2008.
Huang et al., Nucleic Acids Res., 10:1579, 1982.
Huang et al., PLoS One, 5:e8888, 2010.
Ito et al., Nature, 466:1129-1133, 2010.
Jewett and Bertozzi, Chem. Soc. Rev., 39:1272, 2010.
Jin et al., Nucleic Acids Res., 38:e125, 2010.
Josse and Kornberg, Biol. Chem., 237:1968-1976, 1962.
Jung and Miller, J. Am. Chem. Soc., 103:1984-1992, 1981.

Kohlmann et al., In: *American Society of Hematology*, Abstract 417, LA, December, 2009.
Kolb et al., *Angew. Chem. Int. Ed.*, 40:2004-2021, 2001.
Kriaucionis and Heintz, *Science*, 324:929-930, 2009.
Langmead et al., *Genome Biol.*, 10:R25, 2009.
Lariviere and Morera, *J. Biol. Chem.*, 279:34715-34720, 2004.
Lee et al., *Hum. Mol. Genet.*, 18:2567-2574, 2009b.
Lee et al., *Hum. Mol. Genet.*, 18:835-846, 2009a.
Li and Durbin, *Bioinformatics*, 25:1754-1760, 2009.
Lim et al., *Cell*, 125:801-814, 2006.
Lister et al., *Nature*, 462:315-322, 2009.
Lyko et al., *Nature*, 408:538-540, 2000.
Margulies et al., *Nature*, 437:376-380, 2005.
Marinus and Morris, *J. Bacteriol.*, 114:1143-1150, 1973.
Maunakea et al., *Nature*, 466:253-257, 2010.
May and Hattman, *J. Bacteriol.*, 123:768-770, 1975.
Meissner et al., *Nature*, 454:766-770, 2008.
Meyer et al., *Chem. Bio. Chem.*, 4:610-614, 2003.
Moses and Moorhouse, *Chem. Soc. Rev.*, (36): 1249-1262, 2007.
Munzel et al., *Angew. Chem. Int. Ed.*, 49:5375-5377, 2010.
Nestor et al., *BioTechniques*, 48:317, 2010.
Ning et al., *Angew. Chem. Int. Ed.*, 47:2253-2255, 2008.
Rostovtsev et al., *Angew. Chem., Int. Ed.*, 41:2596, 2002.
Siegfried and Cedar, *Curr. Biol.*, 7:r305-307, 1997.
Silva et al., *PLoS Biol.*, 6:e253, 2008.
Singer-Sam et al., *Mol. Cell. Biol.*, 10:4987, 1990.
Skene et al. *Mol. Cell*, 37:457-468, 2010.
Sletten and Bertozzi, *Angew. Chem. Int. Ed.*, 48:6974-6998, 2009.
Smith et al., In: *American Society of Hematology*, Abstract 733, LA, December 2009.
Song et al., *Nat. Biotechnol.*, 29:68, 2011.
Speers and Cravatt, *Chem. Biol.*, 11:535-546, 2004.
Szpurka et al., In: *American Society of Hematology*, Abstract 2908, LA, December 2009.
Szulwach et al., *J. Cell Biol.*, 189:127-141, 2010.
Szwagierczak et al., *Nucleic Acids Res.*, 2011 (ahead of Pub)
Szwagierczak et al., *Nucleic Acids Res.*, 38:e181, 2010.
Tahiliani et al., *Science*, 324:930-935, 2009.
Tanabe et al., *J. Am. Chem. Soc.*, 129:8034-8040, 2007.
Tardy-Planechaud et al., *Nucleic Acids Res.*, 25:553, 1997.
Thomas et al., *Genome Biol.*, 13:2129-2141, 2003.
Thomas et al., *Nucleic Acids Res.*, 34:W645-650, 2006.
Tornoe et al., *J. Organic Chem.*, 67(9):3057-3064, 2002.
Weber et al., *Nature Genetics*, 37:853-862, 2005.
Wu and Zhang, *Mol. Cell Biol.*, 11:607-620, 2010.
Zeschnigk et al., *Hum. Mol. Genet.*, 6:387-395, 1997.
Zhang et al., *Genome Biol.*, 9, 137, 2008.

---

What is claimed is:

1. A method for distinguishing by glycosylation with a modified glucose molecule 5-hydroxymethylcytosine from 5-methylcytosine in a nucleic acid molecule of an isolated sample comprising:
placing in a reaction mixture the nucleic acid molecule with β-glucosyltransferase and a synthetically modified uridine diphosphoglucose (UDP-Glu) molecule comprising a modification moiety to glycosylate 5-hydroxymethyl-cytosines in the nucleic acid molecule with a modified glucose molecule, wherein the modification moiety comprises a linker, a detectable moiety, an isolation tag, a blocking moiety, or a functional moiety.

2. The method of claim 1, wherein the nucleic acid molecule is a nucleic acid molecule further purified from the isolated sample.

3. The method of claim 2, wherein the purified nucleic acid molecule is located on an array.

4. The method of claim 1, wherein the modification moiety comprises a linker.

5. The method of claim 4, wherein the modification moiety comprises an azide linker.

6. The method of claim 4, wherein the modification moiety comprises a thiol linker.

7. The method of claim 1, further comprising isolating the nucleic acid molecule from a cell of the isolated sample prior to glycosylation of the nucleic acid molecule.

8. The method of claim 1, further comprising reacting the modified glucose in the glycosylated nucleic acid molecule with a detectable or functional moiety.

9. The method of claim 8, wherein the glucose is modified with an azide or thiol linker.

10. The method of claim 1, further comprising placing the glycosylated nucleic acid molecule in a reaction mixture with an enzyme that is not β-glucosyltransferase.

11. The method of claim 10, wherein the enzyme is a restriction enzyme or a polymerase.

12. The method of claim 11, wherein the restriction enzyme is methylation-insensitive.

13. The method of claim 11, wherein the enzyme is polymerase.

14. The method of claim 13, wherein the glycosylated nucleic acid molecule is placed in a reaction mixture with polymerase, at least one primer, and one or more nucleotides under conditions to allow polymerization of a transcript of the glycosylated nucleic acid molecule.

15. The method of claim 14, further comprising sequencing the polymerized transcript of the glycosylated nucleic acid molecule.

16. The method of claim 1, further comprising isolating the glycosylated nucleic acid molecule from the reaction mixture.

17. A method for mapping by glycosylation with a modified glucose molecule 5-hydroxymethylcytosine in a nucleic acid molecule of an isolated sample comprising:
placing in a reaction mixture the nucleic acid molecule with β-glucosyltransferase and a synthetically modified uridine diphosphoglucose (UDP-Glu) molecule comprising a modification moiety to glycosylate 5-hydroxymethylcytosines in the nucleic acid molecule with the modified Glu molecule, wherein the modification moiety comprises a linker, a detectable moiety, an isolation tag, a blocking moiety, or a functional moiety; and
mapping the glycosylated 5-hydroxymethylcytosines in the glycosylated nucleic acid molecule by sequencing the glycosylated nucleic acid molecule.

18. The method of claim 17, wherein sequencing further comprises sequencing a control nucleic acid molecule.

19. The method of claim 14, wherein sequencing further comprises a primer extension assay.

20. The method of claim 17, further comprising placing the glycosylated nucleic acid molecule in a reaction mixture with an enzyme that is not β-glucosyltransferase before sequencing the glycosylated nucleic acid molecule.

21. The method of claim 20, wherein the enzyme is a restriction enzyme or a polymerase.

22. The method of claim 21, wherein the restriction enzyme is methylation-insensitive.

23. The method of claim 21, wherein the enzyme is polymerase.

24. The method of claim 23, wherein the glycosylated nucleic acid molecule is placed in a reaction mixture with polymerase, at least one primer, and one or more nucleotides under conditions to allow polymerization of a transcript of the glycosylated nucleic acid molecule.

25. The method of claim 24, further comprising sequencing the polymerized transcript of the glycosylated nucleic acid molecule.

* * * * *

SEQUENCE LISTING

```
<160> NUMBER OF SEQ ID NOS: 32

<210> SEQ ID NO 1
<211> LENGTH: 375
<212> TYPE: PRT
<213> ORGANISM: Artificial Sequence
<220> FEATURE:
<223> OTHER INFORMATION: Synthetic peptide

<400> SEQUENCE: 1

Ser His His His His His Ser Ser Gly Val Asp Leu Gly Thr Glu
1               5                   10                  15

Asn Leu Tyr Phe Gln Ser Asn Ala Met Lys Ile Ala Ile Ile Asn Met
            20                  25                  30

Gly Asn Asn Val Ile Asn Phe Lys Thr Val Pro Ser Ser Glu Thr Ile
        35                  40                  45

Tyr Leu Phe Lys Val Ile Ser Glu Met Gly Leu Asn Val Asp Ile Ile
    50                  55                  60

Ser Leu Lys Asn Gly Val Tyr Thr Lys Ser Phe Asp Glu Val Asp Val
65                  70                  75                  80

Asn Asp Tyr Asp Arg Leu Ile Val Val Asn Ser Ser Ile Asn Phe Phe
                85                  90                  95

Gly Gly Lys Pro Asn Leu Ala Ile Leu Ser Ala Gln Lys Phe Met Ala
            100                 105                 110

Lys Tyr Lys Ser Lys Ile Tyr Tyr Leu Phe Thr Asp Ile Arg Leu Pro
        115                 120                 125

Phe Ser Gln Ser Trp Pro Asn Val Lys Asn Arg Pro Trp Ala Tyr Leu
    130                 135                 140

Tyr Thr Glu Glu Glu Leu Leu Ile Lys Ser Pro Ile Lys Val Ile Ser
145                 150                 155                 160

Gln Gly Ile Asn Leu Asp Ile Ala Lys Ala Ala His Lys Lys Val Asp
                165                 170                 175

Asn Val Ile Glu Phe Glu Tyr Phe Pro Ile Glu Gln Tyr Lys Ile His
```

```
                    180                 185                 190
Met Asn Asp Phe Gln Leu Ser Lys Pro Thr Lys Thr Leu Asp Val
            195                 200                 205

Ile Tyr Gly Ser Phe Arg Ser Gly Gln Arg Glu Ser Lys Met Val
    210                 215                 220

Glu Phe Leu Phe Asp Thr Gly Leu Asn Ile Glu Phe Phe Gly Asn Ala
225                 230                 235                 240

Arg Glu Lys Gln Phe Lys Asn Pro Lys Tyr Pro Trp Thr Lys Ala Pro
                245                 250                 255

Val Phe Thr Gly Lys Ile Pro Met Asn Met Val Ser Glu Lys Asn Ser
            260                 265                 270

Gln Ala Ile Ala Ala Leu Ile Ile Gly Asp Lys Asn Tyr Asn Asp Asn
        275                 280                 285

Phe Ile Thr Leu Arg Val Trp Glu Thr Met Ala Ser Asp Ala Val Met
    290                 295                 300

Leu Ile Asp Glu Glu Phe Asp Thr Lys His Arg Ile Ile Asn Asp Ala
305                 310                 315                 320

Arg Phe Tyr Val Asn Asn Arg Ala Glu Leu Ile Asp Arg Val Asn Glu
                325                 330                 335

Leu Lys His Ser Asp Val Leu Arg Lys Glu Met Leu Ser Ile Gln His
            340                 345                 350

Asp Ile Leu Asn Lys Thr Arg Ala Lys Lys Ala Glu Trp Gln Asp Ala
        355                 360                 365

Phe Lys Lys Ala Ile Asp Leu
    370                 375

<210> SEQ ID NO 2
<211> LENGTH: 14
<212> TYPE: DNA
<213> ORGANISM: Artificial Sequence
<220> FEATURE:
<223> OTHER INFORMATION: Synthetic primer

<400> SEQUENCE: 2
aagcttctgg agtg                                                      14

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
aagctatgcc cgtgtcactc a                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
tgcatcaagc gacacacaga                                                20

<210> SEQ ID NO 5
<211> LENGTH: 21
<212> TYPE: DNA
<213> ORGANISM: Artificial Sequence
<220> FEATURE:
```

```
<223> OTHER INFORMATION: Synthetic primer

<400> SEQUENCE: 5
atcggcagaa ggtaggagga a                                              21

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
cctcacttgt ctccctgctt atc                                            23

<210> SEQ ID NO 7
<211> LENGTH: 23
<212> TYPE: DNA
<213> ORGANISM: Artificial Sequence
<220> FEATURE:
<223> OTHER INFORMATION: Synthetic primer

<400> SEQUENCE: 7
gagaccctct tgggacagtt acc                                            23

<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8
tgggttacat tcctcactcg aa                                             22

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
atgagtgaac catcccatgc a                                              21

<210> SEQ ID NO 10
<211> LENGTH: 19
<212> TYPE: DNA
<213> ORGANISM: Artificial Sequence
<220> FEATURE:
<223> OTHER INFORMATION: Synthetic primer

<400> SEQUENCE: 10
tcagccagtg cctcgtgat                                                 19

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
tgcaacaagt gcctgacata ca                                             22

<210> SEQ ID NO 12
```

```
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
ttgtgtgtgc aatcattgtt catt                                          24

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
cctccagtcc aggcagtgat                                               20

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
cgtcaaagga gtcctggtca a                                             21

<210> SEQ ID NO 15
<211> LENGTH: 21
<212> TYPE: DNA
<213> ORGANISM: Artificial Sequence
<220> FEATURE:
<223> OTHER INFORMATION: Synthetic primer

<400> SEQUENCE: 15
cctccttagg gccattctca a                                             21

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
cggacctgat gggcatagta g                                             21

<210> SEQ ID NO 17
<211> LENGTH: 25
<212> TYPE: DNA
<213> ORGANISM: Artificial Sequence
<220> FEATURE:
<223> OTHER INFORMATION: Synthetic primer

<400> SEQUENCE: 17
tctactcccg tttcaccgtt tatat                                         25

<210> SEQ ID NO 18
<211> LENGTH: 17
<212> TYPE: DNA
<213> ORGANISM: Artificial Sequence
<220> FEATURE:
<223> OTHER INFORMATION: Synthetic primer

<400> SEQUENCE: 18
```

```
gcccatgcag ccagttg                                                    17

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
agagggacat gggcatcaca                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
accgctgact gccagtacct                                                 20

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21
gacccaggag agaaagcatg ag                                              22

<210> SEQ ID NO 22
<211> LENGTH: 21
<212> TYPE: DNA
<213> ORGANISM: Artificial Sequence
<220> FEATURE:
<223> OTHER INFORMATION: Synthetic primer

<400> SEQUENCE: 22
tgactccgtg aacaggaatg g                                               21

<210> SEQ ID NO 23
<211> LENGTH: 26
<212> TYPE: DNA
<213> ORGANISM: Artificial Sequence
<220> FEATURE:
<223> OTHER INFORMATION: Synthetic primer

<400> SEQUENCE: 23
agagagatag aggtggaagt caggtt                                          26

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
aggagcctgg agcagaaatg                                                 20

<210> SEQ ID NO 25
<211> LENGTH: 24
<212> TYPE: DNA
<213> ORGANISM: Artificial Sequence
<220> FEATURE:
```

<223> OTHER INFORMATION: Synthetic primer

<400> SEQUENCE: 25
gaacagtgta aggtccaccc aagt                                              24

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
ggaaaaacgg gttcggaaag                                                   20

<210> SEQ ID NO 27
<211> LENGTH: 22
<212> TYPE: DNA
<213> ORGANISM: Artificial Sequence
<220> FEATURE:
<223> OTHER INFORMATION: Synthetic primer

<400> SEQUENCE: 27
tggcacactt gagcaaatcc ta                                                22

<210> SEQ ID NO 28
<211> LENGTH: 24
<212> TYPE: DNA
<213> ORGANISM: Artificial Sequence
<220> FEATURE:
<223> OTHER INFORMATION: Synthetic primer

<400> SEQUENCE: 28
tgccaactat tggaatggaa aata                                              24

<210> SEQ ID NO 29
<211> LENGTH: 23
<212> TYPE: DNA
<213> ORGANISM: Artificial Sequence
<220> FEATURE:
<223> OTHER INFORMATION: Synthetic primer

<400> SEQUENCE: 29
gaacagccag caaccttcta aaa                                               23

<210> SEQ ID NO 30
<211> LENGTH: 21
<212> TYPE: DNA
<213> ORGANISM: Artificial Sequence
<220> FEATURE:
<223> OTHER INFORMATION: Synthetic primer

<400> SEQUENCE: 30
caacagcgtc atgggataac a                                                 21

<210> SEQ ID NO 31
<211> LENGTH: 17
<212> TYPE: DNA
<213> ORGANISM: Artificial Sequence
<220> FEATURE:
<223> OTHER INFORMATION: Synthetic primer

<400> SEQUENCE: 31
acaacccgcc caccaat                                                      17

<210> SEQ ID NO 32

```
<211> LENGTH: 24
<212> TYPE: DNA
<213> ORGANISM: Artificial Sequence
<220> FEATURE:
<223> OTHER INFORMATION: Synthetic primer

<400> SEQUENCE: 32
tttagctacc cccaagttta atgg                                             24
```